(12) United States Patent
Lee

(10) Patent No.: US 11,518,805 B2
(45) Date of Patent: Dec. 6, 2022

(54) BINDING INHIBITOR BETWEEN TCTP DIMER TYPE IGE-DEPENDENT HISTAMINE RELEASING FACTOR AND RECEPTOR THEREOF, AND USE THEREOF

(71) Applicant: EWHA UNIVERSITY—INDUSTRY COLLABORATION FOUNDATION, Seoul (KR)

(72) Inventor: Kyunglim Lee, Seoul (KR)

(73) Assignee: EWHA UNIVERSITY—INDUSTRY COLLABORATION FOUNDATION, Seoul (KR)

( * ) Notice: Subject to any disclaimer, the term of this patent is extended or adjusted under 35 U.S.C. 154(b) by 373 days.

(21) Appl. No.: 16/862,981

(22) Filed: Apr. 30, 2020

(65) Prior Publication Data
US 2020/0255513 A1    Aug. 13, 2020

Related U.S. Application Data

(60) Division of application No. 15/382,277, filed on Dec. 16, 2016, now Pat. No. 10,703,812, which is a continuation of application No. PCT/KR2015/006088, filed on Jun. 16, 2015.

(30) Foreign Application Priority Data

Jun. 16, 2014 (KR) .................. 10-2014-0072700

(51) Int. Cl.
| | | |
|---|---|---|
| C07K 7/00 | (2006.01) | |
| C07K 16/24 | (2006.01) | |
| A61K 38/16 | (2006.01) | |
| A61K 39/395 | (2006.01) | |
| C07K 14/47 | (2006.01) | |
| A61K 38/19 | (2006.01) | |
| A61P 27/14 | (2006.01) | |
| C07K 14/52 | (2006.01) | |
| A61K 9/14 | (2006.01) | |
| A61K 9/20 | (2006.01) | |
| A61K 9/48 | (2006.01) | |
| A61K 39/00 | (2006.01) | |

(52) U.S. Cl.
CPC .......... C07K 16/244 (2013.01); A61K 9/14 (2013.01); A61K 9/20 (2013.01); A61K 9/48 (2013.01); A61K 38/16 (2013.01); A61K 38/19 (2013.01); A61K 39/395 (2013.01); A61K 39/3955 (2013.01); A61P 27/14 (2018.01); C07K 14/4703 (2013.01); C07K 14/52 (2013.01); *A61K 2039/505* (2013.01); *C07K 2317/35* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 6,710,165 B2 | 3/2004 | Lee et al. | |
| 7,772,368 B2 * | 8/2010 | Lee .................. | A61P 43/00 424/193.1 |
| 2004/0175772 A1 | 9/2004 | Amson et al. | |
| 2006/0165677 A1 | 7/2006 | Lee et al. | |
| 2013/0084293 A1 | 4/2013 | Kawakami et al. | |

FOREIGN PATENT DOCUMENTS

| | | |
|---|---|---|
| EP | 1 167 526 | 1/2002 |
| EP | 1 683 866 | 7/2006 |
| JP | 2002-330772 | 11/2002 |
| WO | WO 02/052274 | 7/2002 |
| WO | WO 2007/097561 | 8/2007 |
| WO | WO 2011/123697 A2 | 10/2011 |

OTHER PUBLICATIONS

Bommer and Thiele, "The translationally controlled tumour protein (TCTP)," Int J Biochem Cell Biol 36(3):379-385, 2004.

Dunn et al., "The Synthesis of Glycylglycine," J. Biol. Chem., vol. 99:217-220, 1932.

Hershko et al., "Role of the α-amino Group of Protein in Ubiquitin-Mediated Protein Breakdown," Proc. Natl. Acad. Sci. USA, vol. 81:7021-7025, 1984.

Jung et al., "Translationally Controlled Tumor Protein Interacts with the Third Cytoplasmic Domain of Na,K-ATPase α Subunit and Inhibits the Pump Activity in HeLa Cells," J Biol Chem 279(48):49868-49875, 2004.

(Continued)

*Primary Examiner* — Michael Szperka
(74) *Attorney, Agent, or Firm* — Klarquist Sparkman, LLP

(57) ABSTRACT

The present invention relates to a receptor-binding domain of an IgE-dependent histamine releasing factor (HRF), and a use thereof, and more specifically, ascertains, as an HRF structural region, and a FL domain and an H2 domain which bind to a receptor of HRF existing in a cell membrane, ascertains the C-terminus domain of the HRF, and ascertains that a material binding thereto inhibits IL-8 secretion, thereby determining that the FL and H2 domains and the C-terminus domain can be utilized in: the development of a therapeutic agent for treatment and prevention of HRF-related disease including allergic diseases such as asthma, rhinitis, atopic dermatitis, and anaphylaxis; inflammatory diseases such as rheumatoid arthritis; and malaria, and a method for screening for the HRF-related diseases.

11 Claims, 54 Drawing Sheets

Specification includes a Sequence Listing.

(56) References Cited

OTHER PUBLICATIONS

Kashiwakura et al., 'Histamine-releasing factor has a proinflammatory role in mouse models of asthma and allergy,' *The Journal of Clinical Investigation*, vol. 122:218-228, 2012.
Kawakami et al., 'Histamine-Releasing Factor and Immunoglobulins in Asthma and Allergy,' *Allergy, Asthma & Immunology Research*, vol. 6:6-12, 2014.
Kim et al., "Identification of the Calcium Binding Sites in Translationally Controlled Tumor Protein," *Arch. Pharm Res.*, vol. 23:633-636, 2000.
Kim et al., "Dimerization of TCTP and its clinical implications for allergy," *Biochimie* 95:659-666, 2013.
Macdonald, 'Potential role of histamine releasing factor (HRF) as a therapeutic target for treating asthma and allergy,' *Journal of Asthma and Allergy*, vol. 5:51-59, 2012.
Nuijens et al., "Enzymatic C-Terminal Amidation of Amino Acids and Peptides," *Tetrahedron Lett.*, vol. 53:3777-3779, 2012.

\* cited by examiner

* = p<0.05 , ** = p<0.01

N; Negative, P; Positive, PT; Protopic, dTBP2; 7-mer peptide

SEQUENCE LISTING

```
<160> NUMBER OF SEQ ID NOS: 39

<210> SEQ ID NO 1
<211> LENGTH: 32
<212> TYPE: PRT
<213> ORGANISM: Artificial Sequence
<220> FEATURE:
<223> OTHER INFORMATION: ab1

<400> SEQUENCE: 1

Ser Arg Thr Glu Gly Ala Ile Asp Asp Ser Leu Ile Gly Gly Asn Ala
1               5                   10                  15

Ser Ala Glu Gly Pro Glu Gly Glu Gly Thr Glu Ser Thr Val Val Thr
            20                  25                  30

<210> SEQ ID NO 2
<211> LENGTH: 32
<212> TYPE: PRT
<213> ORGANISM: Artificial Sequence
<220> FEATURE:
<223> OTHER INFORMATION: ab2

<400> SEQUENCE: 2

Ser Arg Thr Glu Gly Asn Ile Asp Asp Ser Leu Ile Gly Gly Asn Ala
1               5                   10                  15

Ser Ala Glu Gly Pro Glu Gly Glu Gly Thr Glu Ser Thr Val Ile Thr
            20                  25                  30

<210> SEQ ID NO 3
<211> LENGTH: 29
<212> TYPE: PRT
<213> ORGANISM: Artificial Sequence
<220> FEATURE:
<223> OTHER INFORMATION: ab3

<400> SEQUENCE: 3

Arg Thr Glu Gly Ala Ile Asp Asp Ser Leu Ile Gly Gly Asn Ala Ser
1               5                   10                  15

Ala Glu Gly Pro Glu Gly Glu Gly Thr Glu Ser Thr Val
            20                  25

<210> SEQ ID NO 4
```

```
<211> LENGTH: 29
<212> TYPE: PRT
<213> ORGANISM: Artificial Sequence
<220> FEATURE:
<223> OTHER INFORMATION: ab4

<400> SEQUENCE: 4

Arg Thr Glu Gly Asn Ile Asp Asp Ser Leu Ile Gly Gly Asn Ala Ser
1               5                   10                  15

Ala Glu Gly Pro Glu Gly Glu Gly Thr Glu Ser Thr Val
            20                  25

<210> SEQ ID NO 5
<211> LENGTH: 96
<212> TYPE: DNA
<213> ORGANISM: Artificial Sequence
<220> FEATURE:
<223> OTHER INFORMATION: ab1 n

<400> SEQUENCE: 5
agtagaacag agggtgccat cgatgattca ctcattggtg aaatgcttc cgctgaaggt     60 ccggagggcg aaggtaccga aagcacagta gtcacc                             96

<210> SEQ ID NO 6
<211> LENGTH: 96
<212> TYPE: DNA
<213> ORGANISM: Artificial Sequence
<220> FEATURE:
<223> OTHER INFORMATION: ab2 n

<400> SEQUENCE: 6
agtagaacag agggtgccat cgatgactcg ctcatcggtg aaatgcttc cgctgaaggt     60 ccggagggcg aaggtaccga aagcacagta gtcacc                             96

<210> SEQ ID NO 7
<211> LENGTH: 96
<212> TYPE: DNA
<213> ORGANISM: Artificial Sequence
<220> FEATURE:
<223> OTHER INFORMATION: ab3 n

<400> SEQUENCE: 7
agtaggacag aaggtaacat tgatgactcg ctcattggtg aaatgcctc cgctgaaggc     60 cccgagggcg aaggtaccga aagcacagta atcact                             96

<210> SEQ ID NO 8
<211> LENGTH: 87
<212> TYPE: DNA
<213> ORGANISM: Artificial Sequence
<220> FEATURE:
<223> OTHER INFORMATION: ab4 n

<400> SEQUENCE: 8
agaacagagg gtgccatcga tgattcactc attggtggaa atgcttccgc tgaaggtccg    60
gagggcgaag gtaccgaaag cacagta                                       87

<210> SEQ ID NO 9
<211> LENGTH: 87
<212> TYPE: DNA
<213> ORGANISM: Artificial Sequence
<220> FEATURE:
<223> OTHER INFORMATION: ab5 n

<400> SEQUENCE: 9
```

```
agaacagagg gtgccatcga tgactcgctc atcggtggaa atgcttccgc tgaaggtccg    60
gagggcgaag gtaccgaaag cacagta                                        87

<210> SEQ ID NO 10
<211> LENGTH: 87
<212> TYPE: DNA
<213> ORGANISM: Artificial Sequence
<220> FEATURE:
<223> OTHER INFORMATION: ab5 n

<400> SEQUENCE: 10
aggacagaag gtaacattga tgactcgctc attggtggaa atgcctccgc tgaaggcccc    60
gagggcgaag gtaccgaaag cacagta                                        87

<210> SEQ ID NO 11
<211> LENGTH: 25
<212> TYPE: PRT
<213> ORGANISM: Artificial Sequence
<220> FEATURE:
<223> OTHER INFORMATION: H2

<400> SEQUENCE: 11

Thr Lys Glu Ala Tyr Lys Lys Tyr Ile Lys Asp Tyr Met Lys Ser Leu
1               5                   10                  15

Lys Gly Lys Leu Glu Glu Gln Lys Pro
            20                  25

<210> SEQ ID NO 12
<211> LENGTH: 25
<212> TYPE: PRT
<213> ORGANISM: Artificial Sequence
<220> FEATURE:
<223> OTHER INFORMATION: H2 2

<400> SEQUENCE: 12

Thr Lys Glu Ala Tyr Lys Lys Tyr Ile Lys Asp Tyr Met Lys Ser Ile
1               5                   10                  15

Lys Gly Lys Leu Glu Glu Gln Arg Pro
            20                  25

<210> SEQ ID NO 13
<211> LENGTH: 75
<212> TYPE: DNA
<213> ORGANISM: Artificial Sequence
<220> FEATURE:
<223> OTHER INFORMATION: H2 n

<400> SEQUENCE: 13 acaaagagg cctacaaaaa gtatatcaaa gactacatga aatcactcaa gggcaaactt    60
gaagaacaga aacca                                                    75

<210> SEQ ID NO 14
<211> LENGTH: 75
<212> TYPE: DNA
<213> ORGANISM: Artificial Sequence
<220> FEATURE:
<223> OTHER INFORMATION: H2 2 n

<400> SEQUENCE: 14 acaaagagg cttacaaaaa gtacatcaaa gactacatga aatcactcaa aggcaaactt    60
gaagagcaga aacca                                                    75
```

<210> SEQ ID NO 15
<211> LENGTH: 75
<212> TYPE: DNA
<213> ORGANISM: Artificial Sequence
<220> FEATURE:
<223> OTHER INFORMATION: H2 3 n

<400> SEQUENCE: 15

```
acaaaagaag cctacaagaa gtacatcaaa gattacatga atcaatcaa agggaaactt      60 gaagaacaga gacca                                                      75
```

<210> SEQ ID NO 16
<211> LENGTH: 519
<212> TYPE: DNA
<213> ORGANISM: Artificial Sequence
<220> FEATURE:
<223> OTHER INFORMATION: f-TCTP

<400> SEQUENCE: 16

```
atgattatct accgggacct catcagccac gatgagatgt tctccgacat ctacaagatc      60
cgggagatcg cggacgggtt gtgcctggag gtggagggga agatggtcag taggacagaa     120
ggtaacattg atgactcgct cattggtgga atgcctccg ctgaaggccc cgagggcgaa      180
ggtaccgaaa gcacagtaat cactggtgtc gatattgtca tgaaccatca cctgcaggaa     240
acaagtttca caaagaagc ctacaagaag tacatcaaag attacatgaa atcaatcaaa      300 gggaacttg aagaacagag accagaaaga gtaaaacctt ttatgacagg ggctgcagaa      360
caaatcaagc acatccttgc taatttcaaa aactaccagt tctttattgg tgaaaacatg     420
aatccagatg gcatggttgc tctattggac taccgtgagg atggtgtgac cccatatatg     480
atttctttta aggatgggttt agaaatggaa aaatgttaa                           519
```

<210> SEQ ID NO 17
<211> LENGTH: 172
<212> TYPE: PRT
<213> ORGANISM: Artificial Sequence
<220> FEATURE:
<223> OTHER INFORMATION: f-TCTP P

<400> SEQUENCE: 17

```
Met Ile Ile Tyr Arg Asp Leu Ile Ser His Asp Glu Met Phe Ser Asp
1               5                   10                  15

Ile Tyr Lys Ile Arg Glu Ile Ala Asp Gly Leu Cys Leu Glu Val Glu
            20                  25                  30

Gly Lys Met Val Ser Arg Thr Glu Gly Asn Ile Asp Asp Ser Leu Ile
        35                  40                  45

Gly Gly Asn Ala Ser Ala Glu Gly Pro Glu Gly Glu Gly Thr Glu Ser
    50                  55                  60

Thr Val Ile Thr Gly Val Asp Ile Val Met Asn His His Leu Gln Glu
65                  70                  75                  80

Thr Ser Phe Thr Lys Glu Ala Tyr Lys Lys Tyr Ile Lys Asp Tyr Met
                85                  90                  95

Lys Ser Ile Lys Gly Lys Leu Glu Glu Gln Arg Pro Glu Arg Val Lys
            100                 105                 110

Pro Phe Met Thr Gly Ala Ala Glu Gln Ile Lys His Ile Leu Ala Asn
        115                 120                 125

Phe Lys Asn Tyr Gln Phe Phe Ile Gly Glu Asn Met Asn Pro Asp Gly
    130                 135                 140
```

```
Met Val Ala Leu Leu Asp Tyr Arg Glu Asp Gly Val Thr Pro Tyr Met
145                 150                 155                 160

Ile Phe Phe Lys Asp Gly Leu Glu Met Glu Lys Cys
                165                 170
```

<210> SEQ ID NO 18
<211> LENGTH: 459
<212> TYPE: DNA
<213> ORGANISM: Artificial Sequence
<220> FEATURE:
<223> OTHER INFORMATION: TCTP

<400> SEQUENCE: 18

```
atgattattt atcgcgatct gattagccat gatgaaatgt tttcggatat ttataaaatt     60
cgcgaaattg cggatggcct gtgcctggaa gtggaaggca aaatggtgag cggcggcatt    120
accggcgtgg atattgtgat gaaccatcat ctgcaggaaa ccagctttac caaagaagcg    180
tataaaaaat atattaaaga ttatatgaaa tcgattaaag caaactgga agaacagcgc     240 ccggaacgcg tgaaaccgtt tatgaccggc gcggcggaac agattaaaca tattctggcg    300
aactttaaaa actatcagtt ttttattggc gaaaacatga acccggatgg catggtggcg    360
ctgctggatt atcgcgaaga tggcgtgacc ccgtatatga ttttttttaa agatggcctg    420
gaaatggaaa aatgcctcga gcaccaccac caccaccac                            459
```

<210> SEQ ID NO 19
<211> LENGTH: 153
<212> TYPE: PRT
<213> ORGANISM: Artificial Sequence
<220> FEATURE:
<223> OTHER INFORMATION: TCTP P

<400> SEQUENCE: 19

```
Met Ile Ile Tyr Arg Asp Leu Ile Ser His Asp Glu Met Phe Ser Asp
1               5                   10                  15

Ile Tyr Lys Ile Arg Glu Ile Ala Asp Gly Leu Cys Leu Glu Val Glu
                20                  25                  30

Gly Lys Met Val Ser Gly Gly Ile Thr Gly Val Asp Ile Val Met Asn
            35                  40                  45

His His Leu Gln Glu Thr Ser Phe Thr Lys Glu Ala Tyr Lys Lys Tyr
    50                  55                  60

Ile Lys Asp Tyr Met Lys Ser Ile Lys Gly Lys Leu Glu Glu Gln Arg
65                  70                  75                  80

Pro Glu Arg Val Lys Pro Phe Met Thr Gly Ala Ala Glu Gln Ile Lys
                85                  90                  95

His Ile Leu Ala Asn Phe Lys Asn Tyr Gln Phe Phe Ile Gly Glu Asn
            100                 105                 110

Met Asn Pro Asp Gly Met Val Ala Leu Leu Asp Tyr Arg Glu Asp Gly
        115                 120                 125

Val Thr Pro Tyr Met Ile Phe Phe Lys Asp Gly Leu Glu Met Glu Lys
    130                 135                 140

Cys Leu Glu His His His His His His
145                 150
```

<210> SEQ ID NO 20
<211> LENGTH: 28
<212> TYPE: DNA
<213> ORGANISM: Artificial Sequence
<220> FEATURE:
<223> OTHER INFORMATION: primer_forward -continued

<400> SEQUENCE: 20
ggaattccat atgattatct accgggac				28

<210> SEQ ID NO 21
<211> LENGTH: 27
<212> TYPE: DNA
<213> ORGANISM: Artificial Sequence
<220> FEATURE:
<223> OTHER INFORMATION: primer_reverse

<400> SEQUENCE: 21
ccgctcgaga cattttttcca tttctaa				27

<210> SEQ ID NO 22
<211> LENGTH: 24
<212> TYPE: PRT
<213> ORGANISM: Artificial
<220> FEATURE:
<223> OTHER INFORMATION: Helix3 domain

<400> SEQUENCE: 22

Lys Pro Glu Arg Val Lys Pro Phe Met Thr Gly Ala Ala Glu Gln Ile
1               5                   10                  15

Lys His Ile Leu Ala Asn Phe Asn
            20

<210> SEQ ID NO 23
<211> LENGTH: 7
<212> TYPE: PRT
<213> ORGANISM: Artificial Sequence
<220> FEATURE:
<223> OTHER INFORMATION: IgE-dependent histamine-releasing factor
      binding peptide

<400> SEQUENCE: 23

Leu Val Thr Tyr Pro Leu Pro
1               5

<210> SEQ ID NO 24
<211> LENGTH: 7
<212> TYPE: PRT
<213> ORGANISM: Artificial Sequence
<220> FEATURE:
<223> OTHER INFORMATION: IgE-dependent histamine-releasing factor
      binding peptide2

<400> SEQUENCE: 24

Trp Tyr Val Tyr Pro Ser Met
1               5

<210> SEQ ID NO 25
<211> LENGTH: 7
<212> TYPE: PRT
<213> ORGANISM: Artificial Sequence
<220> FEATURE:
<223> OTHER INFORMATION: IgE-dependent histamine-releasing factor
      binding peptide3

<400> SEQUENCE: 25

Trp Glu Phe Pro Gly Trp Met
1               5

<210> SEQ ID NO 26
<211> LENGTH: 7
<212> TYPE: PRT

```
<213> ORGANISM: Artificial
<220> FEATURE:
<223> OTHER INFORMATION: IgE-dependent histamine-releasing factor
      binding peptide4

<400> SEQUENCE: 26

Ala Tyr Val Tyr Pro Ser Met
1               5

<210> SEQ ID NO 27
<211> LENGTH: 7
<212> TYPE: PRT
<213> ORGANISM: Artificial
<220> FEATURE:
<223> OTHER INFORMATION: IgE-dependent histamine-releasing factor
      binding peptide5

<400> SEQUENCE: 27

Trp Ala Val Tyr Pro Ser Met
1               5

<210> SEQ ID NO 28
<211> LENGTH: 7
<212> TYPE: PRT
<213> ORGANISM: Artificial
<220> FEATURE:
<223> OTHER INFORMATION: IgE-dependent histamine-releasing factor
      binding peptide6

<400> SEQUENCE: 28

Trp Tyr Ala Tyr Pro Ser Met
1               5

<210> SEQ ID NO 29
<211> LENGTH: 7
<212> TYPE: PRT
<213> ORGANISM: Artificial Sequence
<220> FEATURE:
<223> OTHER INFORMATION: IgE-dependent histamine-releasing factor
      binding peptide7

<400> SEQUENCE: 29

Trp Tyr Val Ala Pro Ser Met
1               5

<210> SEQ ID NO 30
<211> LENGTH: 7
<212> TYPE: PRT
<213> ORGANISM: Artificial Sequence
<220> FEATURE:
<223> OTHER INFORMATION: IgE-dependent histamine-releasing factor
      binding peptide8

<400> SEQUENCE: 30

Trp Tyr Val Tyr Lys Ser Met
1               5

<210> SEQ ID NO 31
<211> LENGTH: 7
<212> TYPE: PRT
<213> ORGANISM: Artificial Sequence
<220> FEATURE:
<223> OTHER INFORMATION: IgE-dependent histamine releasing factor
      binding peptide9

<400> SEQUENCE: 31

Trp Tyr Val Tyr Pro Ala Met
1               5
```

<210> SEQ ID NO 32
<211> LENGTH: 7
<212> TYPE: PRT
<213> ORGANISM: Artificial Sequence
<220> FEATURE:
<223> OTHER INFORMATION: IgE-dependent histamine releasing factor
      binding peptide10

<400> SEQUENCE: 32

Trp Tyr Val Tyr Pro Ser Ala
1               5

<210> SEQ ID NO 33
<211> LENGTH: 11
<212> TYPE: PRT
<213> ORGANISM: Artificial Sequence
<220> FEATURE:
<223> OTHER INFORMATION: C-term RAT/MOUSE

<400> SEQUENCE: 33

Phe Phe Lys Asp Gly Leu Glu Met Glu Lys Cys
1               5                   10

<210> SEQ ID NO 34
<211> LENGTH: 11
<212> TYPE: PRT
<213> ORGANISM: Artificial Sequence
<220> FEATURE:
<223> OTHER INFORMATION: C-term Homo sapiens

<400> SEQUENCE: 34

Phe Phe Lys Asp Gly Leu Lys Met Glu Lys Cys
1               5                   10

<210> SEQ ID NO 35
<211> LENGTH: 33
<212> TYPE: DNA
<213> ORGANISM: Artificial Sequence
<220> FEATURE:
<223> OTHER INFORMATION: C-term n

<400> SEQUENCE: 35
ttctttaagg agggcttaga gatggaaaaa tgt                                   33

<210> SEQ ID NO 36
<211> LENGTH: 33
<212> TYPE: DNA
<213> ORGANISM: Artificial Sequence
<220> FEATURE:
<223> OTHER INFORMATION: C-term MOUSE

<400> SEQUENCE: 36
ttctttaagg atggcttaga gatggagaaa tgt                                   33

<210> SEQ ID NO 37
<211> LENGTH: 33
<212> TYPE: DNA
<213> ORGANISM: Artificial Sequence
<220> FEATURE:
<223> OTHER INFORMATION: C-term n Homo sapiens

<400> SEQUENCE: 37
ttctttaagg atggtttaaa aatggaaaaa tgt                                   33

<210> SEQ ID NO 38

```
<211> LENGTH: 34
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (2)..(2)
<223> OTHER INFORMATION: Xaa = Ser or Thr
<220> FEATURE:
<221> NAME/KEY: MISC_FEATURE
<222> LOCATION: (7)..(7)
<223> OTHER INFORMATION: Xaa = Ala, Asn or Gln
<220> FEATURE:
<221> NAME/KEY: MISC_FEATURE
<222> LOCATION: (29)..(29)
<223> OTHER INFORMATION: Xaa = Ser or Ala
<220> FEATURE:
<221> NAME/KEY: MISC_FEATURE
<222> LOCATION: (32)..(32)
<223> OTHER INFORMATION: Xaa = Val or Ile
<220> FEATURE:
<221> NAME/KEY: misc_feature
<222> LOCATION: (34)..(34)
<223> OTHER INFORMATION: Xaa can be any naturally occurring amino acid

<400> SEQUENCE: 38

Xaa Xaa Arg Thr Glu Gly Xaa Ile Asp Asp Ser Leu Ile Gly Gly Asn
1               5                   10                  15

Ala Ser Ala Glu Gly Pro Glu Gly Glu Gly Thr Glu Xaa Thr Val Xaa
            20                  25                  30

Thr Xaa

<210> SEQ ID NO 39
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa = Ala or Ser
<220> FEATURE:
<221> NAME/KEY: MISC_FEATURE
<222> LOCATION: (16)..(16)
<223> OTHER INFORMATION: Xaa = Ala or Ser
<220> FEATURE:
<221> NAME/KEY: MISC_FEATURE
<222> LOCATION: (17)..(17)
<223> OTHER INFORMATION: Xaa = Leu or Ile
<220> FEATURE:
<221> NAME/KEY: MISC_FEATURE
<222> LOCATION: (19)..(19)
<223> OTHER INFORMATION: Xaa = Gly or Ala
<220> FEATURE:
<221> NAME/KEY: MISC_FEATURE
<222> LOCATION: (20)..(20)
<223> OTHER INFORMATION: Xaa = Lys or Arg
<220> FEATURE:
<221> NAME/KEY: MISC_FEATURE
<222> LOCATION: (24)..(24)
<223> OTHER INFORMATION: Xaa = Gln or His
<220> FEATURE:
<221> NAME/KEY: MISC_FEATURE
<222> LOCATION: (25)..(25)
<223> OTHER INFORMATION: Xaa = Lys or Arg
```

```
<220> FEATURE:
<221> NAME/KEY: misc_feature
<222> LOCATION: (27)..(27)
<223> OTHER INFORMATION: Xaa can be any naturally occurring amino acid

<400> SEQUENCE: 39

Xaa Thr Lys Glu Xaa Tyr Lys Lys Tyr Ile Lys Asp Tyr Met Lys Xaa
1               5                   10                  15

Xaa Lys Xaa Xaa Leu Glu Glu Xaa Xaa Pro Xaa
            20                  25
```

BINDING INHIBITOR BETWEEN TCTP DIMER TYPE IGE-DEPENDENT HISTAMINE RELEASING FACTOR AND RECEPTOR THEREOF, AND USE THEREOF

CROSS REFERENCE TO RELATED APPLICATIONS

This application is a divisional of U.S. application Ser. No. 15/382,277, filed Dec. 16, 2016, which is a continuation of International Application No. PCT/KR2015/006088, filed Jun. 16, 2015, which claims the benefit of Korean Application No. KR 10-2014-0072700, filed Jun. 16, 2014. The above-listed applications are herein incorporated by reference in their entirety.

INCORPORATION OF ELECTRONIC SEQUENCE LISTING

The Sequence Listing is submitted as an ASCII text file, created on Apr. 29, 2020, 14.7 KB, which is incorporated by reference herein.

BACKGROUND OF THE INVENTION

1. Field of the Invention

The present invention relates to a binding inhibitor between IgE-dependent histamine releasing factor which is a TCTP (Translationally Controlled Tumor Protein) dimer form and a receptor thereof, and a use of the binding inhibitor.

2. Description of the Related Art

TCTP (Translationally Controlled Tumor Protein) is also called IgE-dependent histamine releasing factor (HRF), which is known to induce late phase allergic reaction by inducing histamine release from basophils (MacDonald et al., Science, 269, 688-690, 1995). Bheekha-Escura et al proposed that HRF binds to a specific cell membrane receptor but the exact mechanism of the binding between HRF and its receptor has not been disclosed, yet (Bheekha-Escura et al., Blood, 96, 2191-2198, 2000).

Thus, the present inventors have been studied on the binding between the IgE-dependent histamine releasing factor which is a TCTP (Translationally Controlled Tumor Protein) dimer form and the receptor thereof and as a result the inventors confirmed that the flexible loop (FL) domain which is the intrinsically unfolded protein (IUP) domain and the helix 2 (H2) domain in the helix domain of active form of HRF, TCTP dimer, were the regions responsible for a specific binding to its receptor on the cell membrane. Further, the present inventors confirmed that the HRF receptor binding domain could be efficiently used for the development of a binding inhibitor and a preventive drug for the treatment of various inflammatory diseases, allergic diseases, and malaria, leading to the completion of the invention.

SUMMARY OF THE INVENTION

It is an object of the present invention to provide a pharmaceutical composition for the diagnosis, prevention or treatment of one or more diseases selected from the group consisting of allergic diseases, inflammatory diseases, and malaria, comprising the binding inhibitor between the IgE-dependent histamine releasing factor which is a TCTP (Translationally Controlled Tumor Protein) dimer form IgE-dependent histamine releasing factor and its receptor existing in the cell membrane as an active ingredient.

It is another object of the present invention to provide a method for preparing a therapeutic agent for the HRF-related disease selected from the group consisting of allergic diseases, inflammatory diseases, and malaria, a method for screening thereof, a method for preparing a diagnostic kit, and a method for preparing an antibody in relation to the above, by examining the FL domain and Helix 2 domain as the regions related to the binding between TCTP dimer form-HRF and its receptor existing in the cell membrane and further examining C-terminal domain involved in the formation of the dimer or the receptor activation.

To achieve the objects above, the present invention provides a pharmaceutical composition for the diagnosis, prevention or treatment of one or more diseases selected from the group consisting of allergic diseases, inflammatory diseases, and malaria, comprising the binding inhibitor between IgE-dependent histamine releasing factor and its receptor existing in the cell membrane as an active ingredient.

The present invention also provides a method for screening a candidate material for the diagnosis, prevention, or treatment of one or more HRF-related diseases selected from the group consisting of allergic diseases, inflammatory diseases, and malaria, comprising the following steps:

1) contacting one or more materials selected from the group consisting of FL domain and H2 domain of HRF, and their fragments with the test sample together with the HRF receptor;

2) measuring the binding strength between the said domains, their analogues, or their fragments with the HRF receptor; and 3) selecting the test sample that was confirmed to reduce the binding above, compared with the control that was not through step 1 above.

The present invention also provides a method for screening a candidate material for the diagnosis, prevention, or treatment of one or more HRF-related diseases selected from the group consisting of allergic diseases, inflammatory diseases, and malaria, comprising the following steps:

1) contacting one or more materials selected from the group consisting of FL domain and H2 domain of HRF, their analogues, and their fragments with the test sample together with the cells expressing the HRF receptor;

2) culturing the cells of step 1) above; and 3) selecting the test sample demonstrating the low secretion of the active material including histamine, IL-8, or GM-CSF in the culture solution of step 2), compared with the level of the control that was not through the step 1) above.

The present invention also provides a method for screening a candidate material for the treatment of HRF-related disease selected from the group consisting of allergic diseases, inflammatory diseases, and malaria, by the following steps of: constructing an antibody binding one or more materials selected from the group consisting of FL domain, H2 domain, and HRF C-terminus domain; treating the test sample with the above; and selecting the test sample that was confirmed to increase the binding strength between the antibody above and the FL domain, H2 domain, and C-terminus domain, compared with that of the control.

The present invention also provides a method for screening a candidate material for the treatment of HRF-related disease selected from the group consisting of allergic diseases, inflammatory diseases, and malaria, comprising the steps of measuring the expression of HRF containing the FL, H2, and C-terminus domains; and selecting the test sample that was confirmed to reduce the HRF expression, compared with that of the control.

The present invention also provides a method for diagnosing HRF-related disease selected from the group consisting of allergic diseases, inflammatory diseases, and malaria, comprising the steps of measuring the binding strength using the antibody binding one or more materials selected from the group consisting of FL domain, H2 domain, and C-terminus domain of HRF between FL domain or H2 domain, and HRF receptor or measuring the activity of the receptor; and selecting the test sample that was confirmed to increase the binding strength, compared with the control.

The present invention also provides a kit for the diagnosis of allergic disease, inflammatory disease, or malaria, comprising a material that can detect the binding between one or more materials selected from the group consisting of HRF FL domain, H2 domain, and C-terminus domain, the analogues thereof, and the fragments thereof and the HRF receptor.

The present invention also provides FL domain characteristically binding to HRF receptor or involved in the binding to HRF receptor, H2 domain characteristically binding to HRF receptor or involved in the binding to HRF receptor, and C-terminus domain involved in the binding to HRF receptor or in the activation of HRF or in the formation of HRF dimer.

The present invention also provides a gene encoding one or more materials selected from the group consisting of FL domain, H2 domain, and C-terminus domain; a recombinant expression vector containing the said gene; and a transformant transfected with the said expression vector.

The present invention also provides a peptide, an antibody, the analogues thereof, or the immunologically active fragments thereof which specifically bind to the FL domain above.

The present invention also provides a peptide, an antibody, the analogues thereof, or the immunologically active fragments thereof which specifically bind to the H2 domain above.

The present invention also provides a peptide, an antibody, the analogues thereof, or the immunologically active fragments thereof which specifically bind to the HRF C-terminus domain above.

The present invention also provides a histamine releasing inducer comprising one or more materials selected from the group consisting of HRF, FL domain, H2 domain, and C-terminus domain as an active ingredient.

The present invention also provides a method for preparing a peptide or an antibody against FL domain, the analogues thereof, or the immunologically active fragment thereof comprising the following steps:

1) producing a FL domain specific peptide or antibody, the analogues thereof, or the immunologically active fragment thereof by inducing the immune response by using the FL domain peptide composed of the amino acid sequence selected from the group consisting of the amino acid sequences represented by SEQ. ID. NO: 1~NO: 4 as an antigen in an animal model except human;

2) confirming whether or not the peptide, the antibody, the analogues thereof, or the immunologically active fragment thereof produced in step 1) above could specifically bind to the antigen; and 3) separating and purifying the peptide, the antibody, the analogues thereof, or the immunologically active fragment thereof confirmed to bind specifically to the antigen in step 2).

The present invention also provides a method for preparing a peptide or an antibody against H2 domain, the analogues thereof, or the immunologically active fragment thereof comprising the following steps:

1) producing a H2 domain specific peptide or antibody, the analogues thereof, or the immunologically active fragment thereof by inducing the immune response by using the H2 domain peptide composed of the amino acid sequence selected from the group consisting of the amino acid sequences represented by SEQ. ID. NO: 11~NO: 12 as an antigen in an animal model except human;

2) confirming whether or not the peptide, the antibody, the analogues thereof, or the immunologically active fragment thereof produced in step 1) above could specifically bind to the antigen; and 3) separating and purifying the peptide, the antibody, the analogues thereof, or the immunologically active fragment thereof confirmed to bind specifically to the antigen in step 2).

The present invention also provides a method for preparing a peptide or an antibody against HRF C-terminus domain, the analogues thereof, or the immunologically active fragment thereof comprising the following steps:

1) producing a HRF C-terminus domain specific peptide or antibody, the analogues thereof, or the immunologically active fragment thereof by inducing the immune response by using the HRF C-terminus domain peptide as an antigen in an animal model except human;

2) confirming whether or not the peptide, the antibody, the analogues thereof, or the immunologically active fragment thereof produced in step 1) above could specifically bind to the antigen; and 3) separating and purifying the peptide, the antibody, the analogues thereof, or the immunologically active fragment thereof confirmed to bind specifically to the antigen in step 2).

The present invention also provides a method for identifying a HRF-specific receptor containing the step of performing the protein-protein interaction analysis.

Advantageous Effect

The present inventors confirmed FL domain and H2 domain that could bind to HRF receptor existing in the cell membrane as a structural part of IgE-dependent histamine releasing factor (HRF) of the invention, and also confirmed C-terminus domain of HRF is involved in the binding to the receptor or the activation of HRF. The present inventors confirmed further that the FL and H2 domains could inhibit IL-8 secretion by binding to HRF receptor. Therefore, the FL domain, H2 domain, and C-terminus domain of HRF binding to HRF receptor can be effectively used for the development of an agent for the diagnosis, prevention, and treatment of HRF-related diseases including allergic diseases such as asthma, bronchitis, chronic obstructive pulmonary disease, bronchiectasis, rhinitis, atopic dermatitis, hives (urticaria), hay fever, conjunctivitis, and anaphylaxis; inflammatory diseases such as bronchitis, pneumonia, arthritis, nephritis, psoriasis, dermatitis, Crohn's disease, enteritis, gingivitis, arteriosclerosis, coronary arteritis, hepatitis, Behcet's disease, bladder cancer, prostatitis, pyelonephritis, glomerulonephritis, osteomyelitis, thyroiditis, uveitis, abdominal cavity inflammation, meningitis, pulmonary fibrosis and rheumatoid arthritis; and malaria.

BRIEF DESCRIPTION OF THE DRAWINGS

The application of the preferred embodiments of the present invention is best understood with reference to the accompanying drawings, wherein.

DESCRIPTION OF THE PREFERRED EMBODIMENTS

Figure 1:
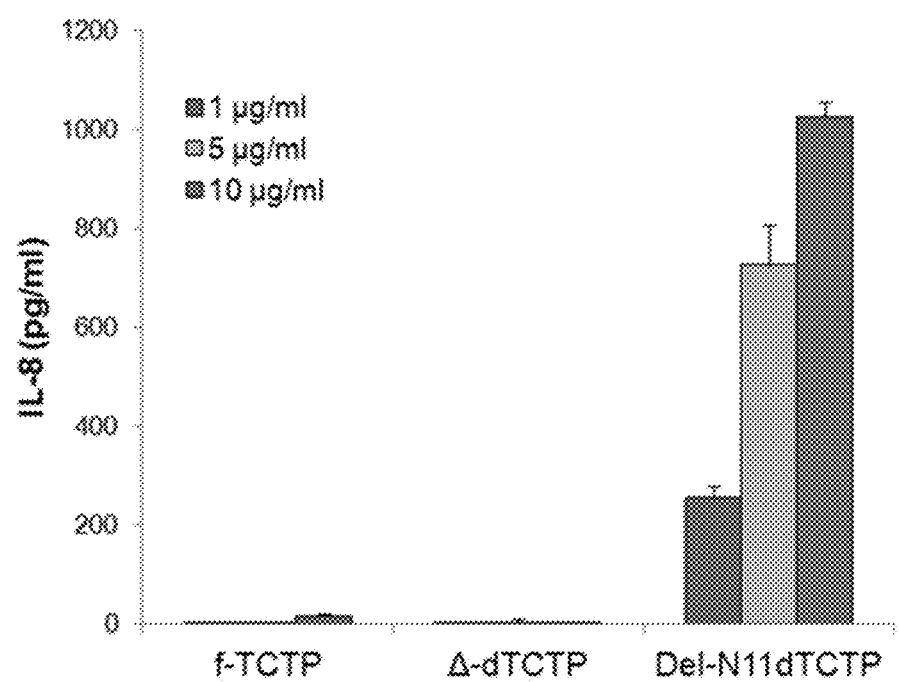
FIG. 1 is a graph illustrating the comparison of IL-8 inducing ability of f-TCTP (monomer TCTP), Δ-dTCTP (FL deleted dimer TCTP), and Del-N11dTCTP (N-terminus deleted dimer TCTP, HRF) according to the treatment at various concentrations in BEAS-2B cells.

Hereinafter, the present invention is described in detail.

The present invention provides a pharmaceutical composition for the diagnosis, prevention or treatment of one or more diseases selected from the group consisting of allergic diseases, inflammatory diseases, and malaria, comprising the binding inhibitor between IgE-dependent histamine releasing factor (HRF) and its receptor existing in the cell membrane as an active ingredient.

TCTP is a unique protein that is secreted out of the cell through an atypical pathway after staying in the small secretory vesicles. It has been reported that TSAP6, the p53-inducible membrane protein, is involved in this process (Amzallag et al., *J Biol Chem*, 279, 46104-46112, 2004). The secreted HRF stimulates IgE-sensitized basophils to promote histamine and interleukin-4 (IL-4) release, resulting in late phase allergic diseases such as allergic rhinitis, asthma and atopic dermatitis (MacDonald et al., *Science*, 269, 688-690, 1995).

The allergic disease herein is preferably selected from the group consisting of asthma, bronchitis, chronic obstructive pulmonary disease, bronchiectasis, rhinitis, atopic dermatitis, hives (urticaria), hay fever, conjunctivitis, and anaphylaxis, and more preferably asthma, rhinitis, or atopic dermatitis, but not always limited thereto.

The inflammatory disease herein is preferably selected from the group consisting of rheumatoid arthritis, bronchitis, pneumonia, arthritis, nephritis, psoriasis, dermatitis, Crohn's disease, enteritis, gingivitis, arteriosclerosis, coronary arteritis, hepatitis, Behcet's disease, bladder cancer, prostatitis, pyelonephritis, glomerulonephritis, osteomyelitis, thyroiditis, uveitis, abdominal cavity inflammation, meningitis, and pulmonary fibrosis, and more preferably rheumatoid arthritis, but not always limited thereto.

IL-8 which can be upregulated by HRF is involved in various allergic diseases preferably exemplified by asthma or bronchitis (Chanez et al., *Int Arch Allergy Immunol*, 111, 83-88, 1996), chronic obstructive pulmonary disease (Nocker et al., *Int Arch Allergy Immunol*, 109, 183-191, 1996), bronchiectasis (Simpson et al., *Thorax*, 62, 211-218, 2007), rhinitis (Benson et al., *Pediatr Allergy Immunol*, 10, 178-185, 1999; Kuna et al., *J Allergy Clin Immun*, 97, 104-112, 1996), atopic dermatitis (Kimata & Lindley, *Arch Dis Child* 70, 119-122, 1994), hives (urticaria, Choi et al., *J Clin Immunol*, 28, 244-249, 2008), hay fever (Ciprandi et al., *Otolaryngol Head Neck Surg*, 133, 429-435, 2005), conjunctivitis (Miyoshi et al., *Cornea*, 20, 743-747, 2001), and anaphylaxis, but not always limited thereto.

IL-8 is involved in various inflammatory diseases preferably exemplified by chronic inflammatory bronchial disease such as chronic bronchitis (Richman-Eisenstat et al., *Am J Physiol*, 264, L413-418, 1993), inflammatory lung disease such as pneumonia (Erger and Casale, *Eur Respir J*, 11, 299-305, 1998; Pease & Sabroe, *Am J Respir Med*, 1, 19-25, 2002), arthritis or nephritis (Harada et al., *J Leukoc Biol*, 56, 559-564, 1994), psoriasis (Schulz et al., *J Immunol*, 151, 4399-4406, 1993; Bruch-Gerharz et al., *J Exp Med*, 184, 2007-2012, 1996), dermatitis (Sticherling et al., *Arch Dermatol Res*, 284, 82-85, 1992), Crohn's disease (Izutani et al., *Inflamm Bowel Dis*, 1, 37-47, 1995), inflammatory bowel disease (Mitsuyama et al., *Clin Exp Immunol*, 96, 432-436, 1994), gingivitis (Haake & Huang, Clinical Periodontology, 9th Edition. Philadelphia: W. B. Saunders Co. 2002. page 162), cardiovascular disease such as arteriosclerosis and coronary artery disease (Apostolakis et al., *Cardiovasc Res*, 84, 353-360, 2009; Boekholdt et al., *Arterioscler Thromb Vasc Biol*, 24, 1503-1508, 2004), chronic liver disease (Zimmermann et al., *PLoS ONE*, 6, e21381, 2011), Behcet's disease (Katsantonis et al., *Dermatology*, 201, 37-39, 2000), bladder cancer, prostatitis, pyelonephritis or osteomyelitis (Shahzad et al., *Int arch med*, 3, 11, 2010), thyroid disease (Kobawala et al., *J Thyroid Res*, 8, 270149, 2011), uveitis (Klok et al., *Br J Ophthalmol*, 82, 871-874, 1998), glomerulonephritis, peritonitis, meningitis, and pulmonary fibrosis (Harada et al., *Mol Med Today*, 2, 482-489, 1996), but not always limited thereto. Therefore, using the IL-8 inhibitor was proposed as an efficient strategy to treat such diseases as lung disease, rheumatoid arthritis, inflammatory bowel disease, chronic inflammatory skin disease such as psoriasis and palmoplantar pustulosis, other inflammatory disease such as ocular inflammation (Mukaida, *Am J Physiol Lung Cell Mol Physiol*, 284, L566-L577, 2003; Skov et al., *J Immunol*, 181, 669-679, 2008; Harada et al., *J Leukoc Biol*, 56, 559-564, 1994). IL-8 blocking antibody or suppression of the gene encoding IL-8 receptor is also effective in treating inflammation (Harada et al., *Mol Med Today*, 2, 482-489, 1996). For example, inflammation was reduced by administering an antibody to IL-8 in patients with chronic inflammatory skin disease (Skov et al., *J Immunol*, 181, 669-679, 2008). GM-CSF which is up-regulated by HRF is also involved in various inflammatory diseases (Hamilton, *Trends Immunol*, 23, 403-408, 2002), so GM-CSF is also proposed as a target for the treatment of inflammatory disease including rheumatoid arthritis (Cornish et al., *Nat Rev Rheumatol*, 5, 554-559, 2009). The present inventors confirmed that the HRF receptor binding inhibitor was involved in the inhibition of IL-8 secretion, suggesting that the HRF receptor-binding inhibitor of the invention can be useful for the prevention and treatment of the disease said above.

It was disclosed in 1998 that artemisinin, the antimalarial agent, binds to the malarial protein HRF (Bhisutthibhan et al., *J Biol Chem*, 273, 16192-16198, 1998). IL-8 is also secreted in patients with malaria (Friedland et al., *Trans R Soc Trop Med Hyg*, 87, 54-55, 1993), and malarial HRF accelerates IL-8 secretion, according to the previous reports (MacDonald et al., *Proc Natl Acad Sci USA*, 98, 10829-32, 2001). Therefore, by inhibiting receptor binding of HRF to suppress HRF activity, the HRF receptor binding inhibitor of the present invention can be advantageously used for the prevention and treatment of malaria just like artemicinin.

TCTP (Translationally Controlled Tumor Protein) dimer is the active form. Among the structures of the TCTP dimer form HRF, flexible loop (FL) domain or helix 2 (H2) domain is the region for the binding with HRF receptor. TCTP herein is preferably derived from the natural origins or prepared by artificial production which is either full length or has the deletion of flexible loop (FL), the deletion of helix 2 (H2), the deletion of C-terminus, or the deletion of N-terminus.

The said TCTP dimer form HRF is a dimer form of either full length or deleted forms of FL, H2, N-terminus or C-terminus, or can be homologous or heterologous.

The said TCTP dimer form HRF can be derived from a vertebrate.

The binding inhibitor can be functioning to inhibit the binding between HRF receptor and one or both of flexible loop (FL) domain and helix 2 (H2) domain.

In the TCTP dimer form HRF structure, flexible loop (FL) domain can bind to the HRF receptor existing in the cell membrane as an intrinsically unfolded protein (IUP) structural part, but not always limited thereto.

The said FL domain preferably contains one of the followings: the amino acid sequence of (X)n-(S or T)-RTEG-(A, N, or Q)-IDDSLIGGNASAEGPEGEGTE-(S or A)-TV-(V or I)-T-(X)n (SEQ ID NO: 38), the analogues thereof, and the fragments thereof, wherein X is a random amino acid and n is an integer of 0~5.

The said FL domain preferably contains one of the followings: the amino acid sequences represented by SEQ. ID. NO: 1~NO: 4 as listed in Table 1, the analogues thereof, and the fragments thereof.

The FL domain above can be encoded by the gene encoding itself.

The FL domain above can be encoded by any DNA of the followings; the nucleotide sequences represented by SEQ. ID. NO: 5~NO: 10 as listed in Table 1, the analogues thereof, and the fragments thereof.

The said TCTP dimer form HRF can have helix 2 (H2) domain binding to the HRF receptor existing in the cell membrane.

The said H2 domain preferably contains one of the followings: the amino acid sequence of (X)n-TKE-(A or S)-YKKYIKDYMK-(S or A)-(L or I)-K-(G or A)-(K or R)-LEE-(Q or H)-(K or R)-P-(X)n (SEQ ID NO: 39), the analogues thereof, and the fragments thereof, wherein X is a random amino acid and n is an integer of 0~5.

The said H2 domain preferably contains one of the followings: the amino acid sequences represented by SEQ. ID. NO: 11~NO: 12 as listed in Table 1, the analogues thereof, and the fragments thereof.

The H2 domain above can be encoded by the gene encoding itself.

The H2 domain above can be encoded by one of the followings; the nucleotide sequences represented by SEQ. ID. NO: 13~NO: 15, the analogues thereof, and the fragments thereof.

The said C-terminus domain is preferably composed of one of the followings: one of the amino acid sequences represented by SEQ. ID. NO: 33~NO: 34, the analogues thereof, and the fragments thereof, wherein the amino acid sequence can have substitution, deletion, or addition of one or more amino acids.

The C-terminus domain above can be encoded by the gene encoding itself.

The C-terminus domain above can be encoded by one of the followings; the nucleotide sequences represented by SEQ. ID. NO: 35~NO: 37, the analogues thereof, and the fragments thereof. The said C-terminus domain is preferably composed of one of the followings: one of the amino acid sequences represented by SEQ. ID. NO: 33~NO: 34, the analogues thereof, and the fragments thereof, wherein the amino acid sequence can have substitution, deletion, or addition of one or more amino acids.

TABLE 1

| Domain | SEQ ID. NO | Species | Sequence |
|---|---|---|---|
| FL amino acid sequence | | | |
| FL (37-68) | 1 | Rat Mouse | SRTEGAIDDSLIGGNASAEGPEG EGTESTVVT |
| | 2 | Human | SRTEGNIDDSLIGGNASAEGPEG EGTESTVIT |
| FL (38-66) | 3 | Rat Mouse | RTEGAIDDSLIGGNASAEGPEGE GTESTV |
| | 4 | Human | RTEGNIDDSLIGGNASAEGPEGE GTESTV |
| FL DNA sequence | | | |
| FL (37-68) | 5 | Rat | agt aga aca gag ggt gcc atc gat gat tca ctc att ccg gag ggc gaa tcc gct gaa ggt ccg gag ggc gaa ggt acc gaa agc aca gta gtc acc |

TABLE 1-continued

| Domain | SEQ ID. NO | Species | Sequence |
|---|---|---|---|
| | 6 | Mouse | agt aga aca gag ggt gcc atc gat gac tcg ctc atc ggt gga aat gct tcc gct gaa ggt ccg gag ggc gaa ggt acc gaa agc aca gta gtc acc |
| | 7 | Human | agt agg aca gaa ggt aac att gat gac tcg ctc att ggt gga aat gcc tcc gct gaa ggc ccc gag ggc gaa ggt acc gaa agc aca gta atc act |
| FL (38-66) | 8 | Rat | aga aca gag ggt gcc atc gat gat tca ctc att ggt gga aat gct tcc gct gaa ggt ccg gag ggc gaa ggt acc gaa agc aca gta |
| | 9 | Mouse | aga aca gag ggt gcc atc gat gac tcg ctc atc ggt gga aat gct tcc gct gaa ggt ccg gag ggc gaa ggt acc gaa agc aca gta |
| | 10 | Human | agg aca gaa ggt aac att gat gac tcg ctc att ggt gga aat gcc tcc gct gaa ggc ccc gag ggc gaa ggt acc gaa agc aca gta |

| H2 amino acid sequence | | | |
|---|---|---|---|
| H2 (84-108) | 11 | Rat Mouse | TKEAYKKYIKDYMKSLKGKLEEQ KP |
| | 12 | Human | TKEAYKKYIKDYMKSIKGKLEEQ RP |

| H2 DNA sequence | | | |
|---|---|---|---|
| H2 (84-108) | 13 | Rat | aca aaa gag gcc tac aaa aag tat atc aaa gac tac atg aaa tca ctc aag ggc aaa ctt gaa gaa cag aaa cca |
| | 14 | Mouse | aca aaa gag gct tac aaa aag tac atc aaa gac tac atg aaa tca ctc aaa ggc aaa ctt gaa gag cag aaa cca |
| | 15 | Human | aca aaa gaa gcc tac aag aag tac atc aaa gat tac atg aaa tca atc aaa ggg aaa ctt gaa gaa cag aga cca |

| C-terminus amino acid sequence | | | |
|---|---|---|---|
| C-terminus (162-172) | 33 | Rat Mouse | FFKDGLEMEKC |
| | 34 | Human | FFKDGLKMEKC |

TABLE 1-continued

| Domain | SEQ ID. NO | Species | Sequence |
|---|---|---|---|
| C-terminus DNA sequence | | | |
| C-terminus (162-172) | 35 | Rat | ttc ttt aag gag ggc tta gag atg gaa aaa tgt |
| | 36 | Mouse | ttc ttt aag gat ggc tta gag atg gag aaa tgt |
| | 37 | Human | ttc ttt aag gat ggt tta aaa atg gaa aaa tgt |

The amino acid sequence of FL domain, H2 domain, or C-terminus domain can be modified by the conventional method known to those in the art. For example, the number of amino acids in FL domain, H2 domain, or C-terminus domain can be increased or decreased. Also modification can be made by changing the order or a specific residue in the amino acid sequence above as long as the activity of FL domain, H2 domain, or C-terminus domain is not reduced. The amino acid can be changed into not only natural L-α-amino acid but also β, γ, δ amino acid as well as D-α-amino acid derivatives.

Therefore, those who are in this field can modify the FL, H2 domain or C-terminus domain using the conventional techniques as long as the HRF inhibitory activity thereof is maintained, increased, or not reduced. In that case, the modified one is also included in the scope of the present invention.

The said FL domain, H2 domain, and C-terminus domain can be derived from a vertebrate.

Since the HRF receptor binding domain and the mechanism of the same has been disclosed by the present invention, anyone who has knowledge of this field can easily identify FL domain, H2 domain, and C-terminus domain in rats, mice, humans, rabbits, and chickens. Thus, the HRF receptor binding domains of rats, mice, humans, rabbits, and chickens are also included in the scope of the present invention.

The full-length amino acid sequence of TCTP is highly conserved in various eukaryotes, which was confirmed by sequence alignment (Thaw et al., *Nat Struct Biol,* 8, 701-704, 2001). The 3-dimensional structure also has a high similarity (Hinojosa-Moya et al., *J Mol Evol,* 66, 472-483, 2008). Therefore, not only the full-length sequence of TCTP but also the receptor binding domains FL, H2, and C-terminus are highly homologous in vertebrates, so that they can be played equally in the receptor binding, dimer formation, or as sites for activation.

The binding inhibitor above binds specifically to the domain involved in binding to HRF receptor, and is preferably functioning to inhibit the binding between HRF and its receptor, to inhibit receptor activity, or to inhibit dimer formation.

The binding inhibitor above binds to one or more of the followings: HRF FL domain, H2 domain, and C-terminus domain, and can inhibit the binding between either or both of FL domain or H2 domain and HRF receptor.

The binding inhibitor above can include one or more materials selected from the group consisting of antibodies against one or more of the followings: HRF FL domain, H2 domain, and C-terminus domain, and the fragments of the same.

The binding inhibitor above can be the antibody or the fragments thereof recognizing the amino acid sequence (X)n-(S or T)-RTEG-(A, N or Q)-IDDSLIGGNASAEG-PEGEGTE-(S or A)-TV-(V or I)-T-(X)n (SEQ ID NO: 38), the analogues thereof, or the fragments thereof, but not always limited thereto and any antibody that can recognize FL domain can be accepted. Herein, X is a random amino acid and n is an integer of 0~5.

The binding inhibitor above can be the antibody or the fragments thereof recognizing the amino acid sequence (X)n-TKE-(A or S)-YKKYIKDYMK-(S or A)-(L or I)-K-(G or A)-(K or R)-LEE-(Q or H)-(K or R)-P-(X)n (SEQ ID NO: 39), the analogues thereof, or the fragments thereof, but not always limited thereto and any antibody that can recognize H2 domain can be accepted. Herein, X is a random amino acid and n is an integer of 0~5.

The binding inhibitor above can be the antibody or the fragments thereof recognizing the amino acid sequence represented by SEQ. ID. NO: 33 or NO: 34, the analogues thereof, or the fragments thereof, or the fragments of the same, wherein the amino acid sequence can have substitution, deletion, or addition of one or more amino acids in the sequence, but not always limited thereto and any antibody that can recognize HRF C-terminus domain can be accepted.

The binding inhibitor above binds to HRF receptor to suppress the function of HRF. The C-terminus domain preferably inhibits the TCTP dimer formation or the HRF or HRF receptor activation.

The inhibition of HRF function in this invention preferably results in the inhibition of the secretion of granulocyte-macrophage colony-stimulating factor, the secretion of IL-8, and the oxidative stress activity.

The binding inhibitor above can inhibit the HRF receptor competitively, non-competitively, or uncompetitively.

The binding inhibitor above can include the HRF receptor binding inhibitor comprising one or more materials selected from the group consisting of HRF FL domain, H2 domain, C-terminus domain, the analogues thereof, and the fragments thereof, as an active ingredient.

The binding inhibitor above can include one or more materials selected from the group consisting of HRF FL domain, H2 domain, C-terminus domain, the analogues thereof, and the fragments thereof.

The FL domain comprising one of the amino acid sequences represented by SEQ. ID. NO: 1~NO: 4 can play as the binding inhibitor between the IgE-dependent histamine releasing factor (HRF) and the HRF receptor existing in the cell membrane.

The H2 domain comprising the amino acid sequence represented by SEQ. ID. NO: 11 or NO: 12 can play as the binding inhibitor above.

The C-terminus domain comprising the amino acid sequence represented by SEQ. ID. NO: 33 or NO: 34 can play as the binding inhibitor above.

Also, the fusion protein conjugated with the FL domain, H2 domain, or C-terminus domain above and HRF domain can play as the binding inhibitor above.

The FL domain, H2 domain, and C-terminus domain having the combination of various sequences of the said FL domain, H2 domain, and C-terminus domain above can also be functioning as the binding inhibitor.

The binding inhibitor can include the similar sequence or the fragments of the same having the homology with the FL domain, H2 domain, and C-terminus domain above.

The binding inhibitor above preferably contains one of the followings: the amino acid sequence of (X)n-(S or T)-RTEG-(A, N or Q)-IDDSLIGGNASAEGPEGEGTE-(S or A)-TV-(V or I)-T-(X)n (SEQ ID NO: 38), the analogues thereof, and the fragments thereof, wherein X is a random amino acid and n is an integer of 0~5.

The binding inhibitor above can include one of the amino acid sequences represented by SEQ. ID. NO: 1~NO: 4 listed in Table 1, the analogues thereof, and the fragments thereof.

The binding inhibitor above preferably contains one of the followings: the amino acid sequence of (X)n-TKE-(A or S)-YKKYIKDYMK-(S or A)-(L or I)-K-(G or A)-(K or R)-LEE-(Q or H)-(K or R)-P-(X)n (SEQ ID NO: 39), the analogues thereof, and the fragments thereof, wherein X is a random amino acid and n is an integer of 0~5.

The binding inhibitor is preferably composed of one of the materials selected from the group consisting of the amino acid sequences represented by SEQ. ID. NO: 11~NO: 12 listed in Table 1, the analogues thereof, and the fragments thereof.

The binding inhibitor is preferably composed of one of the followings: one of the amino acid sequences represented by SEQ. ID. NO: 33~NO: 34, the analogues thereof, and the fragments thereof, wherein the amino acid sequence can have substitution, deletion, or addition of one or more amino acids.

The binding inhibitor above can include the expression inhibitor suppressing the expression of one or more materials selected from the group consisting of FL domain, H2 domain, C-terminus domain, and HRF as an active ingredient.

The expression inhibitor suppressing the expression of one or more materials selected from the group consisting of FL domain, H2 domain, C-terminus domain, and HRF can be selected from the group consisting of antisense nucleotide binding to FL domain, H2 domain, FL and H2 domains, C-terminus domain, or HRF mRNA, short interfering RNA, short hairpin RNA, and small interfering RNA (siRNA).

The binding inhibitor above can include the antibody specifically binding to HRF C-terminus domain, the analogues thereof, or the immunologically active fragments thereof.

The binding inhibitor above can be the peptide composed of 7 amino acids, wherein the first amino acid is selected from the group consisting of A, L, and W, the second amino acid is selected from the group consisting of V, Y, E, and A, the third amino acid is selected from the group consisting of T, V, F, and A, the forth amino acid is selected from the group consisting of Y, P, and A, the fifth amino acid is selected from the group consisting of P, G, and K, the sixth amino acid is selected from the group consisting of A, L, S, and W, and the seventh amino acid is selected from the group consisting of A, P, and M, the analogues thereof, or the fragments thereof.

The binding inhibitor above can be a peptide composed of one of the amino acid sequences represented by SEQ. ID. NO: 23~NO: 32, the analogues thereof, or the fragments thereof.

The peptide composed of 7 amino acids or the analogues thereof can bind to HRF, and more preferably bind to HRF H2 domain.

The peptide composed of 7 amino acids above or the analogues thereof eventually prevent the secretion of an immune response inducing substance by inhibiting the binding between HRF and its receptor by binding itself to HRF.

In a preferred embodiment of the present invention, the effect of f-TCTP (monomer TCTP), Δ-dTCTP (FL deleted dimer TCTP), and Del-N11dTCTP (N-terminus deleted dimer TCTP, HRF) on the secretion of IL-8 and GM-CSF in BEAS-2B cells was investigated. To do so, the activities of f-TCTP, Δ-dTCTP, and Del-N11dTCTP were compared with the IL-8 secretion in BEAS-2B cells (ATCC). As a result, Del-N11dTCTP increased the secretion of IL-8 and GM-CSF more than f-TCTP and Δ-dTCTP could do (see FIGS. 1 and 2). Del-N11dTCTP demonstrated the ability to induce IL-8 secretion by forming an active dimer, while FL deleted Δ-dTCTP was confirmed to be inactive form that could not induce IL-8 secretion even though it formed a dimer. Therefore, it was confirmed that FL domain was involved in the TCTP dimer binding to its specific receptor, suggesting that it was an important part for cytokine secretion activity.

In a preferred embodiment of the present invention, affinity of f-TCTP, Δ-dTCTP, and Del-N11dTCTP to dTBP2 (dTCTP binding peptide 2) was investigated. Particularly, biotin was conjugated to COOH-terminal of dTBP2, which was purified and immobilized. Then, f-TCTP, Δ-dTCTP, and Del-N11dTCTP were added thereto, followed by investigation of binding strength. As a result, Del-N11dTCTP had higher affinity to dTBP2 than f-TCTP or Δ-dTCTP (see FIG. 3). Unlike Del-N11dTCTP, FL domain deleted Δ-dTCTP showed low affinity to dTBP2 peptide even though it could form a dimer. So, it was confirmed that FL domain played an important role in the binding process between dTBP2 and the active HRF form Del-N11dTCTP, and thus without FL domain, dTBP2 binding was inhibited even though a dimer was formed. In conclusion, FL domain binds to the receptor to cause structural change, by which HRF can bind to dTBP2.

In a preferred embodiment of the present invention, the present inventors further investigated whether or not FL domain, Helix 2 domain, and Helix 3 domain could inhibit the binding between Del-N11dTCTP and the receptor. To do so, peptides of each domain were synthesized and used to investigate the inhibition of Del-N11dTCTP. The peptides of FL domain, Helix 2 domain, and Helix 3 domain were synthesized with the acetylation of $NH_2$-terminus and the amidation of COOH-terminus, followed by purification (peptron). As a result, FL domain and Helix 2 domain inhibited IL-8 secretion better than Helix 3 domain (see FIG. 4).

In a preferred embodiment of the present invention, the IL-8 inhibition effect of the polyclonal antibody recognizing FL domain and Helix 2 domain was investigated. Particularly, BEAS-2B cells were treated with anti-FL antibody and anti-H2 antibody at different concentrations, followed by investigation of the suppression of IL-8 induced by Del-N11dTCTP. As a result, IL-8 secretion was not observed in the negative control (NC) group treated with the antibody alone. In the cells treated with Del-N11dTCTP alone, IL-8 secretion was increased. In the cells treated with the antibody specifically recognizing FL domain, IL-8 secretion by Del-N11dTCTP was reduced (see FIG. 5). In the cells treated with the antibody specifically recognizing H2 domain, IL-8 secretion by Del-N11dTCTP was also reduced, suggesting that the antibody of the invention had the inhibitory effect on IL-8 release (see FIG. 6).

In a preferred embodiment of the present invention, the present inventors performed modeling of TCTP receptor binding in the presence or absence of FL domain by X-ray structure crystallography. To do so, monomer form f-TCTP (containing FL domain) and Δ-TCTP (FL domain deleted) were prepared, followed by dimer formation to construct f-dTCTP and Δ-dTCTP. The structure was identified after crystallization.

In a preferred embodiment of the present invention, the monomer form f-TCTP (containing FL domain) protein was cloned and expressed in order to construct f-dTCTP (containing FL domain). The f-TCTP separated by using HisTrap column (see FIG. 7) was purified by ion-exchange chromatography using Hi-Trap Q column, followed by SDS-PAGE (see FIG. 8).

In a preferred embodiment of the present invention, the monomer form Δ-TCTP (FL domain deleted) protein was cloned and expressed in order to construct Δ-dTCTP (FL domain deleted). The Δ-TCTP separated by using HisTrap column (see FIG. 9) was purified by ion-exchange chromatography using Hi-Trap Q column, followed by SDS-PAGE (see FIG. 10).

In a preferred embodiment of the present invention, the present inventors induced the formation of a dimer of the f-TCTP and Δ-TCTP expressed and purified above by treating with tertiary butyl hydroperoxide. As a result, f-dTCTP and Δ-dTCTP proteins were obtained.

In a preferred embodiment of the present invention, the optimum condition for the preparation of f-dTCTP and Δ-dTCTP protein crystals was screened. Particularly, the crystallization was induced by hanging drop vapor diffusion method or sitting-drop vapor diffusion method. The stabilized cryo-condition was screened in order to collect information from synchrotron. X-ray data of the crystallized f-dTCTP and Δ-dTCTP proteins were collected in the stabilized cryo-condition. The crystal structure of f-dTCTP and Δ-dTCTP was investigated. As a result, the structure of the crystal structure was similar to that of the native TCTP used as the test model (see FIG. 11). The three-dimensional structure of the dimer form f-dTCTP and Δ-dTCTP was a symmetrical butterfly shape and the dimer structure was confirmed to be mediated by Cys172 (see FIG. 12).

In a preferred embodiment of the present invention, the present inventors performed modeling the structure of f-dTCTP containing FL domain because it was hard to determine the FL domain itself of f-dTCTP due to the flexibility of the loop thereof. Modeling of FL domain was performed with minimized energy. As a result, in the f-dTCTP structure conjugated with FL, FL was stand alone and apart from HRF main body, so that the whole HRF structure was not affected by the presence of FL (see FIG. 13). The inventors also constructed the binding model between f-dTCTP and its receptor and the binding model between f-dTCTP and dTBTP2 peptide (see FIG. 14).

In a preferred embodiment of the present invention, the present inventors produced specific polyclonal antibodies by inducing immune response in New Zealand White rabbits by using a HRF receptor binding domain peptide as an antigen in order to construct the antibody inhibiting HRF activity by binding specifically to FL domain, H2 domain, and C-terminus domain of HRF which are the regions binding to HRF receptor. It was investigated whether the produced antibody could bind specifically to the antigen. The inventors also separated and purified IgG binding to the receptor binding domains FL, H2, and C-terminus through antigen specific affinity chromatography (see FIG. 15 and Example 8), followed by examination of inhibitory effects on immune response-inducing material and anti-inflammatory effect thereof.

In addition, in another preferred embodiment of the present invention, the inventors separated 7-mer peptide that could bind to HRF through HRF affinity assay and analyzed the sequence of 7-mer peptide composed of 7 amino acids (see SEQ. ID. NO: 23~NO: 32). As a result, it was confirmed that the peptide above could bind to a specific region of HRF such as H2 domain to inhibit the binding between HRF and its receptor, and accordingly it could prevent the secretion of immune response-inducing materials.

The present inventors confirmed that FL domain, H2 domain, and C-terminus domain existing in the cell membrane as a part of HRF structure could bind HRF receptor and further identified the antibody binding to the above and 7-mer peptide binding to HRF. Therefore, the said domains FL, H2, and C-terminus, and the antibody thereof and the 7-mer peptide binding to HRF can be effectively used for the development of an agent for the diagnosis, prevention, and treatment of HRF-related diseases including allergic diseases such as asthma, bronchitis, chronic obstructive pulmonary disease, bronchiectasis, rhinitis, atopic dermatitis, hives (urticaria), hay fever, conjunctivitis, and anaphylaxis; inflammatory diseases such as bronchitis, pneumonia, arthritis, nephritis, psoriasis, dermatitis, Crohn's disease, enteritis, gingivitis, arteriosclerosis, coronary arteritis, hepatitis, Behcet's disease, bladder cancer, prostatitis, pyelonephritis, glomerulonephritis, osteomyelitis, thyroiditis, uveitis, abdominal cavity inflammation, meningitis, pulmonary fibrosis and rheumatoid arthritis; and malaria.

The composition of the present invention can include, in addition to the HRF receptor binding inhibitor, one or more effective ingredients having the same or similar function to the HRF receptor binding inhibitor.

The composition of the present invention can be administered orally or parenterally and the parenteral administration includes intraperitoneal injection, intrarectal injection, intradermal injection, subcutaneous injection, intravenous injection, intramuscular injection, intrauterine injection, intracerebrovascular injection, intrathoracic injection, intra-articular injection, epidural injection, intraspinal injection, intracardiac injection, intra-arterial injection, intraosseous injection, intranasal administration, intrarectal administration, intratracheal administration, transdermal administration, eye drop, and spray, but not always limited thereto. The composition of the invention can be used in general forms of pharmaceutical formulation.

The composition of the present invention can be administered alone or treated together with surgical operation, hormone therapy, chemo-therapy and biological regulators.

The effective dose of the composition is 0.0001~1000 mg/kg per day and preferably 0.001~10 mg/kg per day, and administration frequency is once a day or preferably a few times a day. The effective dose of the composition can be determined according to weight, age, gender, health condition, diet, administration time, administration method, excretion rate and severity of disease.

The composition of the present invention can be prepared for oral or parenteral administration by mixing with generally used diluents or excipients such as fillers, extenders, binders, wetting agents, disintegrating agents and surfactant. Formulations for parenteral administration are sterilized aqueous solutions, water-insoluble excipients, suspensions, emulsions, lyophilized preparations and suppositories, but not always limited thereto. Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerogelatin, etc.

The present invention also provides a method for preventing or treating HRF-related disease containing the step of administering a pharmaceutically effective dose of the compound comprising the binding inhibitor between HRF and its receptor as an active ingredient to a subject.

The disease herein can be selected from the group consisting of allergic diseases such as asthma, bronchitis, chronic obstructive pulmonary disease, bronchiectasis, rhinitis, atopic dermatitis, hives (urticaria), hay fever, conjunctivitis, and anaphylaxis; inflammatory diseases such as bronchitis, pneumonia, arthritis, nephritis, psoriasis, dermatitis, Crohn's disease, enteritis, gingivitis, arteriosclerosis, coronary arteritis, hepatitis, Behcet's disease, bladder cancer, prostatitis, pyelonephritis, glomerulonephritis, osteomyelitis, thyroiditis, uveitis, abdominal cavity inflammation, meningitis, pulmonary fibrosis and rheumatoid arthritis; and malaria, but not always limited thereto.

The pharmaceutically effective dose herein indicates 0.0001~1000 mg/kg, and more preferably 0.001~100 mg/kg, but not always limited thereto. The administration dose can be adjusted according to weight, age, gender, health condition, diet, administration period, administration method, removal rate, and severity of disease, etc.

The composition of the present invention can be administered orally or parenterally and the parenteral administration includes intraperitoneal injection, intrarectal injection, intradermal injection, subcutaneous injection, intravenous injection, intramuscular injection, intrauterine injection, intracerebrovascular injection, intrathoracic injection, intra-articular injection, epidural injection, intraspinal injection, intracardiac injection, intra-arterial injection, intraosseous injection, intranasal administration, intrarectal administration, intratracheal administration, transdermal administration, eye drop, and spray, but not always limited thereto. The composition of the invention can be used in general forms of pharmaceutical formulation.

The subject herein is selected from the group consisting of vertebrates including human, mammals, test animals such as rats, rabbits, guinea pigs, hamsters, dogs and cats, and apes such as chimpanzees and gorillas, but not always limited thereto.

The present invention confirmed that the flexible loop FL domain and H2 domain in the active HRF, TCTP dimer structure, were the regions binding specifically to the receptor thereof existing in the cell membrane. Therefore, the invention suggested that the binding inhibitor between HRF and its receptor targeting the above FL domain H2 domain can be effectively used for the development of HRF-related disease inhibitor, wherein the disease is exemplified by such allergic diseases as asthma, bronchitis, chronic obstructive pulmonary disease, bronchiectasis, rhinitis, atopic dermatitis, hives (urticaria), hay fever, conjunctivitis, and anaphylaxis; such inflammatory diseases as bronchitis, pneumonia, arthritis, nephritis, psoriasis, dermatitis, Crohn's disease, enteritis, gingivitis, arteriosclerosis, coronary arteritis, hepatitis, Behcet's disease, bladder cancer, prostatitis, pyelonephritis, glomerulonephritis, osteomyelitis, thyroiditis, uveitis, abdominal cavity inflammation, meningitis, pulmonary fibrosis and rheumatoid arthritis; and malaria.

The present invention also provides a method for screening a candidate material for the diagnosis, prevention, or treatment of one or more HRF-related diseases selected from the group consisting of allergic diseases, inflammatory diseases, and malaria, comprising the following steps:

1) contacting one or more materials selected from the group consisting of FL domain and H2 domain, both HRF FL domain and H2 domain, their analogues, and their fragments with the test sample together with the HRF receptor;

2) measuring the binding strength between the said domains, their analogues, or their fragments with the HRF receptor; and 3) selecting the test sample that was confirmed to reduce the binding above, compared with the control that was not through step 1 above.

The allergic disease herein is preferably selected from the group consisting of asthma, bronchitis, chronic obstructive pulmonary disease, bronchiectasis, rhinitis, atopic dermatitis, hives (urticaria), hay fever, conjunctivitis, and anaphylaxis, but not always limited thereto.

The inflammatory disease herein is preferably selected from the group consisting of rheumatoid arthritis, bronchitis, pneumonia, arthritis, nephritis, psoriasis, dermatitis, Crohn's disease, enteritis, gingivitis, arteriosclerosis, coronary arteritis, hepatitis, Behcet's disease, bladder cancer, prostatitis, pyelonephritis, glomerulonephritis, osteomyelitis, thyroiditis, uveitis, abdominal cavity inflammation, meningitis, and pulmonary fibrosis, but not always limited thereto.

The test sample of step 3) is preferably one or more materials selected from the group consisting of peptides, proteins, antibodies, non-peptide substances, synthetic substances, chemicals, nucleic acids, natural substances, natural compounds, semisynthetic substances, fermented products, cell extracts, plant extracts, animal tissue extracts, and plasma, but not always limited thereto.

The present invention also provides a method for screening a candidate material for the diagnosis, prevention, or treatment of one or more HRF-related diseases selected from the group consisting of allergic diseases, inflammatory diseases, and malaria, comprising the following steps:

1) contacting one or more materials selected from the group consisting of either or both FL domain and H2 domain, their analogues, and their fragments with the test sample together with the cells expressing the HRF receptor;

2) culturing the cells of step 1) above; and 3) selecting the test sample demonstrating the low secretion of the active material including histamine, IL-8, or GM-CSF in the culture solution of step 2), compared with the level of the control that was not through the step 1) above.

The allergic disease herein is preferably selected from the group consisting of asthma, bronchitis, chronic obstructive pulmonary disease, bronchiectasis, rhinitis, atopic dermatitis, hives (urticaria), hay fever, conjunctivitis, and anaphylaxis, but not always limited thereto.

The inflammatory disease herein is preferably selected from the group consisting of rheumatoid arthritis, bronchitis, pneumonia, arthritis, nephritis, psoriasis, dermatitis, Crohn's disease, enteritis, gingivitis, arteriosclerosis, coronary arteritis, hepatitis, Behcet's disease, bladder cancer, prostatitis, pyelonephritis, glomerulonephritis, osteomyelitis, thyroiditis, uveitis, abdominal cavity inflammation, meningitis, and pulmonary fibrosis, but not always limited thereto.

The test sample of step 3) is preferably one or more materials selected from the group consisting of peptides, proteins, antibodies, non-peptide substances, synthetic substances, chemicals, nucleic acids, natural substances, natural compounds, semisynthetic substances, fermented products, cell extracts, plant extracts, animal tissue extracts, and plasma, but not always limited thereto.

The present invention also provides a method for screening a candidate material for the treatment of HRF-related disease selected from the group consisting of allergic diseases, inflammatory diseases, and malaria, by the following steps of: constructing an antibody binding one or more materials selected from the group consisting of FL domain, H2 domain, and HRF C-terminus domain; treating the test sample with the above; and selecting the test sample that was confirmed to increase the binding strength between the antibody above and the FL domain, H2 domain, and C-terminus domain, compared with that of the control.

The present invention also provides a method for screening a candidate material for the treatment of HRF-related disease selected from the group consisting of allergic diseases, inflammatory diseases, and malaria, comprising the steps of: measuring the expression of HRF containing the FL, H2, and C-terminus domains; and selecting the test sample that was confirmed to reduce the HRF expression, compared with that of the control.

The present invention also provides a method for diagnosing HRF-related disease selected from the group consisting of allergic diseases, inflammatory diseases, and malaria, by the following steps of: measuring the binding strength between the antibody binding one or more materials selected from the group consisting of FL domain, H2 domain, and HRF C-terminus domain and FL domain, H2 domain, or HRF C-terminus domain; and selecting the test sample that was confirmed to increase the binding strength between the antibody above and the FL domain, H2 domain, and C-terminus domain, compared with that of the control.

Because the FL domain and H2 domain, in HRF structure that are responsible for the binding to its receptor existing in the cell membrane and can inhibit IL-8 secretion eventually by binding to the receptor, were identified in the present invention, accordingly the screening method using the HRF receptor binding domains can be applied to screen a treatment agent for various inflammatory diseases, allergic diseases, and malaria.

The present invention also provides a kit for diagnosing allergic disease, inflammatory disease, or malaria comprising a substance detecting the binding between one or more materials selected from the group consisting of HRF FL domain, H2 domain, C-terminus domain, their analogues, and their fragments and HRF receptor.

To examine the substance that can detect the binding between HFR receptor and one or both of HRF FL domain and H2 domain, the primer, prove, or antisense nucleotide specifically binding to the domains above can be used, but not always limited thereto.

The substance that can detect the binding between HRF receptor and one or both of HRF FL domain and H2 domain can be the domain specific antibody.

The kit for diagnosing of allergic disease, inflammatory disease, or malaria herein can be RT-PCR (reverse transcription polymerase chain reaction) kit, DNA chip kit, ELISA (enzyme-linked immunosorbent assay) kit, sandwich ELISA kit, protein chip kit, rapid kit, or MRM (multiple reaction monitoring) kit, but not always limited thereto, and any kit that is well-known to those in the art can be selected.

The kit for diagnosing HRF-related disease of the present invention can recognize FL domain or H2 domain, as a part of HRF structure, binding to HRF receptor existing in the cell membrane, recognizes C-terminus domain involved in the activation of HRF or the receptor, and also be able to confirm the inhibition of IL-8 secretion by binding the FL or H2 domain to HRF receptor. Therefore, the kit using HRF receptor binding domain can be effectively used as a disease diagnostic kit for the diagnosis of various inflammatory diseases, allergic diseases, and malaria.

The present invention also provides an antibody or the immunologically active fragment thereof binding specifically to FL domain composed of one of the amino acid sequences represented by SEQ. ID. NO: 1~NO: 4

The present invention also provides an antibody or the immunologically active fragment thereof binding specifically to H2 domain composed of one of the amino acid sequences represented by SEQ. ID. NO: 11~NO: 12.

The present invention also provides an antibody or the immunologically active fragment thereof binding specifically to C-terminus domain composed of one of the amino acid sequences represented by SEQ. ID. NO: 33~NO: 34.

The antibody herein is preferably selected from the group consisting of polyclonal antibodies, monoclonal antibodies, murine antibodies, chimeric antibodies, and humanized antibodies, but not always limited thereto.

The polyclonal antibody herein can be produced by the conventional method composed of the steps of: injecting one of the protein markers of the invention to a test animal; and extracting blood from the animal to obtain serum containing the antibody. The polyclonal antibody can be purified by any well known methods in this field, and can be produced from such a host as goat, rabbit, sheep, monkey, horse, pig, cow, and dog.

The monoclonal antibody herein can be produced by any conventional technique to provide an antibody molecule through a serial cell culture, which is exemplified by hybridoma technique, Human-B-cell hybridoma technique, and EBV-hybridoma technique (Kohler G et al., Nature 256:495-497, 1975; Kozbor D et al., J Immunol Methods 81:31-42, 1985; Cote R J et al., Proc Natl Acad Sci 80:2026-2030, 1983; and Cole S P et al., Mol Cell Biol 62:109-120, 1984), but not always limited thereto.

The chimeric antibody herein can include such antibodies wherein a variable region sequence is originated from one species, a variable region sequence is originated from a mouse antibody, a constant region is originated from a human antibody, and a constant region sequence is originated from another species.

The humanized antibody herein can include the antibody wherein CDR sequence originated from mouse or other mammalian germline is conjugated to human framework region. The additional modification of the framework region can be made not only in the CDR sequence originated from a mammalian germline but also in the human framework sequence.

The immunologically active fragment herein is preferably selected from the group consisting of Fab, Fab', F(ab')$_2$, Fv, Fd, single chain Fv (scFv), and disulfide stabilized Fv (dsFv), but not always limited thereto.

The present invention also provides a FL domain characteristically binding to HRF receptor or involved in the HRF binding to its receptor. The said FL domain preferably contains one of the followings; the amino acid sequence of (X)n-(S or T)-RTEG-(A, N or Q)-IDDSLIGGNASAEG-PEGEGTE-(S or A)-TV-(V or I)-T-(X)n (SEQ ID NO: 38), the analogues thereof, and the fragments thereof.

The present invention also provides a H2 domain characteristically binding to HRF receptor or involved in the HRF binding to its receptor. The said H2 domain is preferably contains one of the followings; the amino acid sequence of (X)n-TKE-(A or S)-YKKYIKDYMK-(S or A)-(L or I)-K-(G or A)-(K or R)-LEE-(Q or H)-(K or R)-P-(X)n (SEQ ID NO: 39), the analogues thereof, and the fragments thereof.

The present invention also provides a C-terminus domain involved in the binding of HRF to HRF receptor, the activation of HRF, or the formation of HRF dimer. The C-terminus domain herein preferably contains one of the followings; the amino acid sequences represented by SEQ. ID. NO: 33~NO: 34, the analogues thereof, and the fragments thereof, wherein the amino acid sequence can have substitution, deletion, or addition of one or more amino acids therein.

The present invention also provides a gene encoding one or more materials selected from the group consisting of FL domain, H2 domain, and C-terminus domain; a recombinant expression vector containing the said gene; and a transformant transfected with the said expression vector.

The present invention also provides a peptide, an antibody, the analogues thereof, or the immunologically active fragments thereof which specifically bind to the FL domain, H2 domain, or C-terminus domain above.

The present invention also provides a histamine releasing inducer comprising one or more materials selected from the group consisting of FL domain, H2 domain, and C-terminus domain as an active ingredient.

The present invention also provides a method for preparing a peptide or an antibody against FL domain, the analogues thereof, or the immunologically active fragment thereof comprising the following steps:

1) producing a FL domain specific peptide or antibody, the analogues thereof, or the immunologically active fragment thereof by inducing the immune response by using the FL domain peptide composed of the amino acid sequence selected from the group consisting of the amino acid sequences represented by SEQ. ID. NO: 1~NO: 4 as an antigen in an animal model except human;

2) confirming whether or not the peptide, the antibody, the analogues thereof, or the immunologically active fragment thereof produced in step 1) above could specifically bind to the antigen; and 3) separating and purifying the peptide, the antibody, the analogues thereof, or the immunologically active fragment thereof confirmed to bind specifically to the antigen in step 2).

The present invention also provides a method for preparing a peptide or an antibody against H2 domain, the analogues thereof, or the immunologically active fragment thereof comprising the following steps:

1) producing a H2 domain specific peptide or antibody, the analogues thereof, or the immunologically active fragment thereof by inducing the immune response by using the H2 domain peptide composed of the amino acid sequence selected from the group consisting of the amino acid sequences represented by SEQ. ID. NO: 11~NO: 12 as an antigen in an animal model except human;

2) confirming whether or not the peptide, the antibody, the analogues thereof, or the immunologically active fragment thereof produced in step 1) above could specifically bind to the antigen; and 3) separating and purifying the peptide, the antibody, the analogues thereof, or the immunologically active fragment thereof confirmed to bind specifically to the antigen in step 2).

The present invention also provides a method for preparing a peptide or an antibody against C-terminus domain of HRF, the analogues thereof, or the immunologically active fragment thereof comprising the following steps:

1) producing a HRF C-terminus domain-specific peptide or antibody, the analogues thereof, or the immunologically active fragment thereof by inducing the immune response by using the HRF C-terminus peptide as an antigen in an animal model except human;

2) confirming whether or not the peptide, the antibody, the analogues thereof, or the immunologically active fragment thereof produced in step 1) above could specifically bind to the antigen; and 3) separating and purifying the peptide, the antibody, the analogues thereof, or the immunologically active fragment thereof confirmed to bind specifically to the antigen in step 2).

The present invention also provides a method for identifying a HRF specific receptor containing the step of performing protein-protein interaction analysis. At this time, the protein-protein interaction analysis is performed by co-purification, yeast two-hybrid system, or protein chip system, but not always limited thereto.

The said co-purification is composed of the following steps, but not always limited thereto:
1) separating HRF-HRF receptor complex;
2) purifying the separated complex; and
3) confirming the receptor from the purified complex above.

The protein chip system above is composed of the following steps, but not always limited thereto:
1) treating the deletion form HRF or the homologous or heterologous TCTP dimer of the present invention to a protein chip in which various proteins whose functions are disclosed or not disclosed are integrated; and
2) confirming the protein-protein interaction by using the above-mentioned assay method in the presence or absence of the deletion form HRF or TCTP dimer specific antibody.

Practical and presently preferred embodiments of the present invention are illustrative as shown in the following Examples.

However, it will be appreciated that those skilled in the art, on consideration of this disclosure, may make modifications and improvements within the spirit and scope of the present invention.

It is indicated as follows to distinguish the various kinds of TCTP structures used in Examples and Experimental Examples.

Particularly, f-TCTP is the full-length TCTP, Δ-TCTP is the FL domain deleted TCTP, f-dTCTP is the dimer form of f-TCTP, Δ-dTCTP is the dimer form of FL domain-deleted TCTP, and Del-N11dTCTP is the dimer form of amino terminal-deleted TCTP.

Example 1: Construction of f-TCTP and Δ-TCTP

<1-1> Cloning of Monomer Form f-TCTP and Δ-TCTP Proteins

The construct was designed by using the sequences listed in Table 2 in order to express and extract the proteins usable for measuring the activity of HRF in which FL domain was present or deleted and for characterizing the X-ray crystal structure.

TABLE 2

| | Sequence |
|---|---|
| f-TCTP (Full TCTP) | |
| DNA (SEQ. ID. NO: 16) | ATG ATT ATC TAC CGG GAC CTC ATC AGC CAC GAT GAG ATG TTC TCC GAC ATC TAC AAG ATC CGG GAG ATC GCG GAC GGG TTG TGC CTG GAG GTG GAG GGG AAG ATG GTC AGT AGG ACA GAA GGT AAC ATT GAT GAC TCG CTC ATT GGT GGA AAT GCC TCC GCT GAA GGC CCC GAG GGC GAA GGT ACC GAA AGC ACA GTA ATC ACT GGT GTC GAT ATT GTC ATG AAC CAT CAC CTG CAG GAA ACA AGT TTC ACA AAA GAA GCC TAC AAG AAG TAC ATC AAA GAT TAC ATG AAA TCA ATC AAA GGG AAA CTT GAA GAA CAG AGA CCA GAA AGA GTA AAA CCT TTT ATG ACA GGG GCT GCA GAA |

TABLE 2-continued

| | Sequence |
|---|---|
| | CAA ATC AAG CAC ATC CTT GCT AAT TTC AAA AAC TAC CAG TTC TTT ATT GGT GAA AAC ATG AAT CCA GAT GGC ATG GTT GCT CTA TTG GAC TAC CGT GAG GAT GGT GTG ACC CCA TAT ATG ATT TTC TTT AAG GAT GGT TTA GAA ATG GAA AAA TGT TAA |
| Protein (SEQ. ID. NO: 17) | MIIYRDLISHDEMFSDIYKIREIADGLCLEVEGKMVSRT EGNIDDSLIGGNASAEGPEGEGTESTVITGVDIVMNHHL QETSFTKEAYKKYIKDYMKSIKGKLEEQRPERVKPFMTG AAEQIKHILANFKNYQFFIGENMNPDGMVALLDYREDGV TPYMIFFKDGLEMEKC |
| TCTP (FL domain deletion mutant) | |
| DNA (SEQ. ID. NO: 18) | ATG ATT ATT TAT CGC GAT CTG ATT AGC CAT GAT GAA ATG TTT TCG GAT ATT TAT AAA ATT CGC GAA ATT GCG GAT GGC CTG TGC CTG GAA GTG GAA GGC AAA ATG GTG AGC GGC GGC ATT ACC GGC GTG GAT ATT GTG ATG AAC CAT CAT CTG CAG GAA ACC AGC TTT ACC AAA GAA GCG TAT AAA AAA TAT ATT AAA GAT TAT ATG AAA TCG ATT AAA GGC AAA CTG GAA GAA CAG CGC CCG GAA CGC GTG AAA CCG TTT ATG ACC GGC GCG GCG GAA CAG ATT AAA CAT ATT CTG GCG AAC TTT AAA AAC TAT CAG TTT TTT ATT GGC GAA AAC ATG AAC CCG GAT GGC ATG GTG GCG CTG CTG GAT TAT GCG GAA GAT GGC GTG ACC CCG TAT ATG ATT TTT TTT AAA GAT GGC CTG GAA ATG GAA AAA TGC CTC GAG CAC CAC CAC CAC CAC CAC |
| Protein (SEQ. ID. NO: 19) | MIIYRDLISHDEMFSDIYKIREIADGLCLEVEGKMVSGG ITGVDIVMNHHLQETSFTKEAYKKYIKDYMKSIKGKLEE QRPERVKPFMTGAAEQIKHILANFKNYQFFIGENMNPDG MVALLDYREDGVTPYMIFFKDGLEMEKCLEHHHHHH |
| FL (FL domain) | |
| DNA (SEQ. ID. NO: 10) | AGG ACA GAA GGT AAC ATT GAT GAC TCG CTC ATT GGT GGA AAT GCC TCC GCT GAA GGC CCC GAG GGC GAA GGT ACC GAA AGC ACA GTA |
| Protein (SEQ. ID. NO: 4) | REGNIDDSLIGGNASAEGPEGEGTESTV |

To prepare the proteins above, f-TCTP and Δ-TCTP were cloned by using pET22b(+) vector (Novagen). The cloning of f-TCTP was performed by using the primers listed in Table 3. To express Δ-TCTP gene in E. coli, codon optimization was conducted. The codon-optimized Δ-TCTP full-length sequence was prepared by Bioneer, which was inserted in pET22b(+) vector by using Nde I and Xho I restriction enzyme sites.

TABLE 3

| | Primer sequence |
|---|---|
| Forward (SEQ. ID. NO: 20) | 5'-ggaattccatatga ttatctaccgggac-3' |
| Reverse (SEQ. ID. NO: 21) | 5'-ccgctcgagacatt tttccatttctaa-3' |

<1-2> Expression and Purification of Monomer Form f-TCTP Protein

Figure 7:
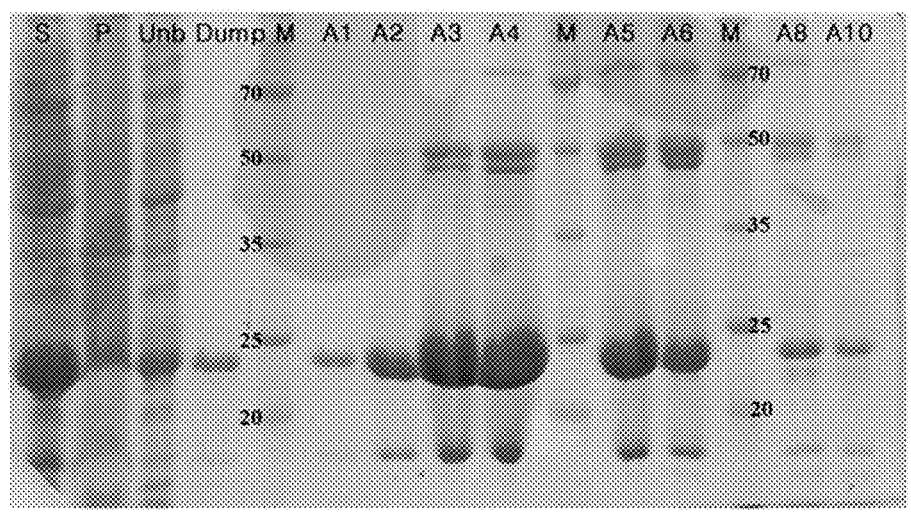
FIG. 7 is a diagram illustrating the result of f-TCTP His Trap SDS-PAGE. 37° C., over-expression for 2 and half hours, SDS-PAGE loading order: supernatant after sonication (S), pellet (P), unbound after His trap loading (Unb), dump, marker (M), fractions A1, A2, A3, A4, marker (M), A5, A6, marker (M), A8, A10. Marker size: 240-140-100-70-50-35-25-20-15-7 kDa.

E. coli BL21 (DE3-GEN-X) was transfected with the f-TCTP vector cloned in Example <1-1> on LB (Luria- Bertani) agar plate supplemented with 150 μg/ml of ampicillin (Generay Biotech). Colonies were collected, with which the frozen cell stock was prepared. The cells were cultured in ml of LB medium for overnight, which were diluted in 1000 ml fresh LB medium. The cells were cultured in a 310 K shaking incubator (N-Biotek) until $OD_{600}$ reached 0.6~0.8. When $OD_{600}$ reached 0.6~0.8, IPTG (isopropyl β-D-1-thiogalactopyranoside, Gold Biotechnology) was added thereto at the final concentration of 1 mM, followed by further culture in a 310 K shaking incubator for 2.5 hours. To harvest the cells, centrifugation was performed using a 277K high-speed refrigerated centrifuge (Hanil, Supra 22K) at 7,650 g (6,500 rev/min) for 10 minutes. The harvested cells were dissolved in 25 ml of a buffer containing 50 mM Tris-Cl (pH 8.0, Georgiachem), 100 mM NaCl (USB), 10 mM imidazole (USB), 1 mM PMSF (Sigma), 10 mg/ml DNase I, and Roche protease-inhibitor cocktail (Roche Applied Science, Indianapolis, Ind., USA), followed by lysis by using Digital Sonifier 50 (Branson Ultrasonics Co., Danbury, Conn., USA). The lysed cells were centrifuged in a 277 K high-speed refrigerated centrifuge at 24,900 g (15,000 rev/min) for 30 minutes. The supernatant was affinity-purified by AKTA Explorer system (GE Healthcare, Piscataway, N.J., USA) using HisTrap column. As shown in Table 4 and FIG. 7, f-TCTP was gradient-eluted with imidazole at the concentration from 10 to 500 mM by using a buffer containing 50 mM Tris-Cl (pH 8.0) and 100 mM NaCl, leading to elution. Then, SDS-PAGE was performed (FIG. 7).

TABLE 4

| His trap(f-TCTP) | |
| --- | --- |
| His trap binding buffer | 50 mM pH 8.0 Tris + 100 mM NaCl + 10 mM imidazole |
| His trap washing buffer | 50 mM pH 8.0 Tris + 300 mM NaCl + 10 mM imidazole |
| His trap elution buffer | 50 mM pH 8.0 Tris + 100 mM NaCl + 500 mM imidazole |

Figure 8:
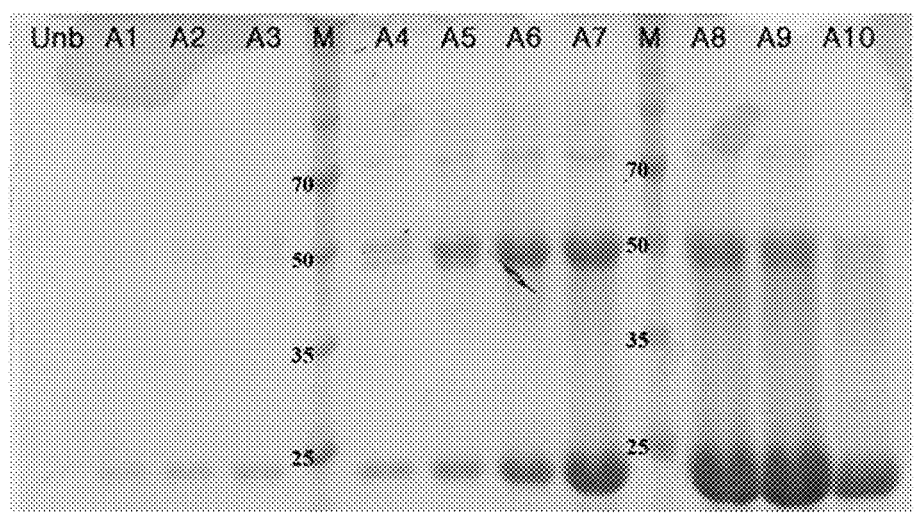
FIG. 8 is a diagram illustrating the result of f-TCTP Q (anion exchange column) SDS-PAGE. Among those fractions obtained in FIG. 7, 5 ml of the fractions A2 and A6 were 10-fold diluted. SDS-PAGE loading order: unbound after Q (anion exchange column) loading (Unb), fractions A1, A2, A3, marker (M), fractions A4, A5, A6, A7, marker (M), A8, A9, A10. Marker size: 240-140-100-70-50-35-25-20-15-7 kDa.

The f-TCTP separated above by HisTrap column proceeded secondly to ion-exchange chromatography using 5 ml of Hi-Trap Q column. As shown in Table 5 and FIG. 8, f-TCTP was gradient-eluted with NaCl at the concentration from 0 to 500 mM by using a buffer containing 20 mM Tris-Cl (pH 7.5), leading to elution. Then, SDS-PAGE was performed (FIG. 8).

TABLE 5

| Hi-Trap Q(f-TCTP) | |
| --- | --- |
| Q binding buffer | 20 mM pH 7.5 Tris |
| Q elution buffer | 20 mM pH 7.5 Tris + 1M NaCl |

<1-3> Expression and Purification of Monomer Form Δ-TCTP

Figure 9:
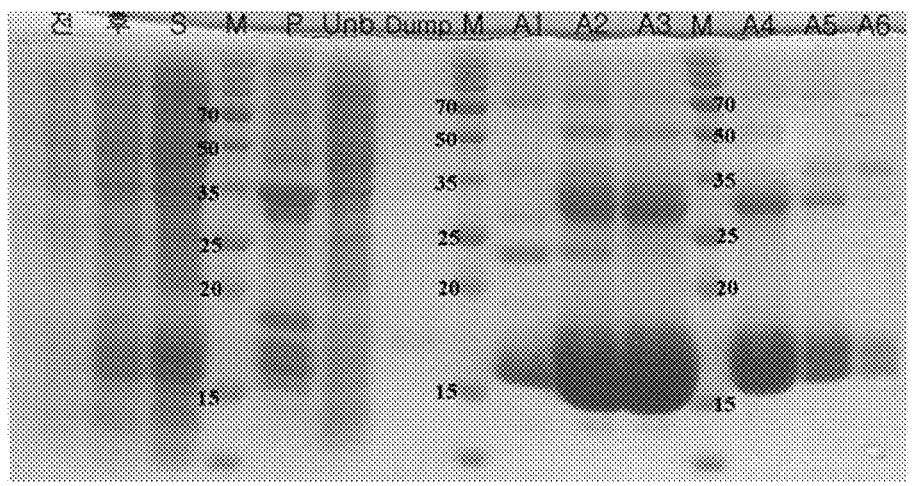
FIG. 9 is a diagram illustrating the result of Δ-TCTP His Trap SDS-PAGE. 37° C., over-expression for 2 and half hours, SDS-PAGE loading order: before over-expression (before), after over-expression (after), supernatant after sonication (S), marker (M), pellet (P), unbound after His trap loading (Unb), dump, marker (M), fractions A1, A2, A3, marker (M), A4, A5, A6. Marker size: 240-140-100-70-50-35-25-20-15-7 kDa.

Protein *E. coli* BL21 (DE3-GEN-X) was transfected with the Δ-TCTP vector cloned in Example <1-1> on LB (Luria-Bertani) agar plate supplemented with 150 μg/ml of ampicillin (Generay Biotech). Colonies were collected, with which the frozen cell stock was prepared. The cells were cultured in 5 ml of LB medium for overnight, which were diluted in 1000 ml fresh LB medium. The cells were cultured in a 310 K shaking incubator (N-Biotek) until $OD_{600}$ reached 0.6~0.8. When $OD_{600}$ reached 0.6~0.8, IPTG (isopropyl β-D-1-thiogalactopyranoside, Gold Biotechnology) was added thereto at the final concentration of 1 mM, followed by further culture in a 310 K shaking incubator for 2.5 hours. To harvest the cells, centrifugation was performed using a 277K high-speed refrigerated centrifuge (Hanil, Supra 22K) at 7,650 g (6,500 rev/min) for 10 minutes. The harvested cells were dissolved in 25 ml of a buffer containing 50 mM Tris-Cl (pH 8.0, Georgiachem), 100 mM NaCl (USB), 10 mM imidazole (USB), 1 mM PMSF (Sigma), 10 mg/ml DNase I, and Roche protease-inhibitor cocktail (Roche Applied Science, Indianapolis, Ind., USA), followed by lysis by using Digital Sonifier 50. The lysed cells were centrifuged in a 277 K high-speed refrigerated centrifuge at 24,900 g (15,000 rev/min) for 30 minutes. The supernatant was affinity-purified by AKTA Explorer system using His-Trap column. As shown in Table 6 and FIG. 9, Δ-TCTP was gradient-eluted with imidazole at the concentration from 10 to 500 mM by using a buffer containing 50 mM Tris-Cl (pH 8.0) and 100 mM NaCl, leading to elution. Then, SDS-PAGE was performed (FIG. 9).

| His trap(Δ-TCTP) | |
| --- | --- |
| His trap binding buffer | 50 mM pH 8.0 Tris + 100 mM NaCl + 10 mM imidazole |
| His trap washing buffer | 50 mM pH 8.0 Tris + 300 mM NaCl + 10 mM imidazole |
| His trap elution buffer | 50 mM pH 8.0 Tris + 100 mM NaCl + 500 mM imidazole |

Figure 10:
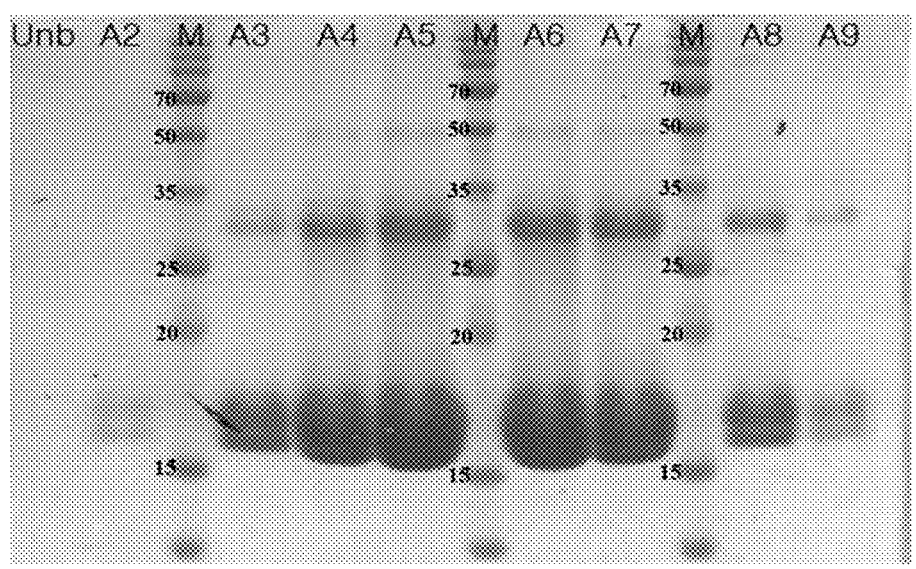
FIG. 10 is a diagram illustrating the result of Δ-TCTP Q (anion exchange column) SDS-PAGE. Among those fractions obtained in FIG. 9, 3 ml of the fractions A2~A4 were 10-fold diluted. SDS-PAGE loading order: unbound after Q (anion exchange column) loading (Unb), fractions A2, marker (M), fractions A3, A4, A5, marker (M), A6, A7, marker (M), A8, A9. Marker size: 240-140-100-70-50-35-25-20-15-7 kDa.

The Δ-TCTP separated above by HisTrap column proceeded secondly to ion-exchange chromatography using 5 ml of Hi-Trap Q column. As shown in Table 7 and FIG. 10, Δ-TCTP was gradient-eluted with NaCl at the concentration from 0 to 500 mM by using a buffer containing 20 mM Tris-Cl (pH 7.5), leading to elution. Then, SDS-PAGE was performed (FIG. 10).

TABLE 7

| Hi-Trap Q(Δ-TCTP) | |
| --- | --- |
| Q binding buffer | 20 mM pH 7.5 Tris |
| Q elution buffer | 20 mM pH 7.5 Tris + 1M NaCl |

<1-4> Formation of Dimer Form f-dTCTP and Δ-dTCTP Proteins

The f-TCTP and Δ-TCTP separated by chromatography in Examples <1-2> and <1-3> were concentrated and treated with 1 mM tertiary butyl hydroperoxide to induce dimerization. As a result, f-dTCTP and Δ-dTCTP were constructed.

Example 2: Crystallization of f-dTCTP and Δ-dTCTP, and Data Collection

The optimum condition for the crystallization of f-dTCTP and Δ-dTCTP proteins was screened and determined and also the stabilized cryo-condition was screened in order to collect information from synchrotron. X-ray data of the crystallized f-dTCTP and Δ-dTCTP proteins were collected in the stabilized cryo-condition.

<2-1> Crystallization of f-dTCTP and Δ-dTCTP

The optimum concentration of f-dTCTP and Δ-dTCTP for the crystallization was determined by sedimentation experiment, which was 50 mg/ml. The early crystallization was performed by hanging drop vapor diffusion method or sitting-drop vapor diffusion method manually or automatically based on sparse matrix theory (Jancarik & Kim, *J Appl*

Cryst, 24, 409-411, 1991) by using a screening kit (Screen I & II, Index screen reagents, Hampton Research, Laguna Niguel, CA, USA). The automatic examination was performed by high-throughput crystallization system established by the present inventors via Hydra e-Drop (Thermo Scientific, Waltham, Mass., USA). The optimum condition for the crystallization of f-dTCTP protein was as follows: The crystallization solution (mother liquor) composed of 25% PEG 3350 and 0.1 M Bis-Tris (pH 5.5) was loaded in each well (200 µℓ/well). 2 µℓ of a hanging drop made by mixing the crystallization solution and the protein (50 mg/ml) at the ratio of 1:1 was placed on a cover glass, and crystals were formed by vapor diffusion method. The optimum condition for the crystallization of Δ-dTCTP protein was as follows: The crystallization solution composed of 30% PEG 300 and 0.1 M MES (pH 6.5) was loaded in each well (200 µℓ/well). 2 µℓ of a hanging drop made by mixing the crystallization solution and the protein (50 mg/ml) at the ratio of 1:1 was placed on a cover glass, and crystals were formed by hanging drop vapor diffusion method.

<2-2> Screening of Cryo-Condition of f-dTCTP and Δ-dTCTP

The process of finding the stabilized cryo-condition is essential in the process of data collection in a synchrotron. The strength of the synchrotron radiation is so strong, so that proteins in the crystals are easily oxidized. As a result, authentic data collection is not possible because the protein skeleton has been degraded. So, the present inventors have found the cryo-condition for the crystals to be flash-frozen. LV cryo-oil (MiTeGen, Ithaca, N.Y.) was used for the crystallization of f-dTCTP. The drop containing f-dTCTP crystals was added to the mixture (solution and LV cryo-oil, 1:1, v/v), and the crystals were scooped by using a mounting loop, followed by flash-freezing. 100% PEG 300 was used for Δ-dTCTP. The drop containing Δ-dTCTP crystals was added to the mixture (well solution and 100% PEG 300, 1:1, v/v), and the crystals were scooped by using a mounting loop, followed by flash-freezing.

<2-3> Collection of X-Ray Data of f-dTCTP and Δ-dTCTP

X-ray data of f-dTCTP was collected up to 2.7 Å from Pohang Light Source (PLS), Pohang Accelerator Laboratory (PAL), which is shown in Table 8. The detector was ADSC Q315r. X-ray data of Δ-dTCTP was collected up to 1.79 Å from Swiss Light Source. At this time, philatus was used as the detector.

TABLE 8

| | f-dTCTP | Δ-dTCTP |
|---|---|---|
| X-ray source | Pohang Light Source (PLS) | Swiss Light Source (SLS) |

TABLE 8-continued

| | f-dTCTP | Δ-dTCTP |
|---|---|---|
| X-ray wavelength (Å) | 0.97941 | 1.000 |
| Temperature (K) | 100 | 100 |
| Space group | P4$_3$ | P6$_1$22 |
| Unit cell parameter | | |
| a = b (Å) | 56.3 | 69.3 |
| c (Å) | 195.6 | 146.5 |
| γ (°) | | 120 |
| V$_m$ (Å$^2$/Dalton) | 2.00 | 3.01 |
| Resolution range (Å) | 50.00-2.70 (2.75-2.70) | 46.44-1.79 (1.89-1.79) |
| Unique reflections | 15213 (767) | 19809 (2719) |
| R$_{sym}$ (%) | 11.5 (84.8) | 4.2 (67.0) |
| Data completeness (%) | 90.8 (93.1) | 97.9 (86.3) |
| Average I/σ | 8.4 (1.24) | 12.0 (1.2) |

*The values in parentheses are for the highest resolution shell.

Example 3: Analysis of Crystal Structures of f-dTCTP and Δ-dTCTP

<3-1> Identification of Crystal Structures of f-dTCTP and Δ-dTCTP by Molecular Replacement The crystal structures of f-dTCTP and Δ-dTCTP were identified by solving the phase problem by using molecular replacement. Since the structural similarities between proteins were expected, the method to solve the phase problem by molecular replacement has been used using the known structures. The molecular orientation was searched by using fast rotation function and the molecular location was searched by using translation function, R-factor search, and correlation search. The obtained approximate orientation and location were refined by rigid body refinement or R-factor minimization, followed by refinement and model rebuilding of atomic positions. To accomplish the molecular replacement, such programs as CNS (Brunger et al., Acta Cryst, D 54, 905-921, 1998), AMoRe (Navaza, Acta Crystallogr D Biol Crystallogr, 49, 588-591, 1993), EPMR (Kissinger et al., Acta Crystallogr D Biol Crystallogr, 57, 1474-1479, 2001), and PHASER were used. To disclose the crystal structures of f-dTCTP and Δ-dTCTP, human TCTP structure (PDB ID: 2HR9) was used as a test model for EPMR. The phase of Δ-dTCTP was obtained by molecular replacement using the human TCTP model. The primary model was constructed by using a graphic software COOT (Emsley & Cowtan, Acta Crystallogr D Biol Crystallogr, 60, 2126-2132, 2004), and the energy minimization was performed by using CNS. The final model was obtained by PHENIX (Adams et al., Acta Crystallogr D Biol Crystallogr, 66, 213-221, 2010). The refined valued of the final model are shown in Table 9 below.

TABLE 9

| Crystal parameters and refinement statistics | f-dTCTP | Δ-dTCTP |
|---|---|---|
| Space group | P4$_3$ | P6$_1$22 |
| Cell dimensions | 56.3 Å × 56.3 Å × 195.6 Å | 69.3 Å × 69.3 Å × 146.5 Å |
| Volume fraction of solvent | 38.69% | 57.58% |
| V$_m$ (Å$^2$/Dalton) | 2.00 | 3.01 |
| Total number of residues | 596 | 149 |
| Total non-H atoms | 4902 | 1217 |
| Number of water molecules | 43 | 71 |
| Average temperature factors | | |
| Protein | 53.75 Å$^2$ | 33.39 Å$^2$ |
| Solvent | 42.80 Å$^2$ | 39.97 Å$^2$ |

TABLE 9-continued

| Crystal parameters and refinement statistics | f-dTCTP | Δ-dTCTP |
|---|---|---|
| Resolution range of reflections used | 50.0-2.7 Å | 46.44-1.79 Å |
| Amplitude cutoff | 0.0 σ | 0.0 σ |
| R-factor | 22.7% | 22.6% |
| Free R-factor | 31.5% | 26.2% |
| Stereochemical ideality: | | |
| Bond | 0.009 Å | 0.008 Å |
| Angle | 1.167° | 1.166° |
| Chirality | 0.078° | 0.090° |
| Planarity | 0.004° | 0.004° |
| Dihedral | 18.56° | 16.31° |
| Ramachandran plot | | |
| Residues in most favored regions | 87.7% | 90.9% |
| Residues in additional allowed regions | 11.7% | 8.3% |
| Residues in generously allowed regions | 0.6% | 0.8% |
| Residues in disallowed regions | 0.0% | 0.0% |

Figure 11:
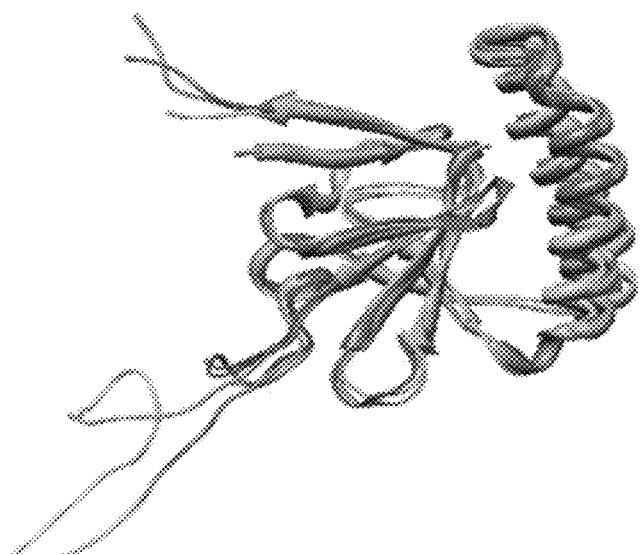
FIG. 11 is a diagram illustrating the comparison of the structures of f-TCTP (green), Δ-TCTP (pink), and TCTP (2HR9, blue-green), identified by NMR.

<3-2> Identification of Three-Dimensional Crystal Structures of Monomer Form f-TCTP and Δ-TCTP As a result of examination of the structures of f-TCTP and Δ-TCTP, the monomer forms of f-dTCTP and A-dTCTP, the structures were confirmed to be similar to that of the test model above (FIG. 11).

Figure 12:
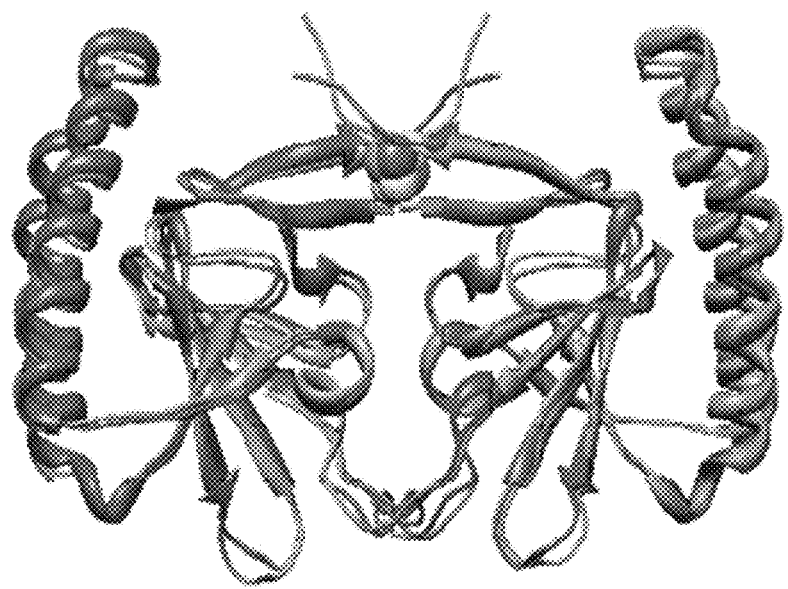
FIG. 12 is a diagram illustrating the comparison of the structures of f-dTCTP (green) and Δ-dTCTP (pink) formed by disulfide bond.

<3-3> Identification of Three-Dimensional Crystal Structures of Dimer Form f-dTCTP and A-dTCTP The Δ-dTCTP constructed in the presence of tertiary butyl hydroperoxide was, as expected, a dimer form made by disulfide bridge between C-terminal cysteines. It was unique in this structure that it could be formed as a dimer structure even though N-terminal residue was not deleted. Due to the absence of FL, the problem of colliding at the dimer interface disappeared and the packing was good, so that the crystals of Δ-dTCTP were much larger than those of f-dTCTP and the diffraction resolution was good. However, the electron density of FL was not found in f-dTCTP because of the flexibility of FL. In the three-dimensional structure of the identified f-dTCTP and A-dTCTP, each monomer closely matched the native TCTP used as the test model. The three-dimensional structure of the dimer form f-dTCTP and Δ-dTCTP was a symmetrical butterfly shape and the dimer structure was confirmed to be mediated by Cys172, as expected (FIG. 12).

Interestingly, the three-dimensional structures of f-dTCTP and Δ-dTCTP were similar to each other. The electron density was not detected in f-dTCTP because of the flexibility of FL and the structure thereof was exposed on the surface so that it did not collide with the body structure nor did affect the body structure. The three-dimensional structures of f-dTCTP and Δ-dTCTP were compared with those of f-TCTP and Δ-TCTP. As a result, due to the different surface structure, the partner proteins involved in the physiological action of monomers and dimers played different roles.

In the previous research by the present inventors, it was confirmed that the dimer form of the wild-type TCTP prepared by using the Fc region of an antibody had the cytokine secretory activity and once TCTP formed a dimer, it was activated by HRF even without the deletion of N-terminus (Kim et al., PLoS one, 4, e6464, 2009). Therefore, it was confirmed that the formation of TCTP dimer was important for the activity of HRF.

Example 4: Construction of Wild-Type f-dTCTP Structure Containing FL Formed by Modeling It was not able to obtain the electron density of f-dTCTP due to the flexibility of FL. Therefore, the structure of f-dTCTP containing FL was constructed by modeling. As a result of modeling the FL domain with energy minimization, it was confirmed that FL in the f-dTCTP structure was apart from the main body of HRF, so that the HRF structure was not much affected by the presence absence of FL as a whole.

<4-1> Modeling Process of Wild-Type f-dTCTP Structure Containing FL

Since the structure of f-dTCTP was not observed because of the flexibility of FL, f-dTCTP structure was constructed by modeling in the presence of FL. The structure of FL was based on the structure of NMR used as the test model. FL domain was energy minimized using TINKER 6.0 package. Charmm22 was used as the force field for all programs.

First, the structure to refine was converted from pdb file to xyz file using PDBXYZ program of TINKER package. The xyz file uses Cartesian coordinates system as the default file format for all programs of TINKER. It contains all the names for each atom in the structure and X-Y-Z-coordinates, force field atom type number of atom and the atom connection information. After converting pdb file to xyz file, the protein structure was minimized by using a minimizing program of TINKER package.

The protein structure minimizing program enabled the limited memory L-BFGS minimization using the modified version of Jorge Nocedal algorithm in Cartesian coordinates. To minimize FL domain alone, the atomic number of FL domain was written in the key file after the active command. Atomic numbers 594~1019 and 3382~3807 of the xyz file corresponding to the region from 37 Ser 69 Gly of Chain 1 and 213 Ser~245 Gly of Chain 2 were written after the active command (active 594, active 595, active 596 . . . and so on). The minimization was executed by Minimize.x. At this time, the value of Root men square (RMS) gradient was 0.1. The RMS gradient is the differential coefficient of the energy which is used as the standard for determining how far the energy can be minimized. For example, when RMS is 0, the minimization occurs until the energy is fully minimized. But, in reality, RMS cannot be 0, and thus the standard minimized value is necessary. Upon completion of the minimization, xyz file was converted back to pdb file by using XYZPDB program to obtain the protein structure. To investigate the stability of the protein structure before and after the energy minimization, total potential energy and its Components and list of the large individual interactions were examined by using ANALYZE program.

<4-2> Identification of f-dTCTP Structure Containing FL by Modeling

First, before minimizing FL, the total potential energy was examined and the results are shown in Table 10 below.

TABLE 10

Total Potential Energy: 1010627540.1709 Kcal/mole

|  | Kcal/mole | Interactions |
| --- | --- | --- |
| Bond Stretching | 278.2128 | 856 |
| Angle Bending | 346.2104 | 1542 |
| Urey-Bradley | 25.2941 | 614 |
| Improper Dihedral | 158.5687 | 188 |
| Torsional Angle | 415.7188 | 2250 |
| Van der Waals | 1010625491.6590 | 4384976 |
| Charge-Charge | 1171.8493 | 4339845 |
| Implicit Solvation | −347.3423 | 5576 |

After minimizing FL structure energy, the total potential energy was also investigated and the results are shown in Table 11. After minimizing the energy, the structure was more stabilized due to the reduced energy.

TABLE 11

Total Potential Energy: 6347.5705 Kcal/mole

|  | Kcal/mole | Interactions |
| --- | --- | --- |
| Bond Stretching | 4397.9137 | 5629 |
| Angle Bending | 1386.2914 | 10182 |
| Urey-Bradley | 143.5526 | 4894 |
| Improper Dihedral | 132.2450 | 994 |
| Torsional Angle | 1819.1975 | 14847 |
| Van der Waals | 3676.4098 | 15527289 |
| Charge-Charge | −5208.0396 | 15294410 |

Since the structure of f-dTCTP was not able to be determined due to the flexibility of FL, the structure of f-dTCTP containing FL was constructed by modeling using TINKER, as described above.

Figure 13:
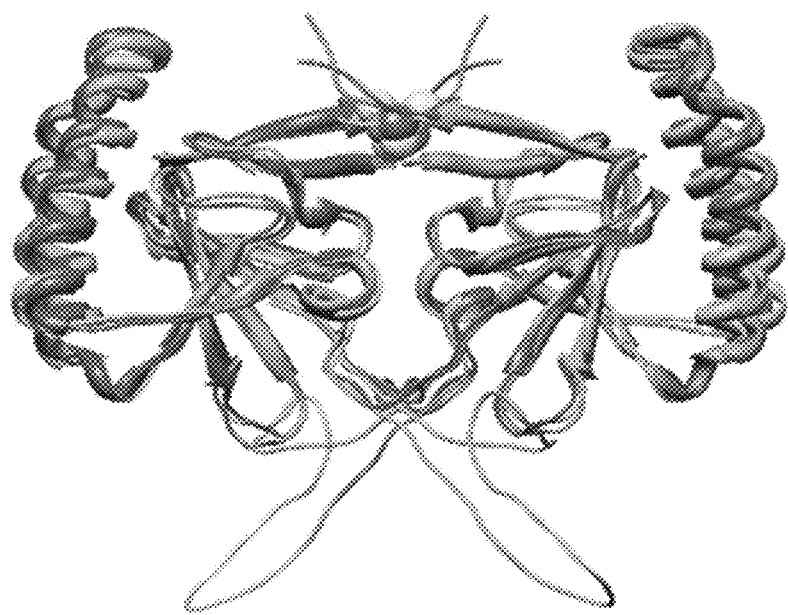
FIG. 13 is a diagram illustrating the comparison of the structures of f-dTCTP (green) and Δ-dTCTP (pink) formed by disulfide bond, and model HRF (blue-green).

As a result, as shown in FIG. 13, it was confirmed that FL was apart from the main body of HRF, so that it did not affect the general structure overall (FIG. 13).

Example 5: Investigation of the Underlying Mechanism how dTBP2 (dTCTP Binding Peptide 2) that Binds to HRF Controls Activity of f-dTCTP <5-1> Construction and Separation of Heptamer (7Mer) Binding to HRF HRF was immobilized on the plastic well. The peptide capable of binding to HRF was isolated by affinity selection of 7-mer random peptide library (New England Biolabs, USA).

Particularly, HRF was dissolved in a coating buffer (0.1 M NaHCO 3, pH 8.6) at the concentration of 20 µg/ml, which was loaded in a polystyrene microtiter plate (50 µℓ/well), followed by coating at 4° C. for overnight and blocking non-specific binding with BSA. The plate was washed with 0.1% Tween/TBS (TBST) 6 times. 10 µℓ of phage-displayed peptide library stock solution was diluted in 40 µℓ of 3% BSA/TBS, which was added to the above. The plate stood at room temperature for 1 hour. TBST was added thereto, and the plate stood for 5 minutes, followed by washing. The washing was performed once after one round of panning, 5 times after 2 and 3 rounds of panning, and 10 times after 4 rounds of panning. 50 µℓ of glycine/HCl buffer (pH 2.2) was added thereto, which stood for 5 minutes.

Then, phages were eluted, and then neutralization was induced with 8 µℓ of 1 M Tris-HCl (pH 9.1). The eluted phage solution was added to 20 mℓ of ER2537 culture medium ($OD_{600}$=0.5~1), followed by culture in a 37° C. shaking incubator (rpm=200) for 2 hours. 100 mℓ of SB medium was added thereto, followed by culture for overnight with shaking (250 rpm). The culture solution was centrifuged at 10,000 rpm (4° C.) for 15 minutes. 100 mℓ of the obtained supernatant was added with 30 mℓ of 5×PEG/NaCl (20% PEG(w/v), 15% NaCl (w/v)), followed by dissolving for 5 minutes. The mixture was then left in ice for 30 minutes. The mixture was centrifuged at 10,000 rpm (4° C.) for 20 minutes and the supernatant was discarded. The obtained pellet was suspended in 1 mℓ of 3% BSA/TBS. After performing centrifugation at 14,000 rpm for 5 minutes, the supernatant was obtained and used for panning. Affinity purification and phage replication were repeated 4 times, followed by eluting phages. Each phage clone was obtained from the proper plate of the eluted phage, followed by ELISA. Those phage clones showing a specific affinity to HRF were separated, followed by sequencing to confirm the peptide sequence. Those phage display peptides showing dominant binding to HRF were selected and listed below:

amino acid sequence of ph1 (p1): LVTYPLP (SEQ. ID. NO: 23);

amino acid sequence of ph2 (p2): WYVYPSM (SEQ. ID. NO: 24);

amino acid sequence of ph3 (p3): SYLPYPY; and amino acid sequence of ph4 (p4): WEFPGWM (SEQ. ID. NO: 25).

The binding affinity of the phage obtained above was compared by ELISA.

That is, each phage plaque was added to 1 mℓ of the ER2537 culture medium ($OD_{600}$=0.5~1) cultured in SB medium, followed by culture in a 37° C. incubator (rpm=250) for 5 hours. 100 µℓ of each culture solution was added to 900 µℓ of SB medium, followed by culture for overnight. Centrifugation was performed twice at 14,000 rpm for 5 minutes and the obtained supernatant was used for ELISA.

Each phage solution separated above was diluted in an equal volume of 6% BSA/PBS, and 50 µℓ of the diluted solution was added to each well of the plastic well plate coated with HRF or BSA (control), which stood for 2 hours. After washing the plate with PBST 5 times, HRP-conjugated anti-M13 antibody (Pharmacia) diluted with 3% BSA/PBS (1:5000) was added thereto (100 µℓ/well), which stood for 1 hour. The plate was washed with PBST 6 times and with PBS once. After adding peroxidase substrate solution thereto (100 µℓ/well), $OD_{405}$ was measured with an ELISA reader. As a result, it was confirmed that the phages ph1, ph2 and ph4 of the present invention, particularly ph2 and ph4, specifically bind to HRF.

HRF was diluted serially by ⅕ fold each from the concentration of 20 µg/mℓ (20, 4, 0.8, 0.16, and 0.032 µg/mℓ), which was fixed in the plastic well (50 µℓ/well). The phage 2 solution diluted serially by ⅕ fold each (½, ¹⁄₁₀, ¹⁄₅₀, ¹⁄₂₅₀, and ¹⁄₁₂₅₀ of the stock solution) was added thereto, followed by ELISA and $OD_{405}$ was measured. As a result, it was confirmed that the phage ph2 clone of the present invention maintained its binding force to HRF even to the HRF diluted until 0.4, 0.08, 0.016, and 0.032 µg/mℓ.

In order to confirm the residues involved in the HRF binding affinity of the heptamer peptide of the present invention, the amino acid sequence of p2 was substituted with alanine (A), and only m5 was substituted with lysine (K). As a result, the following sequences were established:

amino acid sequence of heptamer peptide m1: AYVYPSM (SEQ. ID. NO: 26);

amino acid sequence of heptamer peptide m2: WAVYPSM (SEQ. ID. NO: 27);

amino acid sequence of heptamer peptide m3: WYAYPSM (SEQ. ID. NO: 28);

amino acid sequence of heptamer peptide m4: WYVAPSM (SEQ. ID. NO: 29);

amino acid sequence of heptamer peptide m5: WYVYKSM (SEQ. ID. NO: 30);

amino acid sequence of heptamer peptide m6: WYVYPAM (SEQ. ID. NO: 31); and amino acid sequence of heptamer peptide m7: WYVYPSA (SEQ. ID. NO: 32).

The HRF binding affinity of the peptide was measured by ELISA and as a result, the HRF binding affinity was p2, m6>m7>m3>m2>fm5>M1>m4.

Figure 14:
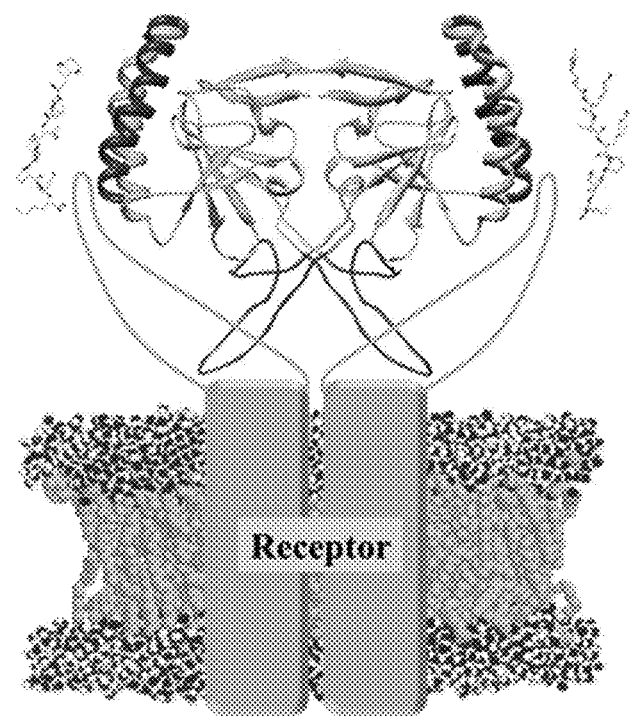
FIG. 14 is a diagram illustrating the binding model between HRF and its receptor and the binding model between HRF and dTBP2 peptide.

<5-2> Investigation of Underlying Mechanisms how dTBP2 Regulates the Activity of f-TCTP In the receptor-binding model of f-dTCTP identified by the modeling-derived structure, the regulation of f-dTCTP activity by the 7-mer peptide dTBP2 (Example <5-1> p2) was affected by FL. In the case of the monomer form f-TCTP, FL moves freely so that it can interrupt the binging of dTBP2. In the case of the dimer form f-dTCTP, FL has a directional property, so that it can help the binding of dTBP2 with H2 helix (FIG. 14, red helix part). In the f-dTCTP structure, the FL and H2 domains were expected to bind directly to the receptor. As shown in the modeling structure, dTBP2-f-dTCTP binding was mediated by FL and H2 domains. In the meantime, binding of f-dTCTP to the receptor through FL and H2 was inhibited domains. So, it can be predicted that they exhibit inhibitory activity on signal transduction. Thus, the binding inhibitor of the present invention also includes the indirect inhibitor of the binding between HRF and the receptor thereof by binding to H2 domain or other region of HRF, such as dTBP2.

Figure 15:
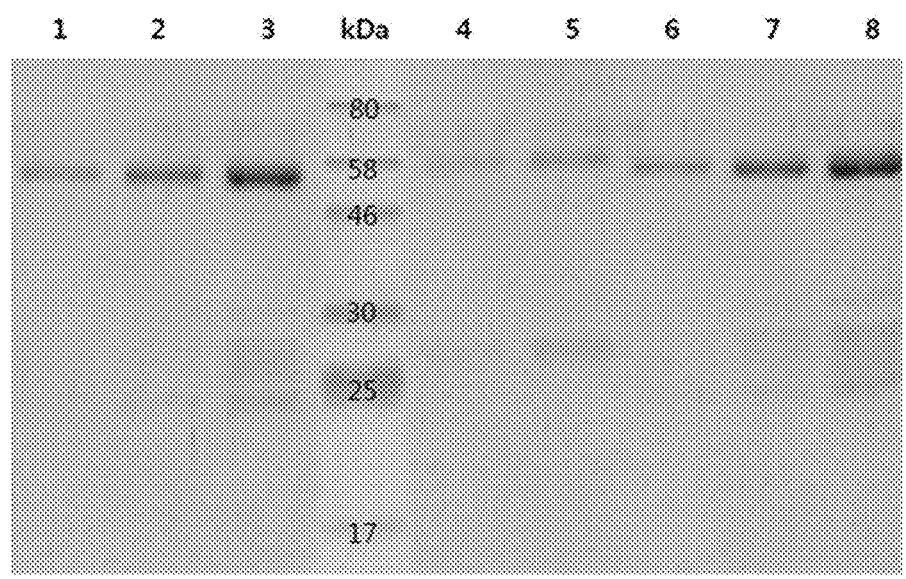
FIG. 15 is a diagram illustrating the result of SDS-PAGE, wherein an antibody binding specifically to HRF receptor binding domain was constructed and IgG was obtained by affinity chromatography which proceeded to SDS-PAGE. Wherein, 1-3 indicate the antibodies binding to FL (1: 0.5 µg, 2: 1 µg, 3: 2 µg), 4-5 indicate BGG (4: 0.5 µg, 5: 1 µg), and 6-8 indicate the antibodies binding to H2 (6: 0.5 µg, 7: 1 µg, 8: 2 µg).

Example 6: Construction of Antibody Recognizing and Binding to FL and H2 Domains The present inventors constructed antibodies to inhibit the HRF activity by binding to FL domain or H2 domain, the HRF receptor binding domains. The antibodies recognize and bind specifically to FL and H2 domains were constructed by AbClon according to the conventional method. The rabbit (New Zealand White) was immunized with a receptor binding domain peptide as an antigen to produce a specific polyclonal antibody. It was examined that the produced antibody was antigen-specific. IgG binding to the receptor binding domains FL and H2 was purified by antigen-specific affinity chromatography, followed by SDS-PAGE (FIG. 15).

Example 7: Construction of Asthma and Rhinitis Animal Models Induced with Ovalbumin The present inventors constructed asthma and rhinitis animal models by using ovalbumin in order to evaluate the effect of the HRF receptor binding domains FL and H2 and the antibodies thereof on asthma and rhinitis.

Figure 16:
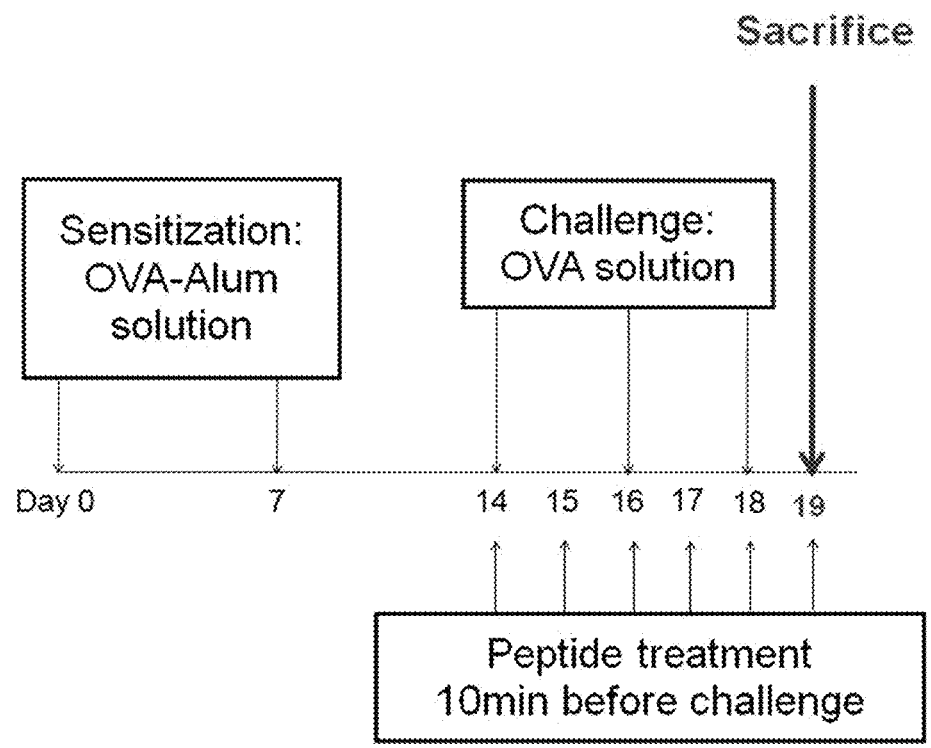
FIG. 16 is a diagram illustrating the protocol and imminization schedule for the administration of the peptide to the constructed asthma and rhinitis disease models.
Figure 26:
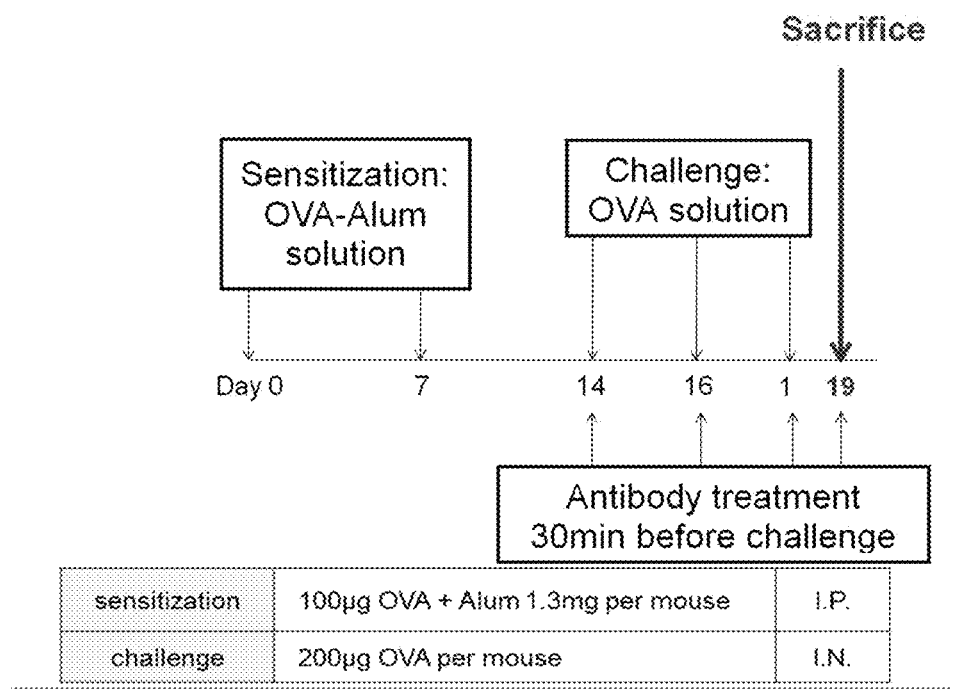
FIG. 26 is a diagram illustrating the protocol of the administration of pre-immune IgG and anti-C-terminus IgG antibody to the asthma and rhinitis disease models of FIG. 16.

Particularly, 5 week old specific pathogen free BALB/c female mice (weight: approximately 20 g) were purchased from Orientbio Inc. (Seoul, Korea), followed by stabilization in an animal laboratory for 1 week. The mice were administered with 200 $\mu\ell$ of PBS containing 1.3 mg of aluminum hydroxide (Sigma A8222) and 100 µg of ovalbumin (Sigma A5503) via intraperitoneal injection twice at a week interval, followed by sensitization. Then, 20 $\mu\ell$ of PBS containing 200 µg of ovalbumin dissolved therein was administered via intranasal instillation on day 14, day 16, and day 18 to induce immune response. PBS was administered for the positive control and FL and H2 domains and the antisera or antibodies thereof were administered via intraperitoneal injection 10 minutes before antigen administration. On day 15, day 17, and day 19, intraperitoneal administration was performed without antigen administration. On day 19, the animals were sacrificed 2 hours after the administration (FIG. 16). 50 µg of anti-C terminus IgG was administered via intranasal instillation or intraperitoneal injection 30 minutes before the antigen administration on day 14, day 16, and day 18. 24 hours after the last administration, the animals were sacrificed (FIG. 26).

Example 8: Construction of Antibody Recognizing and Binding to C-Terminus Domain The present inventors constructed antibodies to inhibit the activity of HRF by binding to C-terminus domain of the HRF structure.

Particularly, the antibody specifically recognizing and binding to C-terminus domain was prepared by Peptron according to the conventional method. The specific polyclonal antibody was produced in rabbits (New Zealand White) by inducing immune response using the C-terminal peptide (Ac-FFKDGLEMEKC-NH2) as an antigen. It was confirmed whether the produced antibody was antigen-specific. IgG was separated and purified from the antiserum by using protein A.

Experimental Example 1: Analysis of IL-8 and GM-CSF Secretion Mediated by f-TCTP, Δ-dTCTP, and Del-N11dTCTP in BEAS-2B Cells To investigate the IL-8 and GM-CSF secretory activity of f-TCTP, Δ-dTCTP, and Del-N11dTCTP in BEAS-2B cells, the present inventors compared the activity of f-TCTP, Δ-dTCTP, and Del-N11dTCTP by measuring the secretion of IL-8 in BEAS-2B cells.

Particularly, BEAS-2B cells were cultured in a 48-well plate until the confluency reached to 70%. Then, the cells were washed with 1% penicillin-streptomycin/BEBM (Clonetics) twice. Each recombinant protein of the Δ-dTCTP separated in Example 1 of the invention, and the f-TCTP and Del-N11dTCTP constructed by the method described in Korean Patent Application No. 2006-0007663 was added thereto at the concentration of 1 µg/m$\ell$, 5 µg/m$\ell$, or 10 µg/m$\ell$ 24 hours later, the supernatant was obtained and the released IL-8 and GM-CSF were quantified by ELISA.

Figure 2:
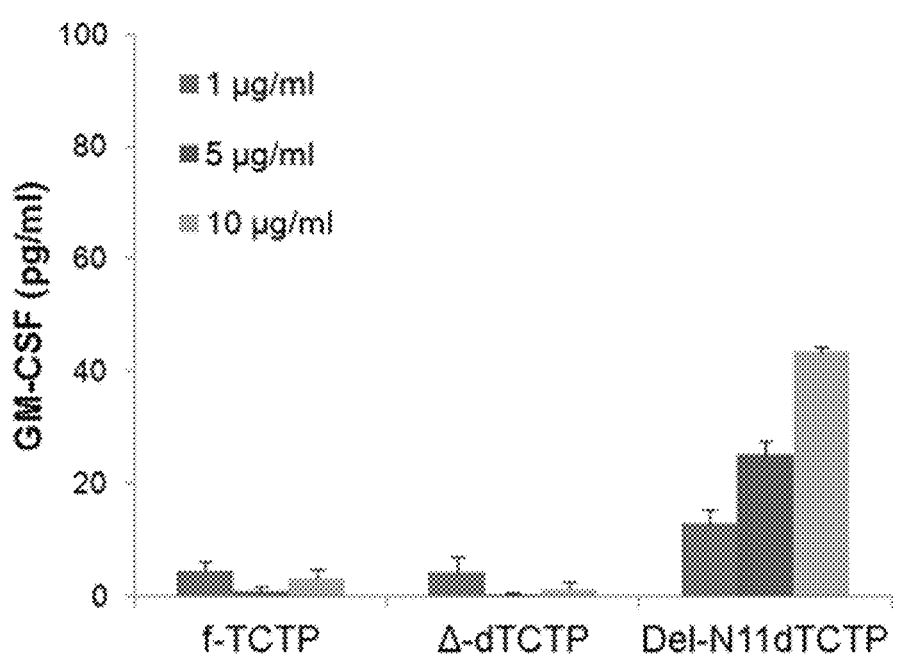
FIG. 2 is a graph illustrating the comparison of GM-CSF inducing ability of f-TCTP, Δ-dTCTP, and Del-N11dTCTP according to the treatment at various concentrations in BEAS-2B cells.

As a result, as shown in FIGS. 1 and 2, it was confirmed that Del-N11dTCTP was superior to f-TCTP and Δ-dTCTP in the secretion of IL-8 and GM-CSF (FIGS. 1 and 2).

Experimental Example 2: Analysis of Affinity to dTBP2 of f-TCTP, Δ-dTCTP, and Del-N11dTCTP To investigate the affinity to dTBP2 of f-TCTP, Δ-dTCTP, and Del-N11dTCTP of the present invention, biotin was conjugated to the COOH-terminus of dTBP2 known to bind to HRF, followed by purification. The purified protein was immobilized in the plastic well coated with streptavidin, to which f-TCTP, Δ-dTCTP, and Del-N11dTCTP were added. Then, the binding strength of each protein was investigated.

Particularly, 50 µℓ of the biotinylated dTBTP2 dissolved in a buffer (TBS [25 mM Tris, 150 mM NaCl, pH 7.2], 0.1% BSA, 0.05% Tween-20) at different concentrations of 0.01, 0.1, 1, and 10 µm was added to Reacti-Bind Streptavidin Coated Polystyrene Plates (PIERCE), followed by reaction at room temperature for 2 hours. The plate was washed with a washing buffer three times. Each of f-TCTP, Δ-dTCTP, and Del-N11dTCTP was dissolved in TBS at the concentration of 0.2 µg/mℓ. 60 µℓ of the mixture was added to each well of the plate, followed by reaction for 1 hour. The plate was washed with a washing buffer three times. 100 µℓ of anti-HRF rabbit antibody (Bio-Rad) diluted in a buffer (1:2000) was added to each well of the plate, which stood at room temperature for 30 minutes. The plate was washed with a washing buffer three times and with TBS once, to which HRP-conjugated anti-rabbit antibody (1:2000) was added (100 µℓ/well), which stood at room temperature for 30 minutes. The plate was washed with a washing buffer three times and with TBS once, to which TBS (PIERCE), the peroxydase substrate solution, was added (100 µℓ/well). Color development was measured at 450 nm and 570 nm using an ELISA reader (Bio-Rad), and affinity was determined by the difference.

Figure 3:
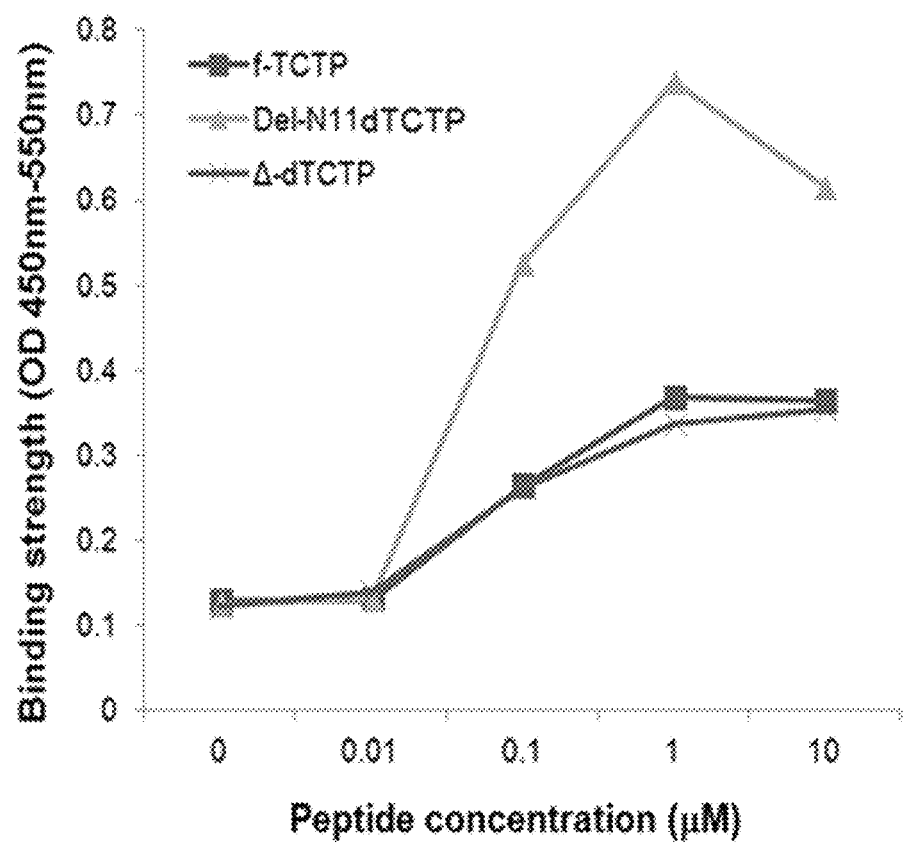
FIG. 3 is a graph illustrating the affinity of f-TCTP, Δ-dTCTP, and Del-N11dTCTP to the peptide dTBP2 (dTCTP binding peptide 2), investigated by ELISA.

As a result, as shown in FIG. 3, it was confirmed that Del-N11dTCTP had higher dTBP2 affinity than f-TCTP and Δ-dTCTP (FIG. 3).

Experimental Example 3: Analysis of Del-N11dTCTP Inhibition Activity of FL Domain, Helix 2 Domain, and Helix 3 Domain To investigate inhibitory effect of FL domain, Helix 2 domain, and Helix 3 domain on Del-N11dTCTP, the inventors synthesized FL domain (Ac-SRTEGAIDDSLIGGNA-SAEGPEGEGTESTVVT-NH2) (SEQ. ID. NO: 1), Helix 2 domain (Ac-TKEAYKKYIKDYMKSLKGKLEEQKP-NH2) (SEQ. ID. NO: 11), and Helix 3 domain (Ac-KPER-VKPFMTGAAEQIKHILANFN-NH2) (SEQ. ID. NO: 22) by using the synthetic peptides prepared with NH2-terminal acetylation and COOH-terminal amidation, followed by purification.

Particularly, BEAS-2B cells were treated with Del-N11dTCTP (70 nM) by the same manner as described in Experimental Example 1. At this time, the synthesized FL domain, Helix 2 domain, and Helix 3 domain were treated to the cells at different molar ratios (0~1), followed by reaction for 30 minutes. Then, Del-N11dTCTP was added thereto. 24 hours later, the supernatant was obtained and the released IL-8 was quantified by ELISA.

Figure 4:
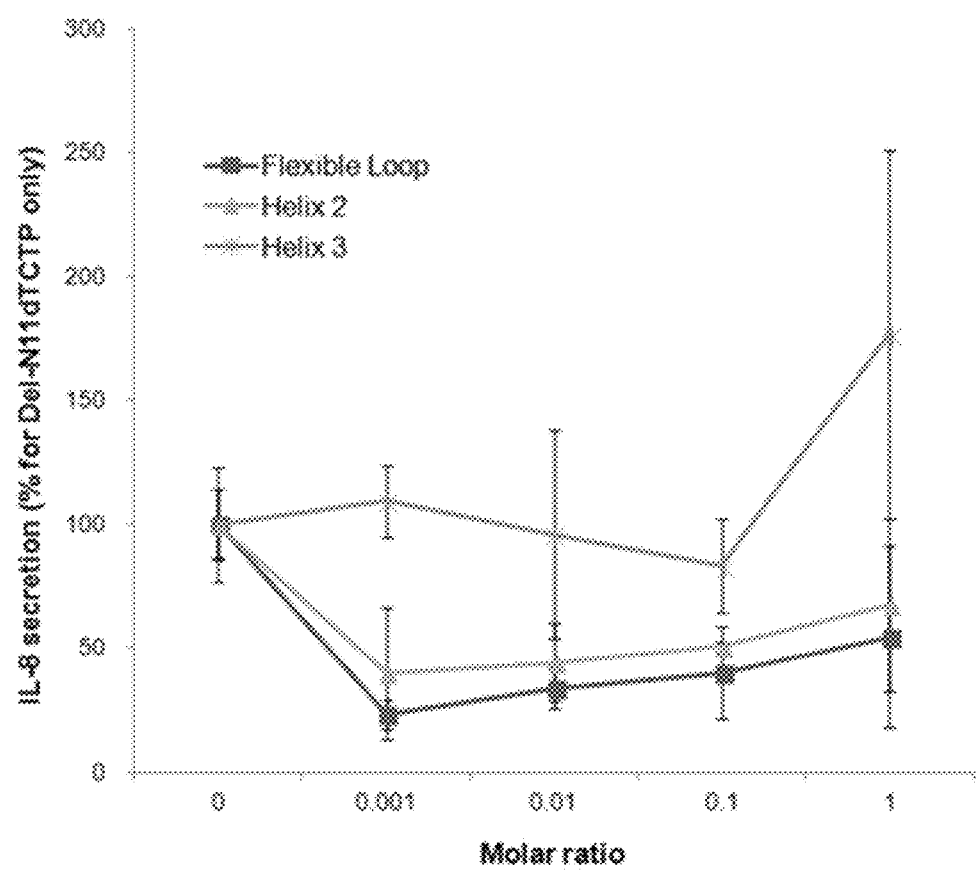
FIG. 4 is a graph illustrating the inhibitory effect of FL domain, Helix 2, or Helix 3 on Del-N11dTCTP in BEAS-2B cells.

As a result, as shown in FIG. 4, it was confirmed that the IL-8 secretion induced by Del-N11dTCTP was inhibited more strongly by FL domain and Helix 2 domain than by Helix 3 domain when the inhibition of IL-8 secretion mediated by Del-N11dTCTP in the presence of FL domain, Helix 2 domain, and Helix 3 domain was compared (FIG. 4).

Experimental Example 4: Analysis of Inhibitory Effect of Polyclonal Antibody Recognizing FL and H2 Domains on IL-8 Release The inhibitory effect on Del-N11dTCTP-mediated IL-8 secretion by the antibody recognizing FL and H2 domains constructed in Example 6 of the invention was investigated by treating the antibody to BEAS-2B cells.

Particularly, BEAS-2B cells were treated with anti-FL antibody and ani-H2 antibody at different concentrations. Then, Del-N11dTCTP-induced IL-8 secretion was compared. The BEAS-2B cells cultured in a 48-well plate were washed with 1% penicillin-streptomycin/BEBM (Lonza) twice, followed by serum starvation for 7 hours. The antibody diluted in PBS at the concentrations of 1 and 10 ng/ml was reacted with 70 µM Del-N11dTCTP at 37° C. for 2 hours. The reaction mixture was treated to the cells above. 20 hours later, the supernatant was obtained and the released IL-8 therein was quantified by ELISA.

Figure 5:
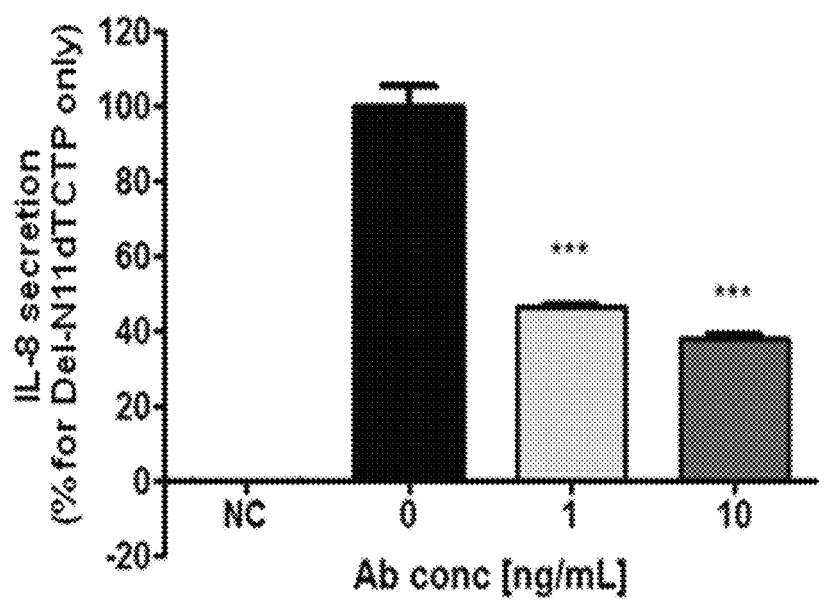
FIG. 5 is a graph illustrating the inhibitory effect of the antibody recognizing FL domain on Del-N11dTCTP in BEAS-2B cells.

As a result, as shown in FIG. 5, IL-8 secretion was not detected in the NC (negative control) group treated with 10 ng/ml of the antibody without Del-N11dTCTP. In the cell group treated with Del-N11dTCTP alone, IL-8 secretion was increased. In the group treated with the antibody specifically recognizing FL domain at the concentrations of 1 and 10 ng/ml, the Del-N11dTCTP mediated IL-8 secretion was reduced. Therefore, the inhibitory effect on IL-8 secretion of the antibody above was confirmed (FIG. 5).

Figure 6:
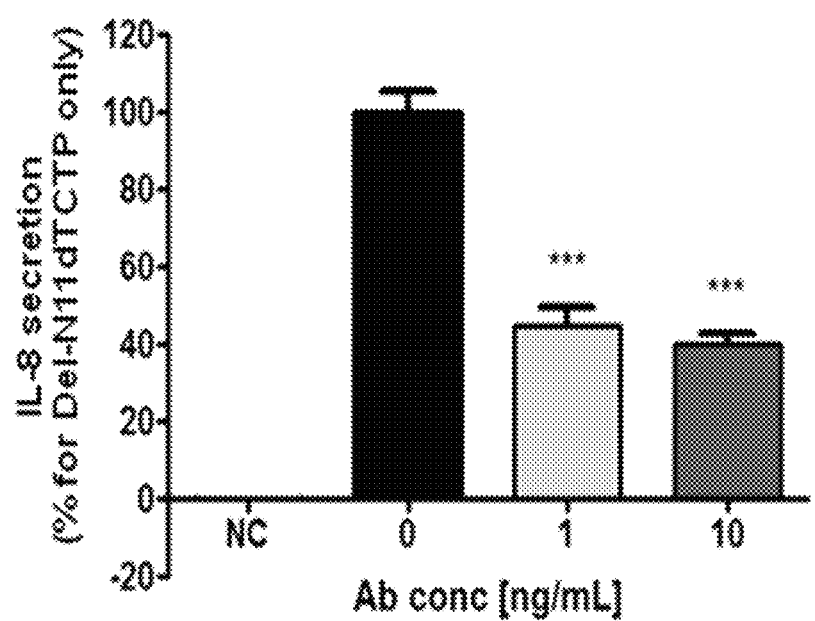
FIG. 6 is a graph illustrating the inhibitory effect of the antibody recognizing H2 domain on Del-N11dTCTP in BEAS-2B cells.

As shown in FIG. 6, another experiment was performed by using the antibody recognizing specifically H2 domain by the same manner as described in the above. As a result, the Del-N11dTCTP-mediated IL-8 secretion was reduced, suggesting that this antibody could also inhibit IL-8 secretion (FIG. 6).

Experimental Example 5: Investigation of Anti-Inflammatory Effect of FL Domain and H2 Domain in Asthma and Rhinitis Models The asthma and rhinitis models constructed in Example 7 were treated with FL and H2 domain at the concentration of 20 mg/kg in order to investigate whether or not those two HRF receptor binding domains could suppress pathophysiological lesion of asthma and rhinitis.

<5-1> Analysis of Bronchoalveolar Lavage Fluid (BALF)

The following experiment was performed in order to examine the inflammatory cells infiltrated in bronchoalveolar lavage fluid in the asthma and rhinitis animal models treated with FL and H2 domains.

Particularly, after cardiac blood collection in the animal model constructed in Example 7, bronchoalveolar lavage was performed. The airway was opened and a 20-gauge intravascular tube catheter was inserted through the opened airway, through which 0.8 ml of PBS containing 2% FBS was slowly injected three times and then recovered. The recovery rate was at least 80% and the recovered washing solution was centrifuged at 4° C. for 15 minutes at 1,000×g. The obtained supernatant was used for the detection of cytokine such as IL-5 or for the detection of TCTP protein. In the meantime, the precipitate was resuspended in 100 µℓ of PBS containing 2% FBS. The number of the inflammatory cells infiltrated in the washing solution was counted by using HEMAVET 950FS (Drew Scientific).

Figure 17A:
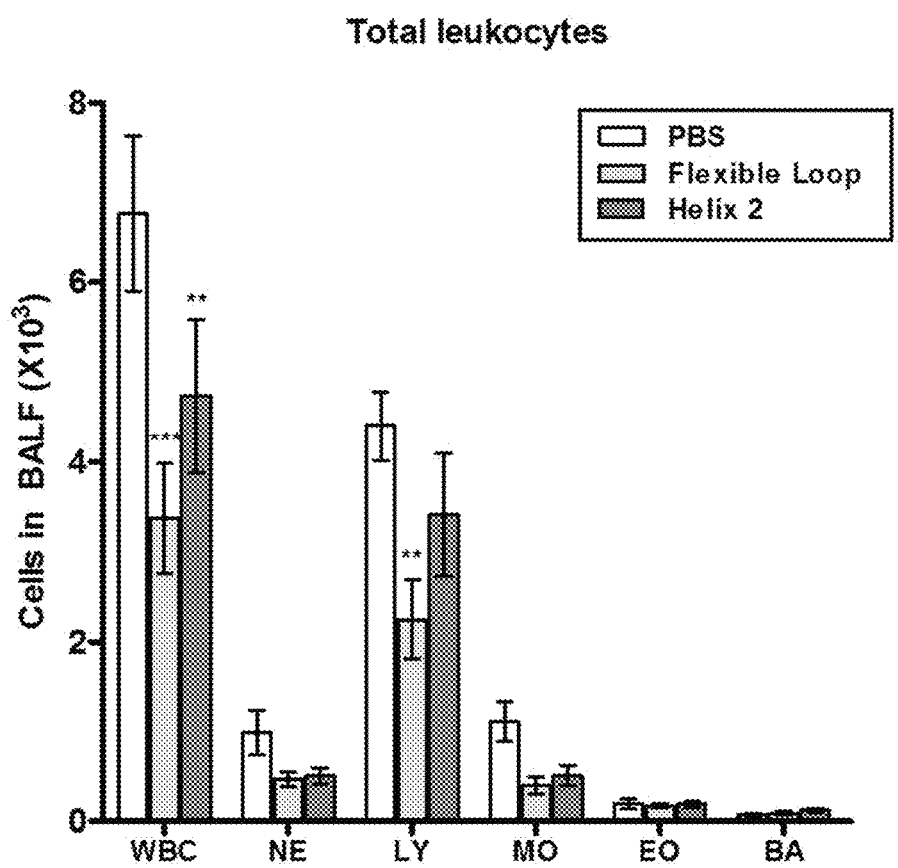
FIG. 17A, FIG. 17B, and FIG. 17C are graphs illustrating the comparison of the number of inflammatory cells infiltrated in bronchoalveolar lavage fluid of the asthma and rhinitis disease models when PBS, FL domain (20 mg/kg) and H2 domain (20 mg/kg) were administered thereto.
Figure 17B:
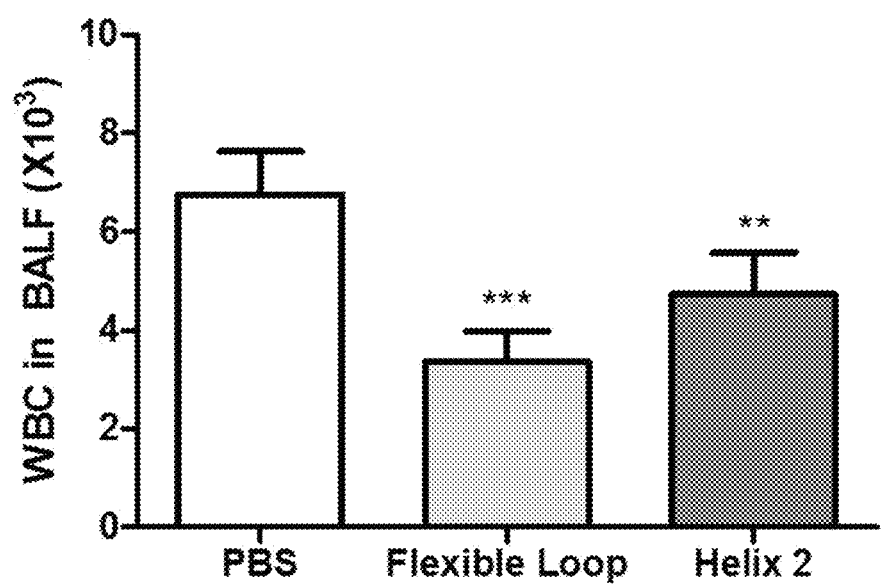
Figure 17C:
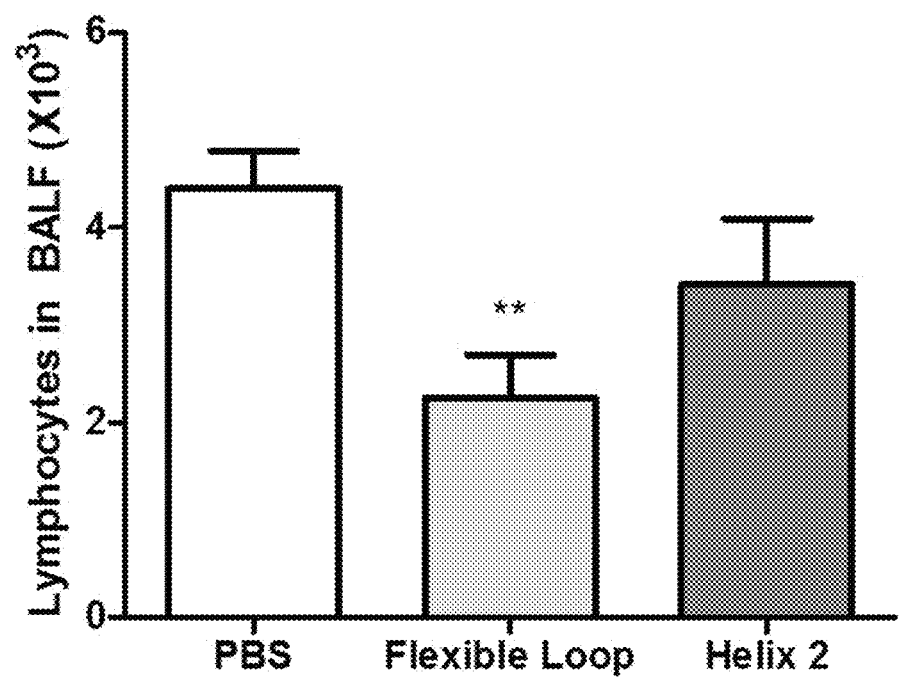
Figure 18:
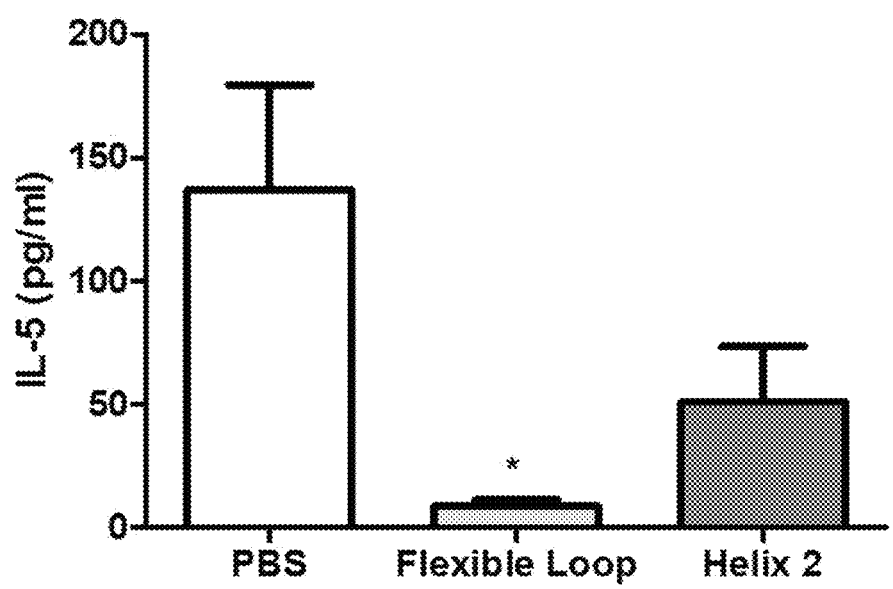
FIG. 18 is a graph illustrating the comparison of the suppressive effect on IL-5 secretion of PBS, FL domain (20 mg/kg), and H2 domain (20 mg/kg) in bronchoalveolar lavage fluid of the asthma and rhinitis disease models.

As a result, as shown in FIGS. 17 and 18, it was confirmed that the inflammatory cell infiltration in the bronchial alveoli induced by OVA was more frequent in the positive control group treated with PBS alone, whereas in the group treated with FL domain, both total cell number and leukocyte number were significantly lower (FIG. 17a). It was also confirmed that the total cell number was decreased in the group treated with H2 domain, compared with the positive control (FIGS. 17B and 17C).

The level of IL-5, the representative Th2 cytokine, was high in the positive control, but reduced in both groups treated with FL and H2 domains (FIG. 18).

From the above results, it was confirmed that FL domain was specifically effective. Later on, FL domain was injected to the asthma and rhinitis animal models at the concentrations of 1 mg/kg and 20 mg/kg, followed by investigating whether or not the anti-inflammatory effect of FL domain was dose-dependent.

Figure 20A:
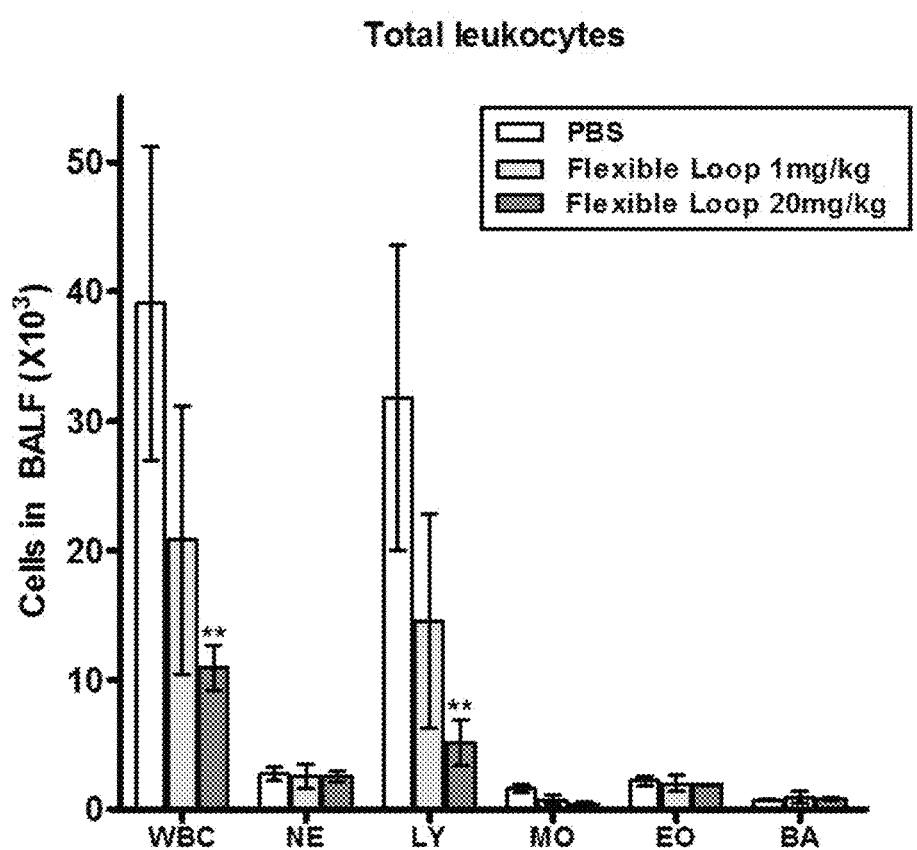
FIG. 20A, FIG. 20B, and FIG. 20C are graphs illustrating the comparison of the number of inflammatory cells infiltrated in bronchoalveolar lavage fluid according to the concentrations of PBS and FL domain in the asthma and rhinitis disease models.
Figure 20B:
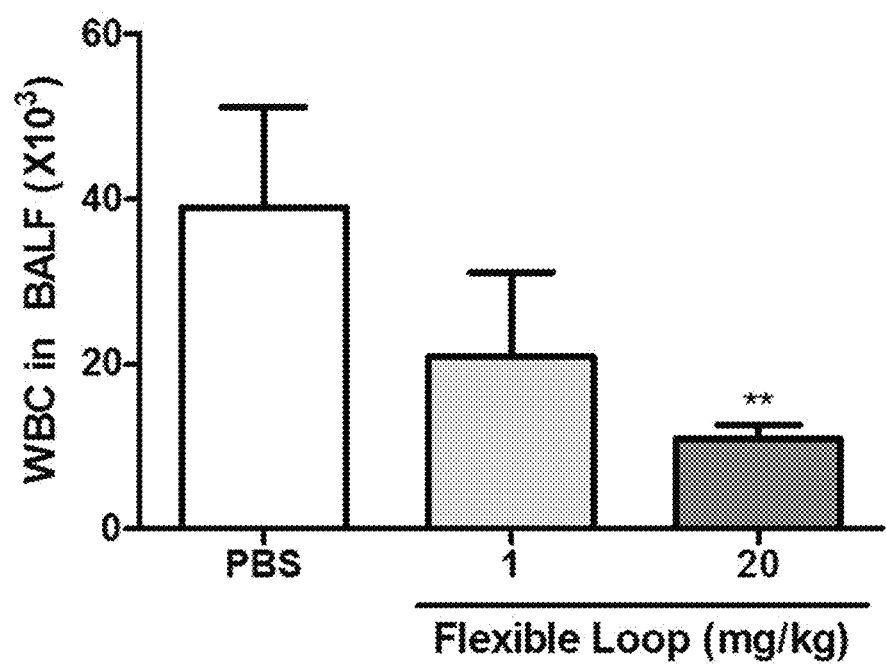
Figure 20C:
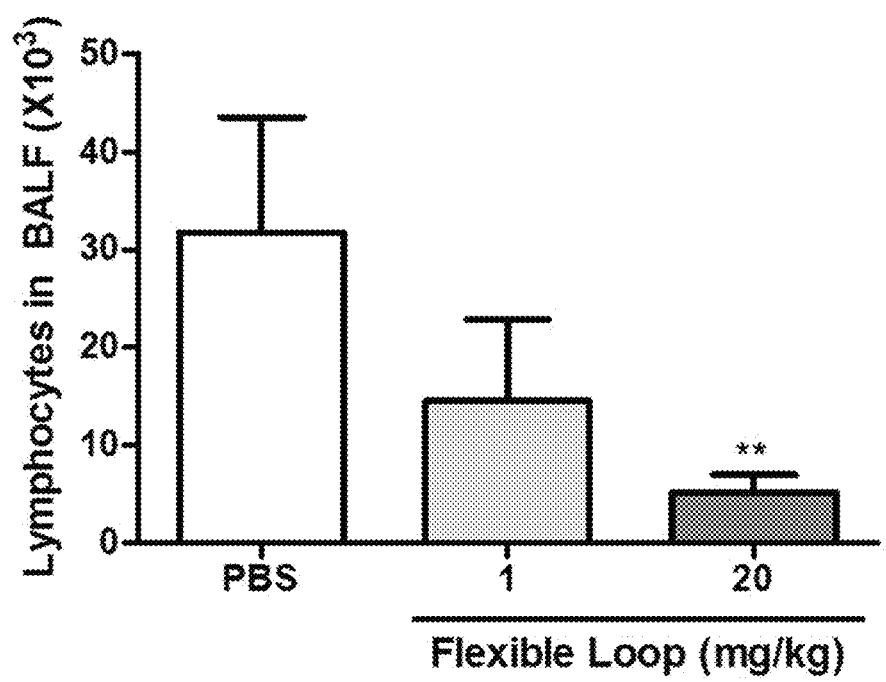
Figure 21:
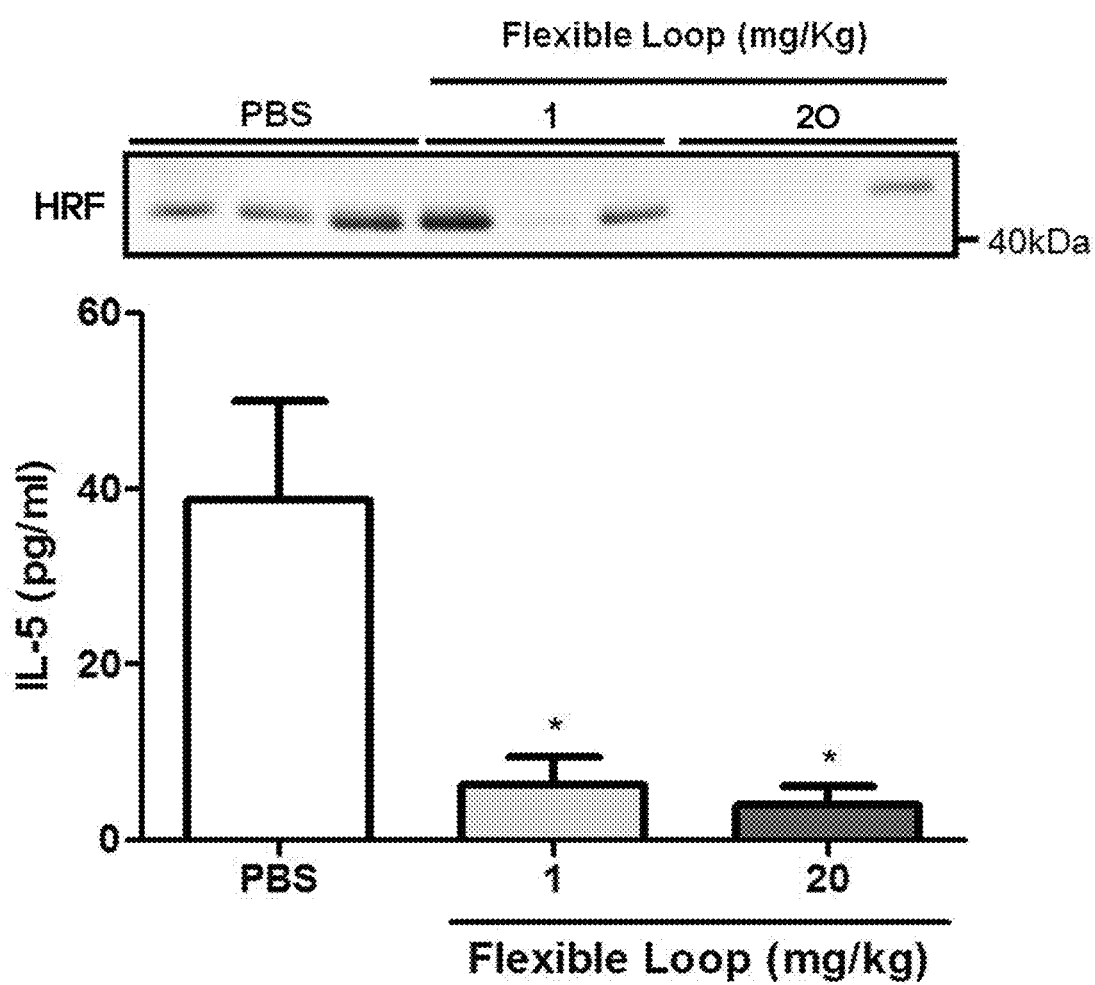
FIG. 21 is a diagram illustrating the inhibitory effect of PBS and FL domain on IL-5 secretion according to the treatment at various concentrations in bronchoalveolar lavage fluid of the asthma and rhinitis disease models and the result of immunoblotting detecting HRF.

As a result, as shown in FIG. 20, the inflammatory cells infiltrated in bronchoalveolar lavage fluid were reduced FL domain dose-dependently (FIG. 20a). The number of total cells and the level of lymphocytes were also significantly reduced in the group treated with 20 mg/kg of FL domain ($p<0.01$, FIGS. 20b and 20c). The level of IL-5 in bronchoalveolar lavage fluid was measured. As a result, it was confirmed that FL domain could inhibit IL-5 secretion even with as low concentration as 1 mg/kg (FIG. 21).

In addition, immunoblotting was performed with the bronchoalveolar lavage fluid by using TCTP-specific antibody to examine the relation of the anti-inflammatory effect of FL domain and the TCTP secreted extracellularly. As a result, in the positive control, TCTP dimer was detected (approximately 45 kDa) in all of the three test animals. In the meantime, in the group treated with FL domain, the level of TCTP dimer was reduced (FIG. 21).

<5-2> Evaluation of Ovalbumin-Specific IgE in Plasma

To confirm the level of ovalbumin-specific IgE in plasma of the asthma and rhinitis animal models, blood sampling and plasma isolation were performed as follows.

Particularly, upon completion of the experiment in Example 7, the mixture of zoletil (250 mg/kg) and rompun (50 mg/kg) was administered to the mouse via intraperitoneal injection to sacrifice the animal. 0.7~0.8 mL of blood was collected from the heart and placed in a heparinized tube. The blood sample stood at room temperature for 30 minutes~1 hour, followed by centrifugation at 1,000×g for 15 minutes to obtain plasma. The level of ovalbumin-specific IgE in the plasma was measured by ELISA. 100 μg of ovalbumin was dissolved in 0.05 M carbonate buffer (pH 9.6), which was distributed in a 96-well ELISA plate, followed by coating at 4° C. for overnight. Non-specific reaction was blocked by reacting the plate with TBS containing 1% BSA at room temperature for 30 minutes. The plasma sample was diluted (1:100), followed by reaction at room temperature for 1 hour, which was then washed with TBS containing 0.1% Tween-20. The HRF-conjugated anti-mouse IgE (SouthernBiotech) was diluted (1:8000), followed by reaction at room temperature for 1 hour. Then, the mixture was washed. TMB was treated thereto at room temperature. 10 minutes later, the reaction was terminated by adding 0.2 M $H_2SO_4$. Then, $OD_{450}$ was measured with an ELISA reader.

Figure 19:
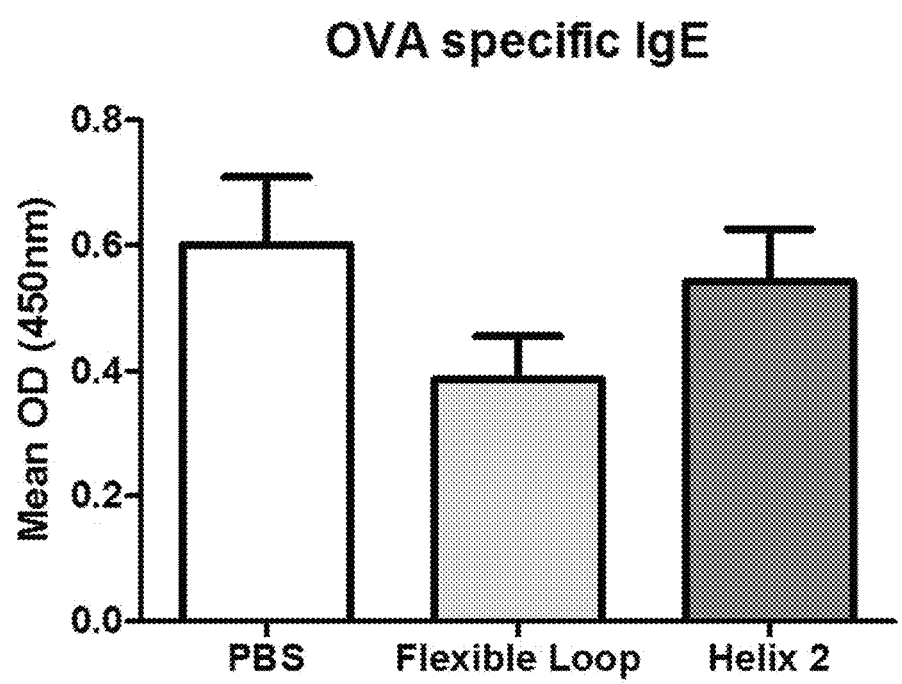
FIG. 19 is a graph illustrating the comparison of the suppressive effect on OVA specific IgE secretion of PBS and FL domain (20 mg/kg) in the asthma and rhinitis disease models.

As a result, as shown in FIG. 19, it was confirmed that the level of ovalbumin-specific IgE in the plasma was high in the positive control but it was reduced in the group treated with FL domain (FIG. 19).

Figure 23:
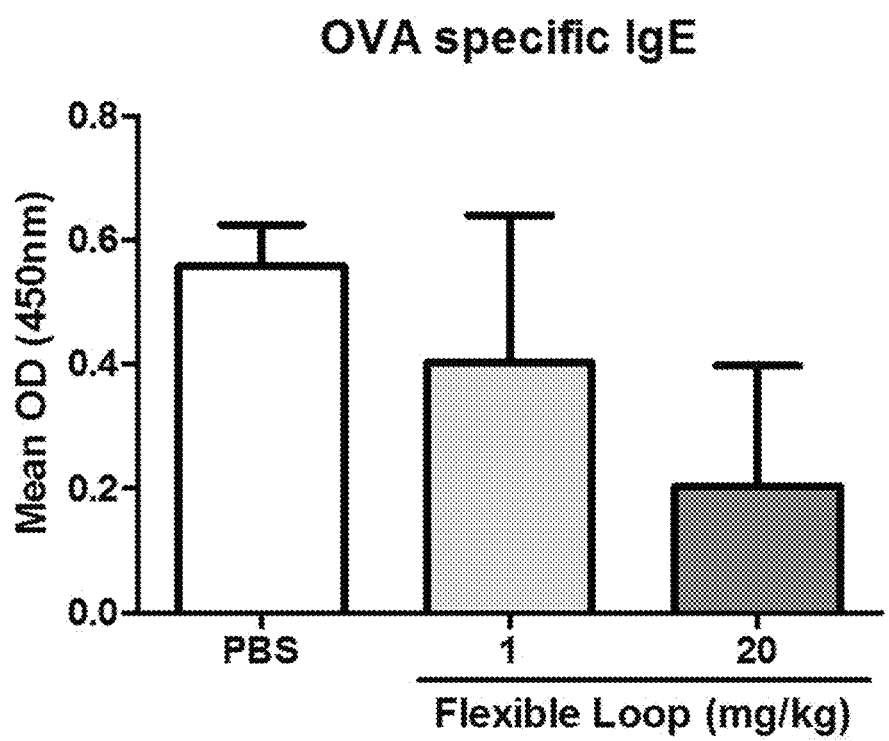
FIG. 23 is a graph illustrating the comparison of the inhibitory effect of PBS and FL domain on OVA-specific IgE secretion according to the treatment at various concentrations in blood plasma in the asthma and rhinitis disease models.

Since the level of ovalbumin-specific IgE in the plasma was highest in the positive control and was reduced by the treatment of FL domain dose-dependently, the inhibitory effect of FL domain on the antigen-specific IgE secretion was confirmed (FIG. 23).

<5-3> Analysis of Lung Tissue

To analyze the lung tissues in the asthma and rhinitis animal models, the following experiment was performed.

Particularly, bronchoalveolar lavage fluid was collected from the asthma and rhinitis animal models constructed in Example 7. The chest was dissected and the lung was extracted, which was washed with 4° C. PBS. The lung was cut to the appropriate size. Some of the lung pieces were fixed in PBS containing 4% paraformaldehyde (PFA) at room temperature via o/n fixation. On the next day, the fixed tissues were dehydrated to make paraffin blocks. Then, the paraffin was removed, and serial sections were made in the thickness of 5 μm on a slide, followed by Periodic acid-Shiff (PAS) staining for staining goblet cells. The remaining lung tissues were flash-frozen in liquid nitrogen. The protein in the tissue was extracted by using a lysis buffer, followed by immunoblotting to detect phospho-IκBα molecules in the lung tissue.

Figure 22:
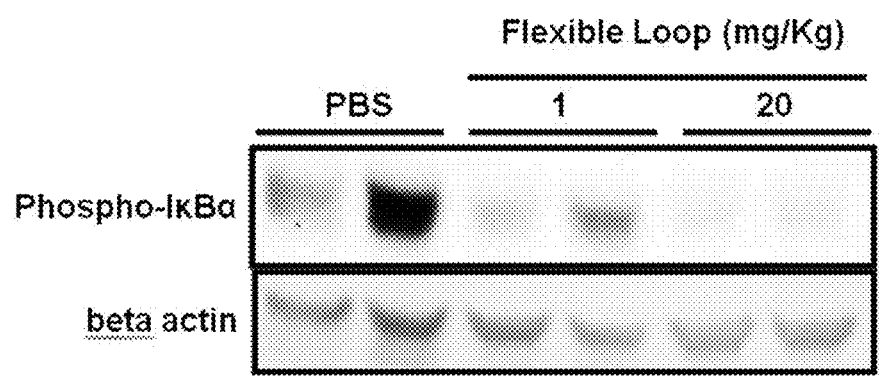
FIG. 22 is a diagram illustrating the result of immunoblotting investigating the inhibitory effect of PBS and FL domain on IκBα phosphorylation according to the treatment at various concentrations in lung tissue in the asthma and rhinitis disease models.

As a result, as shown in FIG. 22, the phospho-IκBα was detected most abundantly in the positive control group when the protein was extracted from the lung tissue in order to evaluate the inflammation improvement effect in the lung. In the FL domain treated group, the phospho-IκBα was decreased. Therefore, it was confirmed that the peptide of the invention had the inhibitory effect on IκBα phosphorylation (FIG. 22).

Experimental Example 6: Analysis of Inhibitory Activity of Polyclonal Antibody Recognizing C-Terminus Domain on IL-8 Release BEAS-2B cells were treated with the antibody recognizing C-terminus domain constructed in Example 8 in order to investigate whether or not the antibody could inhibit the Del-N11dTCTP-mediated IL-8 secretion.

Particularly, BEAS-2B cells were treated with Del-N11dTCTP (1 μg/mL) by the same manner as described in Experimental Example 4. At this time, the antibody diluted in PBS at the concentration of 40 nM was mixed with 1 μg/mL of Del-N11dTCTP at room temperature, followed by reaction for 10 minutes. The reaction mixture was treated to the cells above. 20 hours later, the supernatant was obtained and the separated IL-8 therein was quantified by ELISA.

Figure 24:
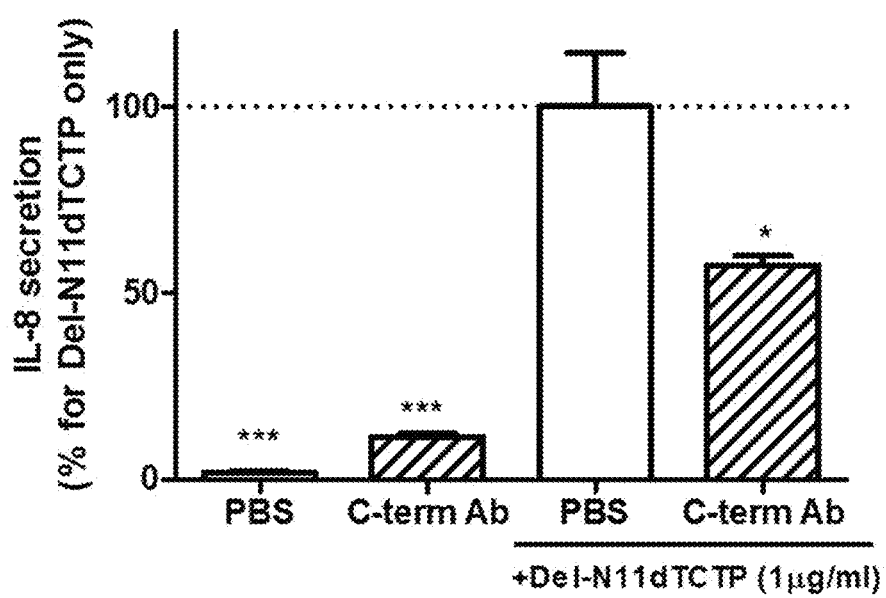
FIG. 24 is a graph illustrating the inhibitory activity of the antibody recognizing C-terminus domain against Del-N11dTCTP in BEAS-2B cells.

As a result, as shown in FIG. 24, in the group treated with PBS or 40 nM of the antibody alone without Del-N11dTCTP, the IL-8 secretion was low. In the group treated with PBS together with Del-N11dTCTP, the IL-8 secretion was increased. In the group treated with Del-N11dTCTP together with the antibody specifically recognizing C-terminus domain, the Del-N11dTCTP-mediated IL-8 secretion was reduced by 57.5%, suggesting that the antibody of the invention had the inhibitory effect on IL-8 secretion (FIG. 24).

Experimental Example 7: Analysis of Anti-Inflammatory Effect of Antiserum Against FL and C-Terminal Domains in Asthma and Rhinitis Animal Models The asthma and rhinitis animal models constructed in Example 7 were treated with the antiserum against FL and C-terminal domains to suppress the action of TCTP dimer, and then whether the pathophysiological lesion of asthma and rhinitis was inhibited thereby was investigated.

Figure 25:
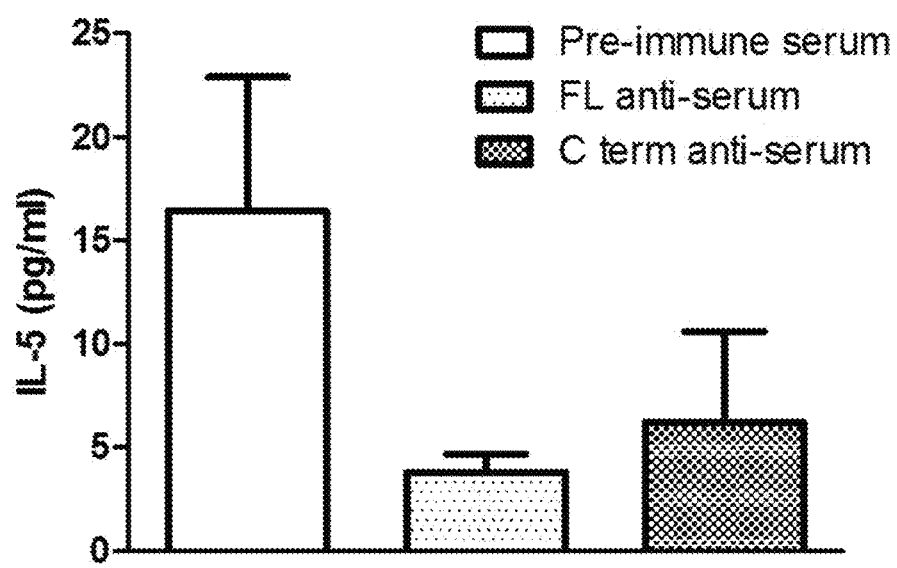
FIG. 25 is a graph illustrating the inhibitory effect of pre-immune serum and antiserum against FL domain or C-terminus domain on IL-5 secretion in bronchoalveolar lavage fluid in the asthma and rhinitis disease models.

As a result, the level of IL-5 in the bronchoalveolar lavage fluid was high in the negative control group. In the meantime, in the groups treated with the antiserum against FL and C-terminal domains displayed the reduced level of IL-5, suggesting that the antiserum of the invention had the inhibitory effect on IL-5 secretion (FIG. 25).

Experimental Example 8: Analysis of Anti-Inflammatory Effect of Anti-C-Terminus IgG in Asthma and Rhinitis Animal Models The asthma and rhinitis animal models constructed in Example 7 were administered with the IgG antibody against C-terminal domain via intranasal (i.n) administration or intraperitoneal (i.p) administration. The pathophysiological lesion of asthma and rhinitis, according to the administration through the two different routes above, was compared with that of the control treated with Pre-immune IgG.

Figure 27:
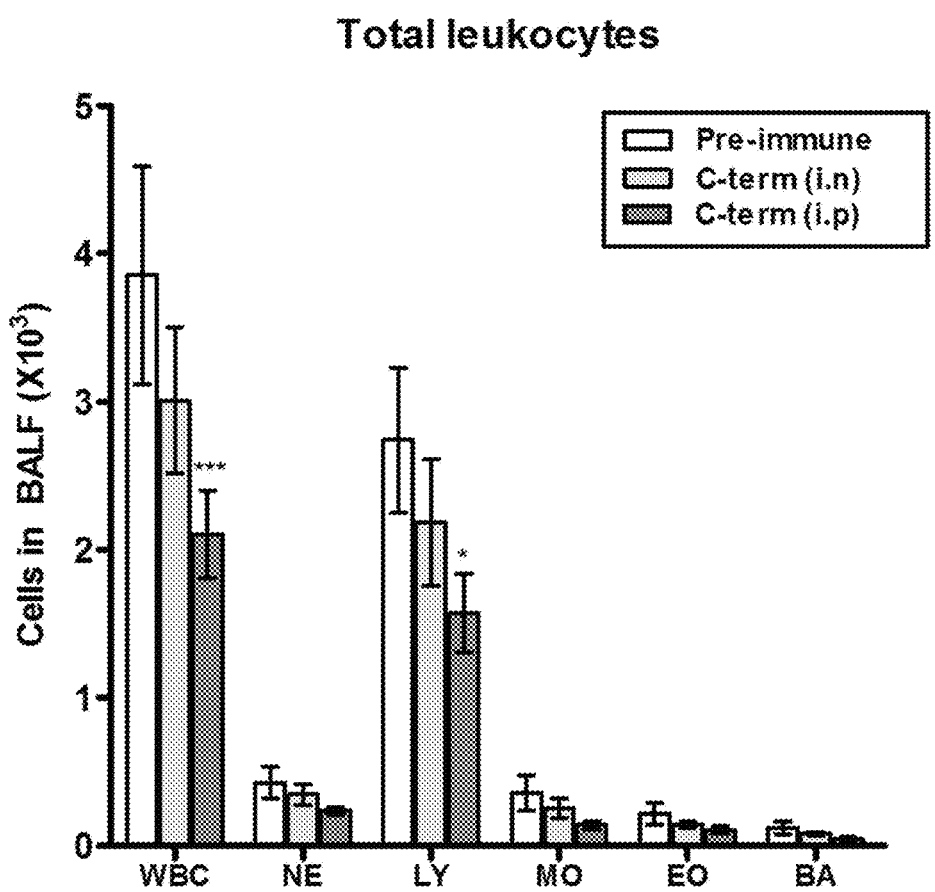
FIG. 27 is a diagram illustrating the comparison of the number of inflammatory cells infiltrated in bronchoalveolar lavage fluid according to the nasal or peritoneal administration of pre-immune IgG and anti C-terminus IgG antibody to the asthma and rhinitis disease models.
Figure 28A:
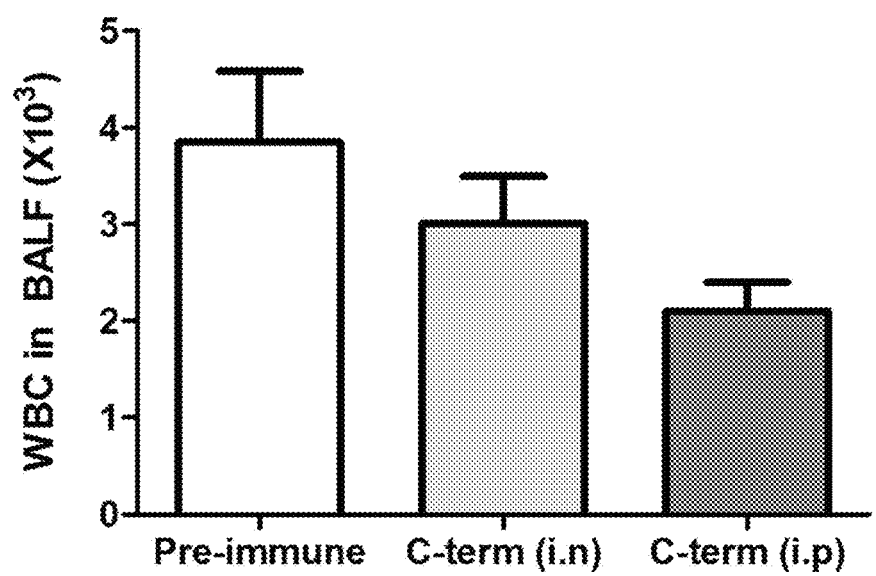
FIG. 28A, FIG. 28B, FIG. 28C, FIG. 28D, FIG. 28E, and FIG. 28F are graphs illustrating the comparison of the number of white blood cells (WBC), neutrophils (NE), lymphocytes (LY), monocytes (MO), eosinophils (EO), and basophils (BA) infiltrated in bronchoalveolar lavage fluid in the asthma and rhinitis disease models according to the nasal or peritoneal administration of pre-immune IgG and anti C-terminus IgG antibody thereto.
Figure 28B:
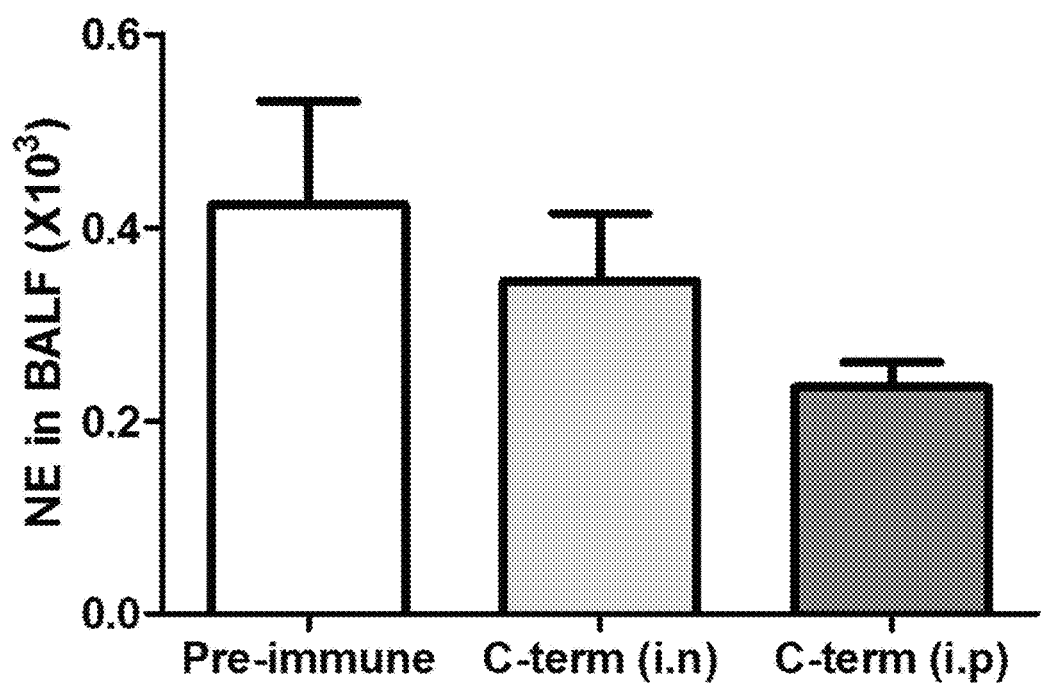
Figure 28C:
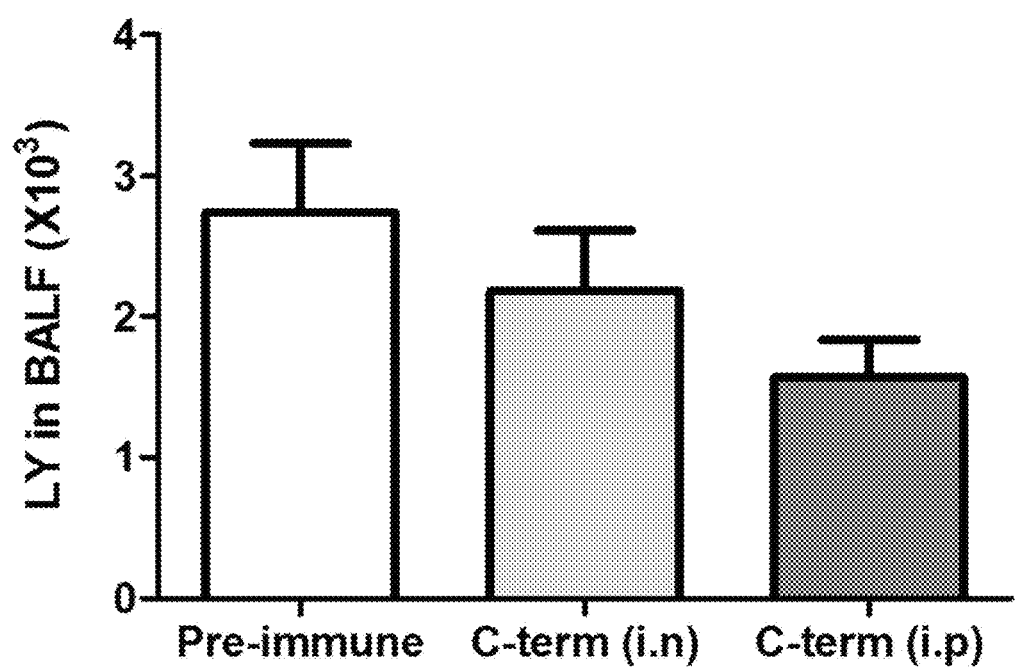
Figure 28D:
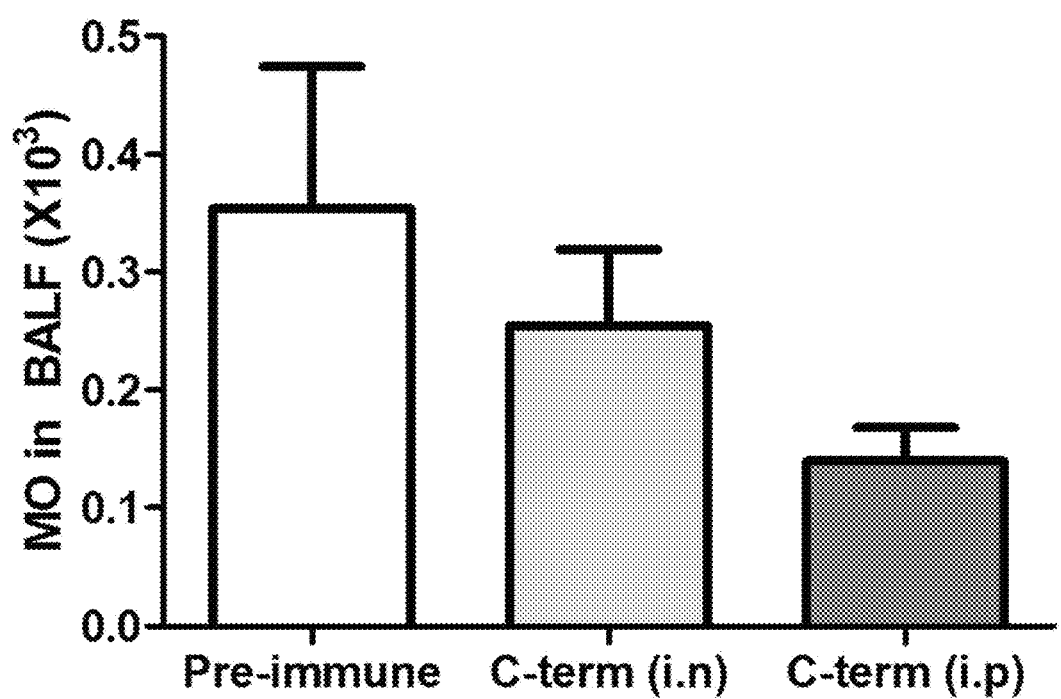
Figure 28E:
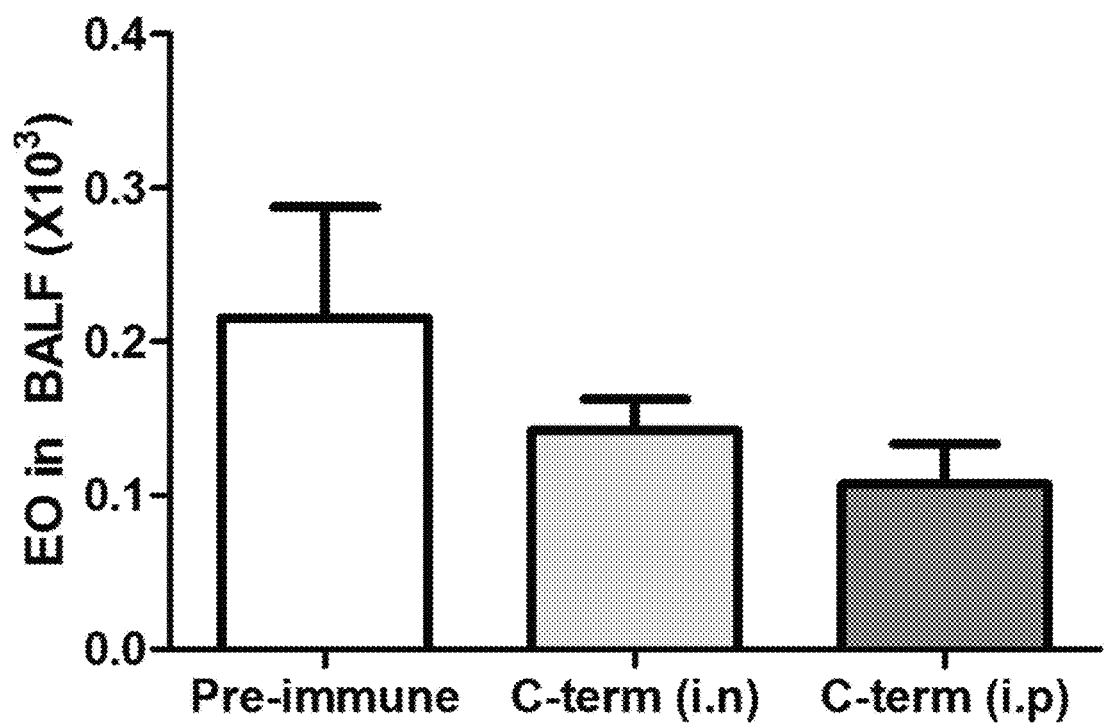
Figure 28F:
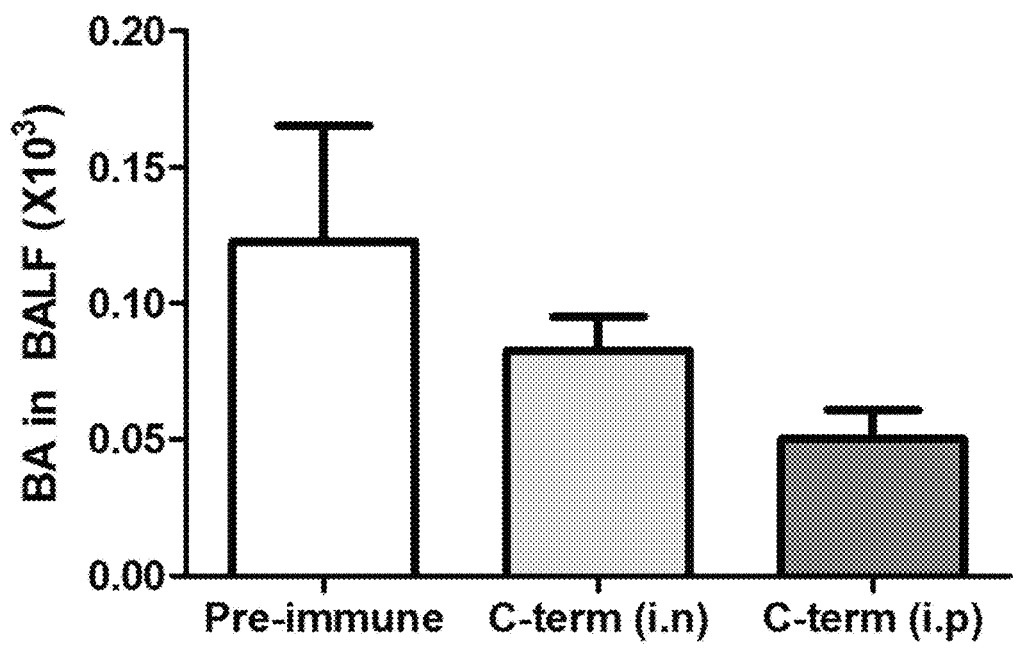

As a result, as shown in FIG. 26, the inflammatory cell infiltration induced by OVA was decreased in the bronchial alveoli of the group treated with the anti-C-terminal domain IgG antibody, compared with that of the negative control injected with Pre-immune IgG. When compared between the two different administration routes, the inflammatory cell infiltration was significantly reduced in the intranasal administration group [C-term (i.n)], compared with the intraperitoneal administration group [C-term (i.p)] (FIGS. 26-28).

Figure 29:
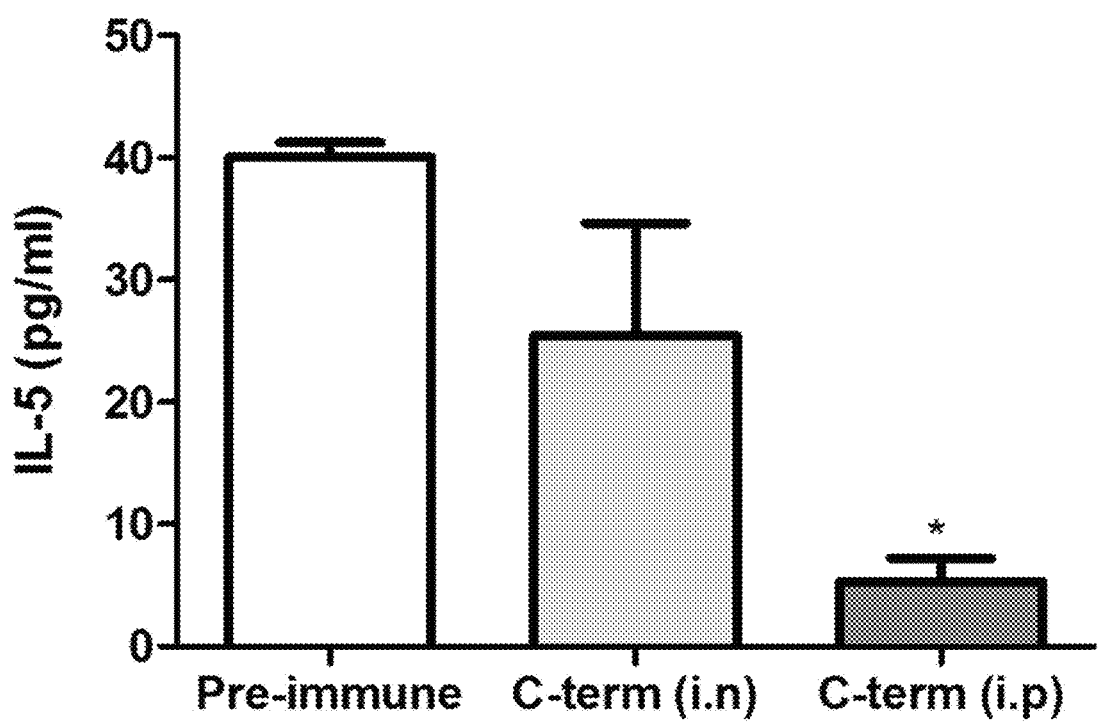
FIG. 29 is a diagram illustrating the comparison of IL-5 concentration secreted in bronchoalveolar lavage fluid in the asthma and rhinitis disease models according to the nasal or peritoneal administration of pre-immune IgG and anti-C-terminus IgG antibody thereto.

The IL-5 level in the bronchoalveolar lavage fluid was reduced in the group treated with IgG antibody against C-terminal domain. The level of IL-5 secreted in the bronchial alveoli was 63.6% in the intranasal administration group and 13.3% in the intraperitoneal administration group, suggesting that the intraperitoneal administration route was more effective in reducing IL-5 (FIG. 29).

Experimental Example 9: Confirmation of Preventive Effects on Rheumatoid Arthritis by dTBP2 in CIA (Collagen-Induced Arthritis) Mouse Model It was confirmed in this invention that the heptamer peptide (7mer-peptide) dTBP2 (p2 represented by SEQ. ID. NO: 24) of the present invention could inhibit the activity of HRF by binding to HRF, resulting in the preventive effects for rheumatoid arthritis.

Particularly, to induce CIA, 26 male DBA1/j mice at 7 weeks were purchased and adapted for at least one week. Bovine type 2 collagen (2 mg/ml, Chondrex) and complete Freund's adjuvant (CFA containing 2 mg/ml *M. tuberculosis*, Chondrex) were mixed at the ratio of 1:1. 150 µl of the mixture was slowly injected through intradermal injection in 2 cm below the base of the tail (day 0). 3 weeks later, the secondary injection was performed. At this time, incomplete Freund's adjuvant (IFA), instead of CFA, was mixed with bovine type 2 collagen solution at the ratio of 1:1. 100 µl of the mixture was slowly injected through intradermal injection in the base of the tail. 9 mice were administered with vehicle alone, 8 mice were administered with 5 mg of dTBP2, and 9 mice were administered with 25 mg of dTBP2. 1.5 mg of dTBP2 was dissolved in 1 ml of PBS for the administration. From 21 days before arthritis was developed, the administration was performed three times a week. Arthritic clinical scores of 0 to 4 points (0 to 16 points total) were assessed for each foot twice weekly. At the same time, the thickness of both ankles was measured using an electronic caliper, and the changes in thickness were presented with relative percentage to the thickness at the first measurement.

Figure 30:
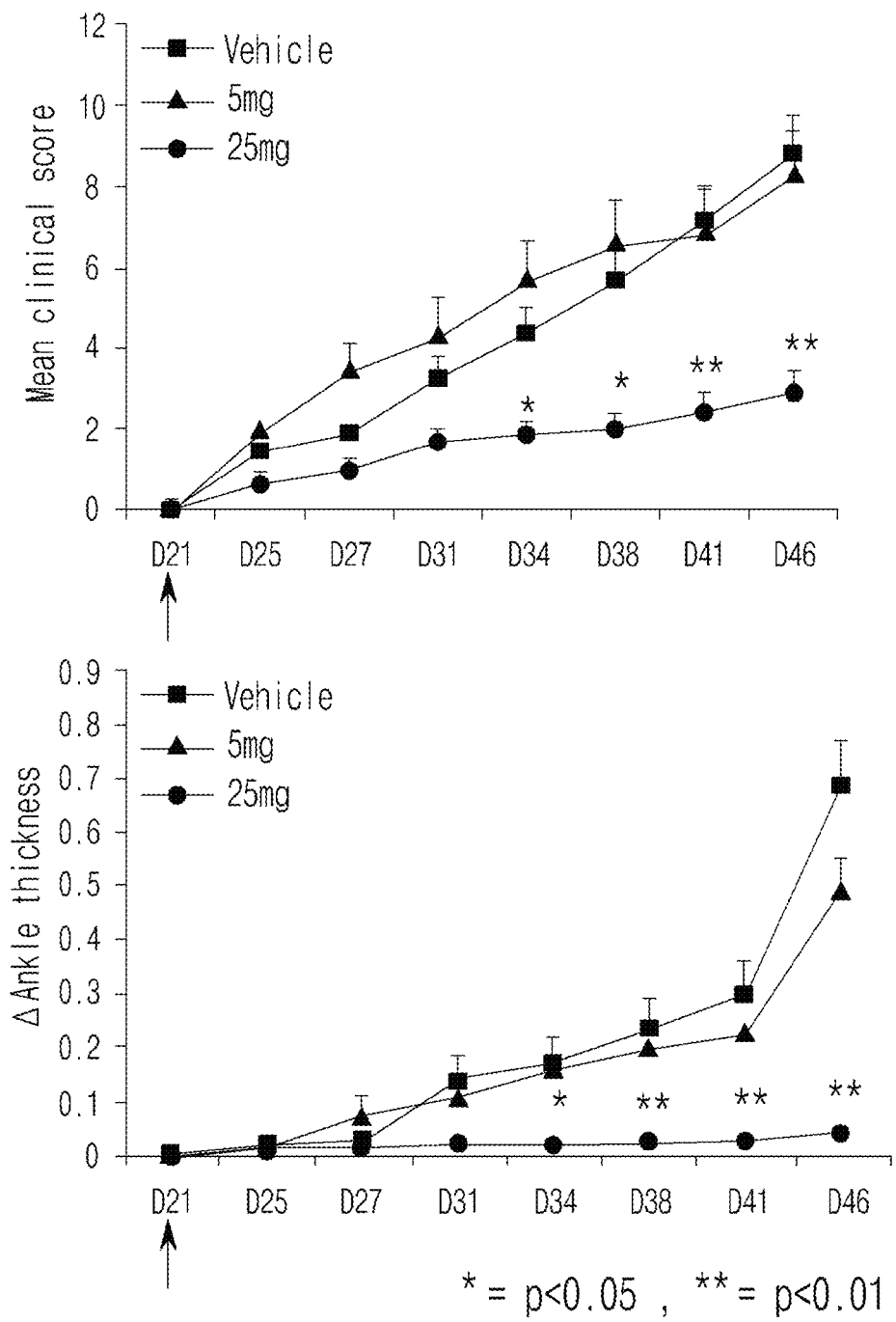
FIG. 30 is a graph illustrating the effect of dTBP2, the 7-mer peptide, on the prevention of rheumatoid arthritis in the rheumatoid arthritis model.

As a result, as shown in FIG. 30, the development of rheumatoid arthritis was inhibited more significantly in the group treated with 25 mg of dTBP2 than in the group treated with either vehicle alone or 5 mg of dTBP2. On day 31, the incidence rate was inhibited at least 50% in the group treated with 25 mg of dTBP2, compared with the group treated with vehicle alone or 5 mg of dTBP2. On day 46, the incidence rate was inhibited at least 70% in the group treated with 25 mg of dTBP2, compared with the group treated with vehicle alone or 5 mg of dTBP2. As a result of measuring the joint thickness, which is a clinical symptom index of arthritis, it was confirmed that the joint thickness was continuously increased until day 41 and rapidly increased from day 41 to day 46 in the group treated with vehicle alone or 5 mg of dTBP2. In the meantime, the joint thickness was almost as same as that of the normal until day 46 in the group treated with 25 mg of dTBP2, suggesting that the dTBP2 of the present invention had the preventive effects on rheumatoid arthritis (FIG. 30).

Experimental Example 10: Confirmation of Treatment Effect of dTBP2 in Rheumatoid Arthritis Using CIA Mouse Model It was confirmed that when the heptamer peptide (7mer-peptide), dTBP2 of the present invention bound to HRF, it suppressed HRF activation, resulting in the treatment effect on rheumatoid arthritis.

Particularly, CIA was induced in DBA1/j mice by the same manner as described in Experimental Example 9. Based on the mean arthritis clinical score of 5, dTBP2 was administered from day 41. At this time, 4 mice were administered with vehicle alone, 5 mice were administered with 5 mg of dTBP2, and 5 mice were administered with 25 mg of dTBP2. 1.5 mg of dTBP2 was dissolved in 1 ml of PBS for the administration. The administration was performed three times a week and the measurement was performed twice a week.

Figure 31:
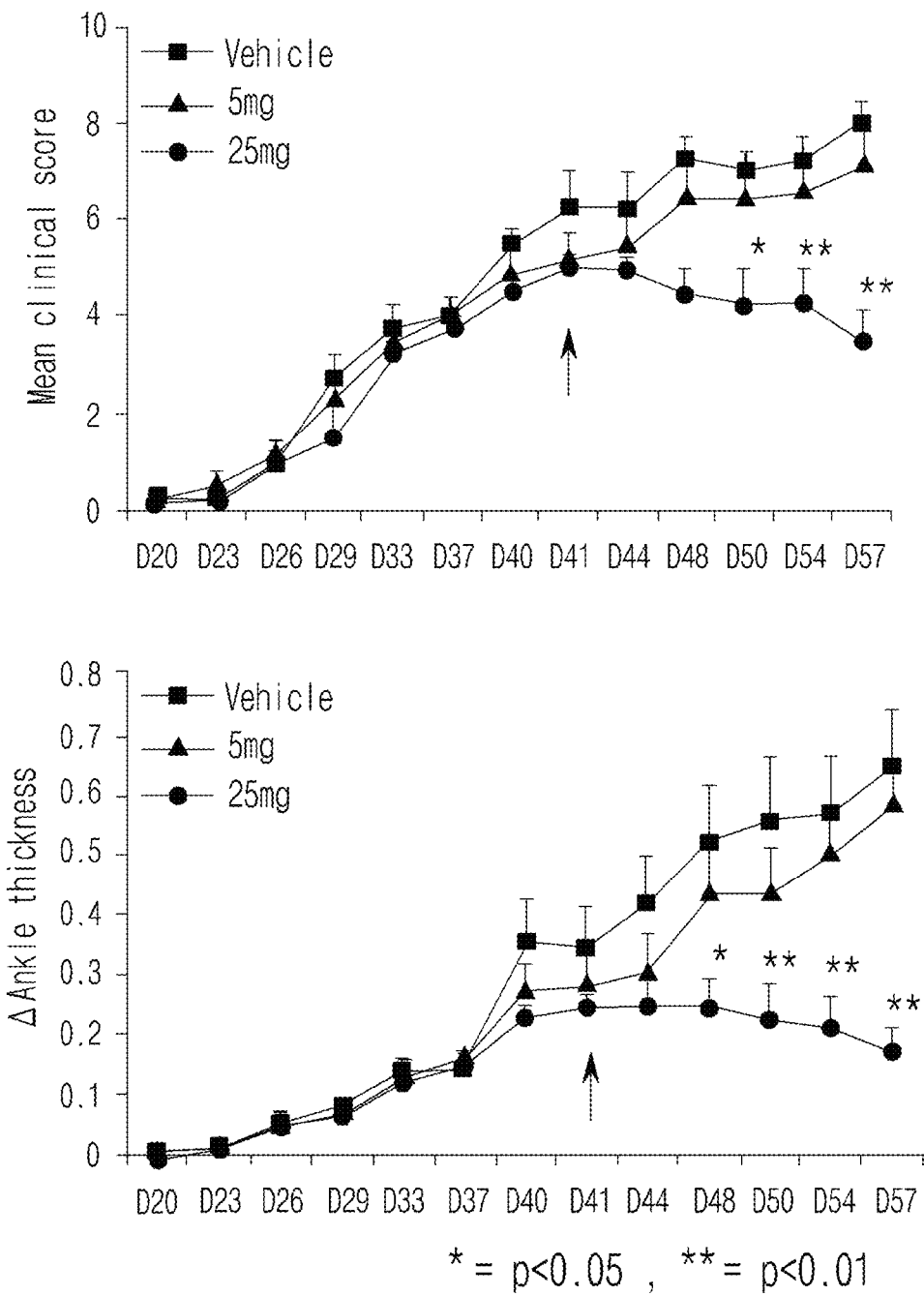
FIG. 31 is a graph illustrating the effect of dTBP2 on the treatment of rheumatoid arthritis in the rheumatoid arthritis model.

As a result, as shown in FIG. 31, the clinical score was getting lower in the group treated with 25 mg of dTBP2, compared with the group treated with vehicle alone or 5 mg of dTBP2, suggesting that the symptoms were improved and therefore the treatment effect on rheumatoid arthritis was confirmed. From the measurement of the joint thickness, a clinical symptom index, it was confirmed that the thickness was reduced in the group treated with 25 mg of dTBP2 continuously after day 41, while the joint thickness in the group treated with vehicle alone or 5 mg of dTBP2 was continuously increased, suggesting that the dTBP2 of the present invention had the treatment effect on rheumatoid arthritis (FIG. 31).

Experimental Example 11: Confirmation of Effect of dTBP2 on Atopic Dermatitis in Atopic Dermatitis Mouse Model It was confirmed in this invention that the dTBP2 of the present invention could inhibit the binding between HRF and its receptor or the activation thereof by binding to HRF, so that it could treat the atopic dermatitis.

Particularly, 5 week old specific pathogen free female NC/Nga mice were purchased from Orientbio Inc. (Seoul, Korea), which were adapted for 1 week. After depilating with a hair removal agent, Biostir® AD ointment (Biostir, Japan) was used to induce atopic dermatitis on the dorsal skin. That is, hair was removed from the back of the mouse, on which 150 µl of 4% SDS dissolved in PBS was applied. After 2-3 hours of natural dry, 100 mg of Biostir® AD cream was evenly applied on the back skin and the ear skin of the mouse. The cream was applied twice a week, 6 times total for 3 weeks. It was confirmed that the skin layer of the mouse became thick and keratin was formed on the back skin.

To investigate the effect of dTBP2 on atopic dermatitis in the atopic dermatitis-induced mouse, the positive control was administered with PBS, the comparative experimental group was administered with protopic ointment (Astellas Pharma Manufacturing Inc., USA), and the experimental group was treated with dTPB2. On day 0, PBS (subcutaneous injection, 25 mg/kg), protopic ointment (skin application, 100 mg/mouse) and dTBP2 (subcutaneous injection, 25 mg/kg) were respectively applied. On day 1, 100 mg of Biostir® AD cream was applied thereto. On day 2 and day 3, PBS, protopic ointment, and dTBP2 were treated thereto by the same manner as performed on day 0. On day 4, 100 mg of Biostir® AD cream was applied thereto. On day 5, PBS, protopic ointment, and dTBP2 were treated thereto by the same manner as performed on day 0.

Figure 32A:
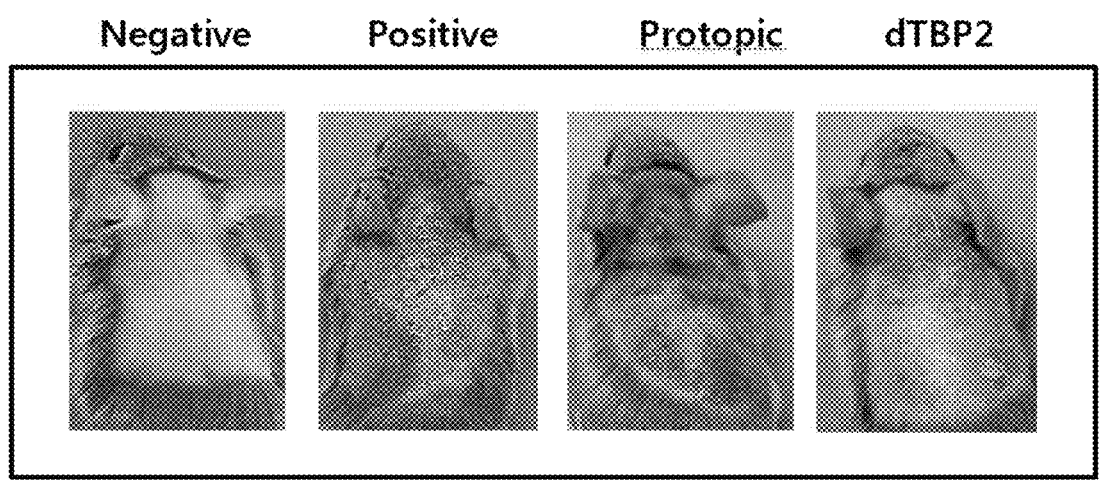
FIG. 32A is a diagram illustrating the improvement effect of dTBP2 in the atopic dermatitis model, observed with the naked eye.

As a result, as shown in FIG. 32a, the mice treated with protopic ointment and dTBP2 were visually confirmed to have a lesser degree of atopy than the control group (FIG. 32a).

Figure 32B:
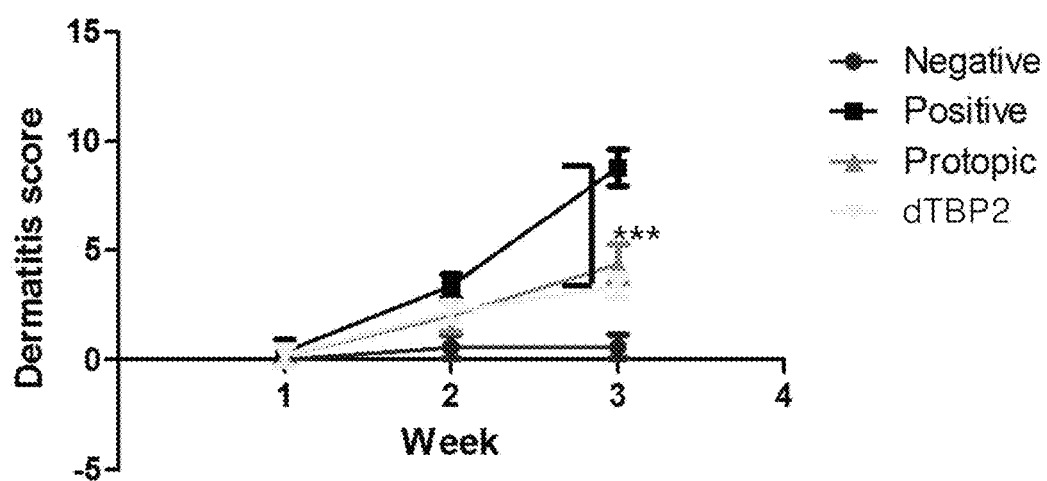
FIG. 32B is a graph illustrating the improvement effect of dTBP2 in the atopic dermatitis model.

Atopic symptoms were observed and presented as points according to the atopic index such as erythema, drying, excoriation, edema, and erosion, based on which a graph was made (FIG. 32b, 0: no symptoms, 1: weak symptoms, 2: median symptoms, 3: severe symptoms). It was confirmed on the graph that atopy was minor in the group treated with protopic ointment and dTBP2, compared with the control.

Figure 33:
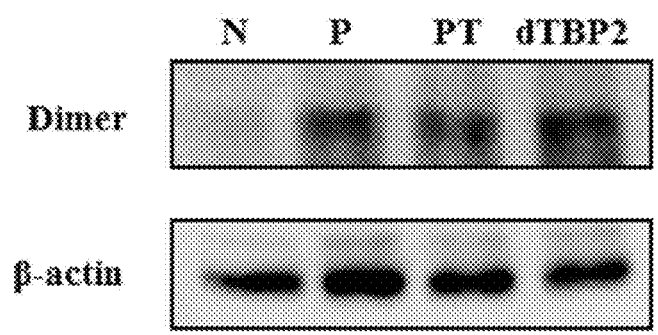
FIG. 33 is a diagram illustrating the increase of HRF in the atopic dermatitis model.

It was confirmed by Western blotting that dTCTP (46 kDa), the histamine releasing factor, was significantly increased in the skin tissues of the positive control group induced with atopic allergy using Biostir AD cream, the group treated with PBS, the group treated with protopic ointment, and the group treated with dTBP2 (FIG. 33).

Figure 34A:
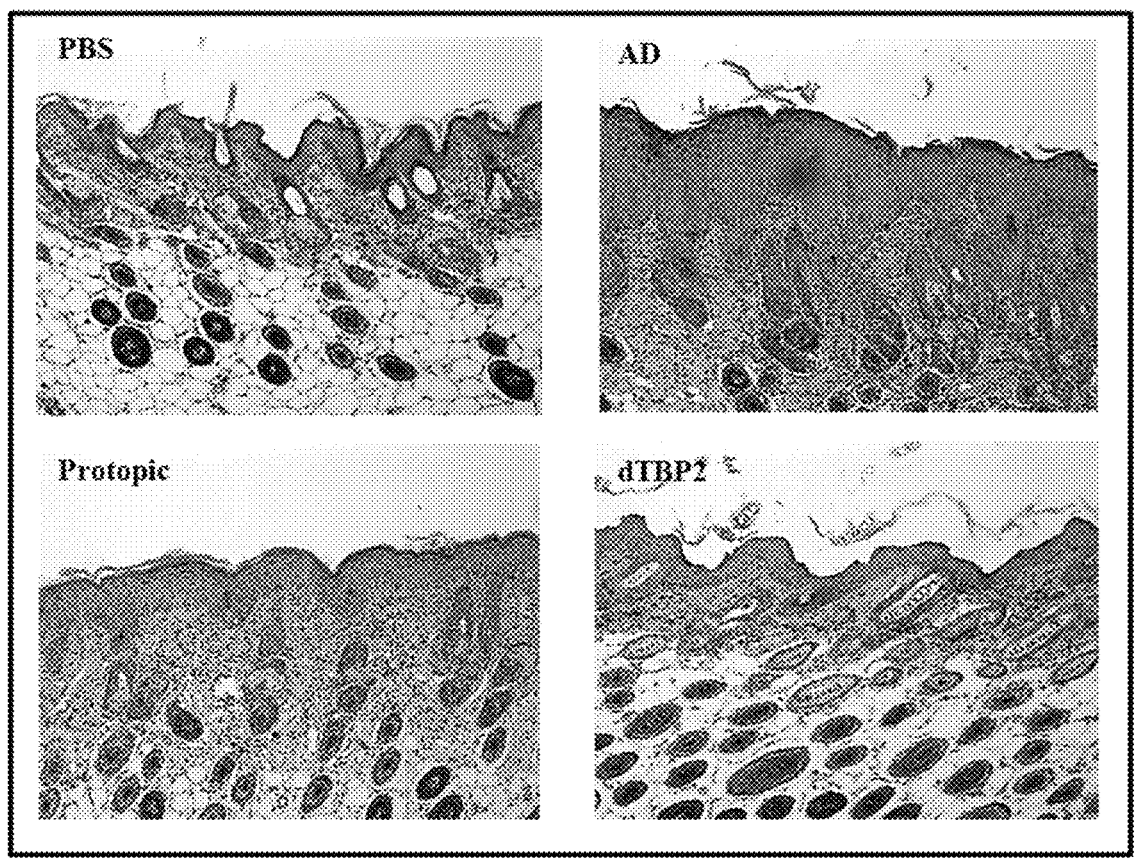
FIG. 34A is a diagram illustrating the result of H&E staining to evaluate the effect of dTBP2 histologically in the atopic dermatitis model.
Figure 34B:
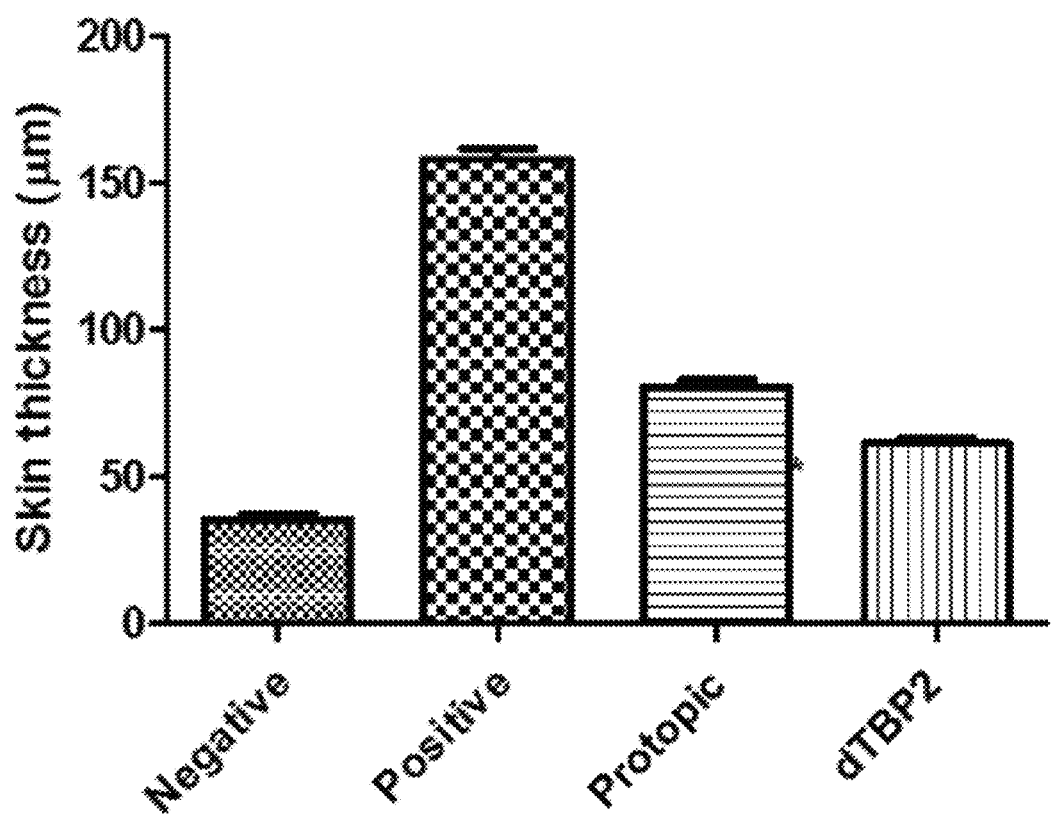
FIG. 34B is a graph illustrating the effect of dTBP2 on the skin thickness in the atopic dermatitis model.
Figure 34C:
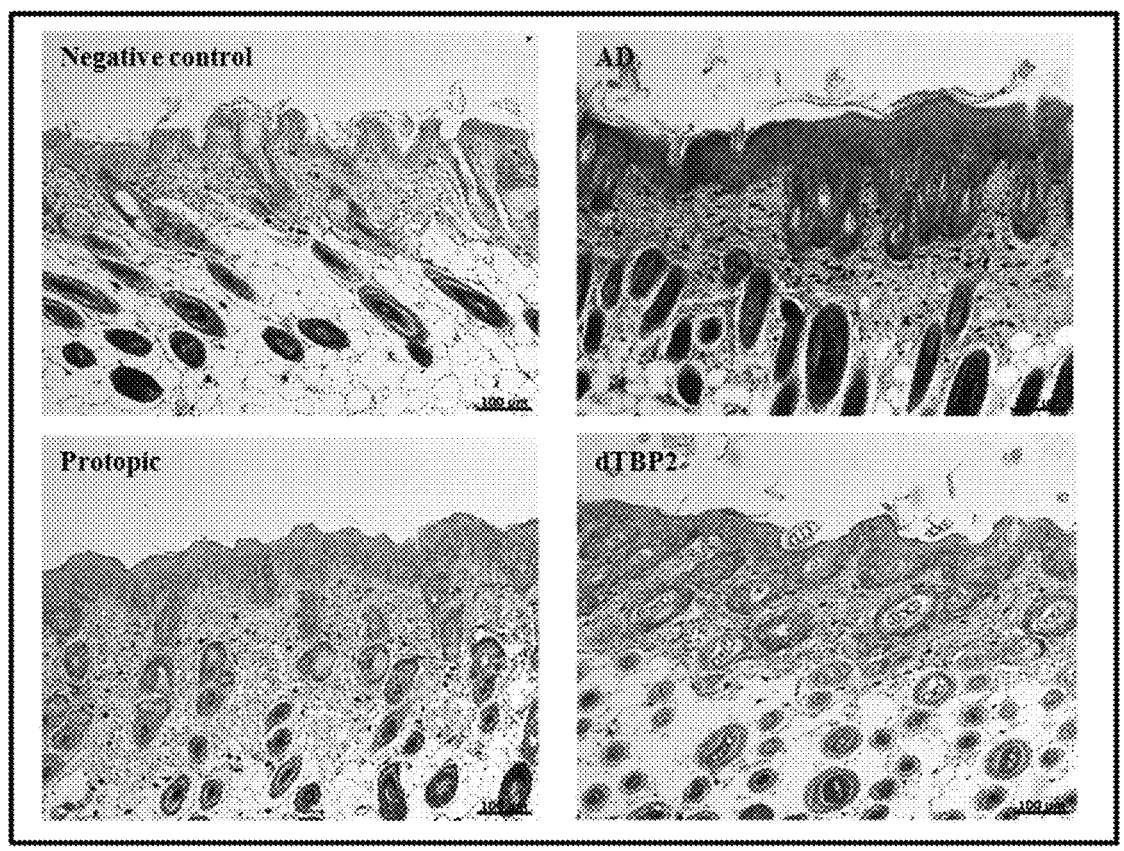
FIG. 34C is a diagram illustrating the histological effect of dTBP2 on the infiltration of mast cells in the atopic dermatitis model.
Figure 34D:
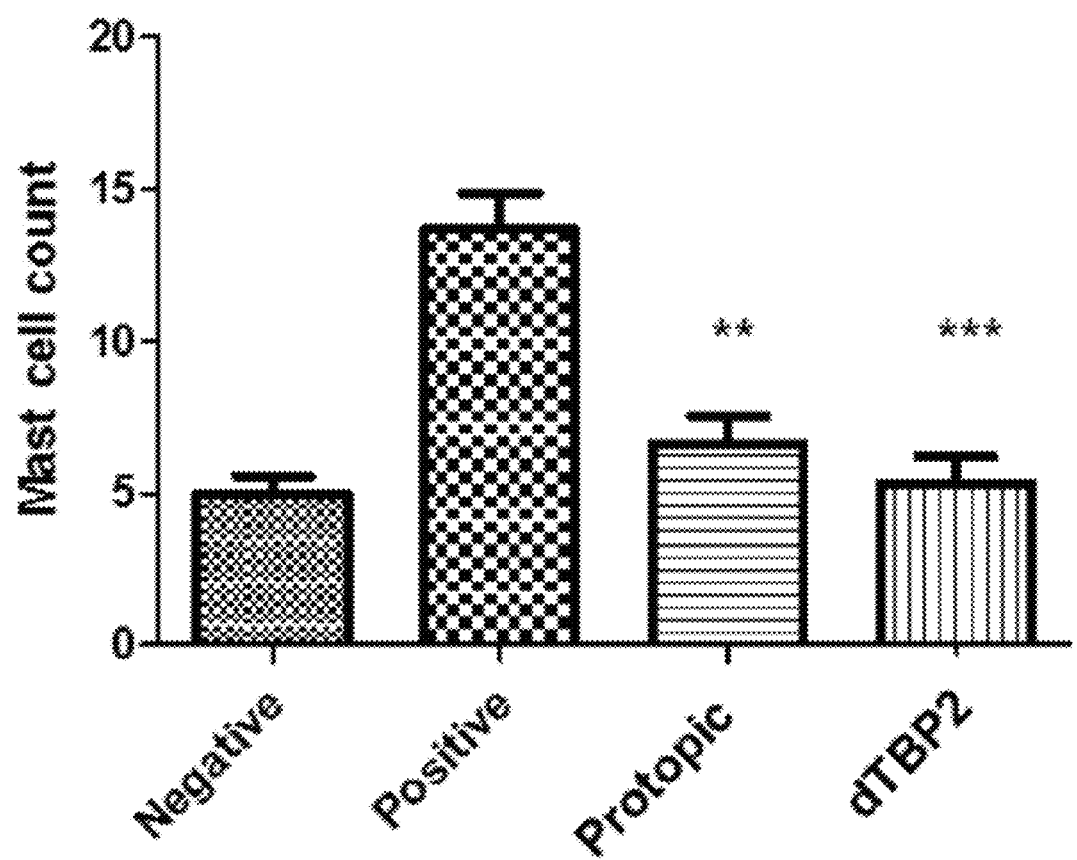
FIG. 34D is a graph illustrating the effect of dTBP2 on the infiltration of mast cells in the atopic dermatitis model.

Once atopic allergy is induced, the stratum corneum and skin layer become thick and the infiltration of inflammatory cells is increased. For the histological evaluation, hematoxylin/eosin staining and toluidine blue staining were performed. The thickness of the skin and the infiltration of immune related inflammatory cells were observed under microscope. As a result, the atopic symptoms including the thick stratum corneum were improved in the groups treated with protopic ointment and dTBP2, compared with the control group treated with PBS alone (FIGS. 34a and 34b). The infiltration of mast cells was also significantly reduced in the groups treated with protopic ointment and dTBP2, compared with the positive control group (FIGS. 34c and 34d).

Figure 35:
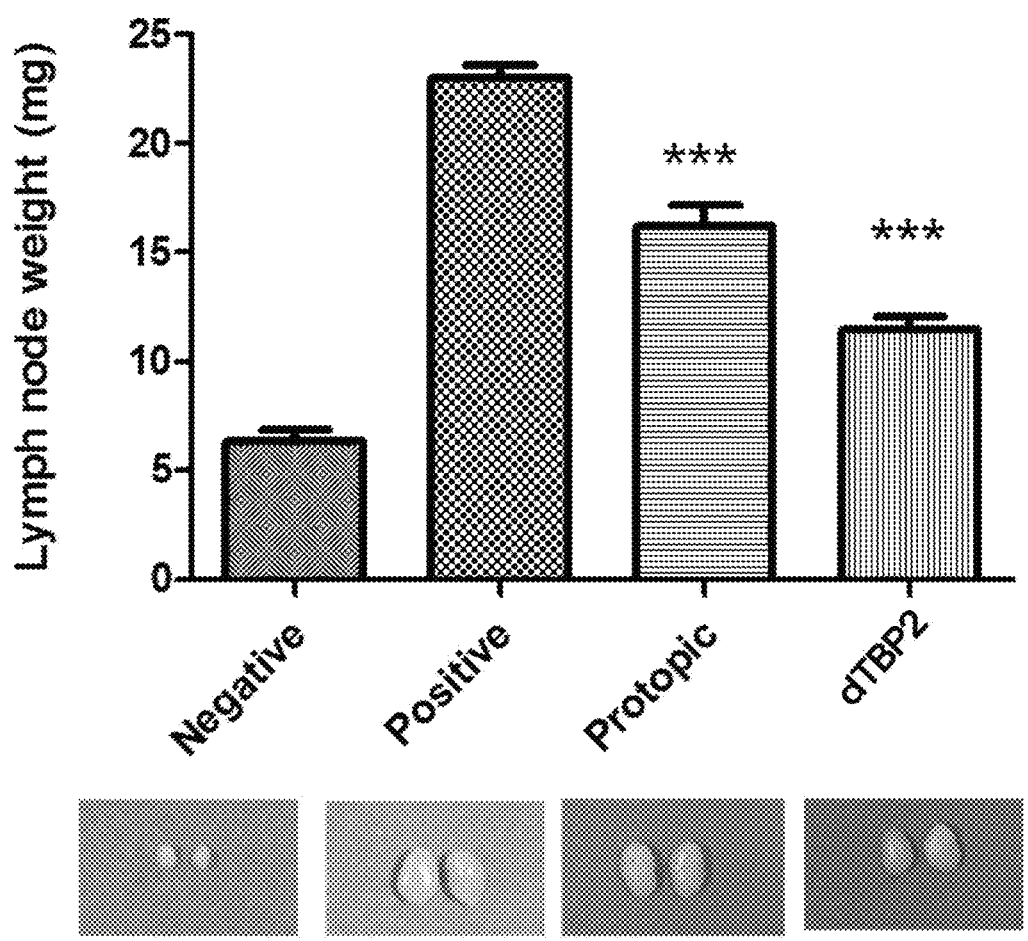
FIG. 35 is a diagram illustrating the effect of dTBP2 confirmed by lymph node assay.

Lymph node assay examining the effect of an antigen or a drug by observing the changes of lymph node weight was performed to investigate inflammatory reaction induced by skin sensitizing materials. The lymph node of the group treated with PBS was increased in both weight and size, compared with the normal lymph node, and the lymph node of the group treated with protopic ointment or dTBP2 was smaller in both weight and size than that of the PBS treated group (FIG. 35).

Figure 36:
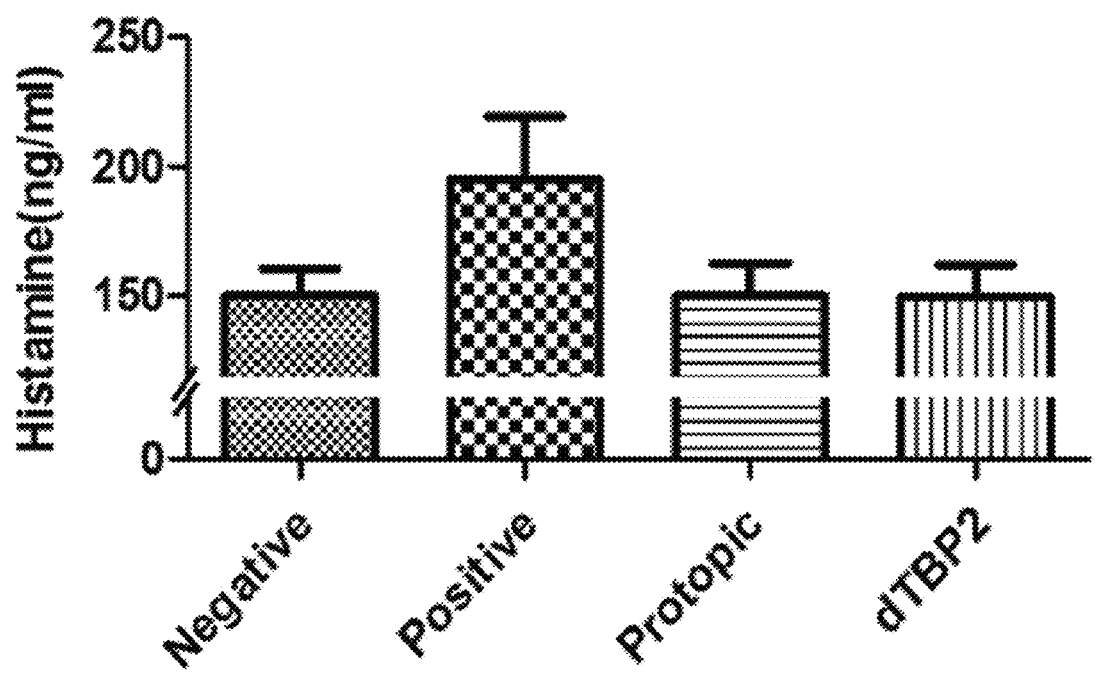
FIG. 36 is a graph illustrating the histamine level indicating the anti-allergic activity of dTBP2 resulted from the inhibition of HRF.

From the investigation of the histamine level, it was confirmed that dTBP2 had anti-allergic activity by inhibiting dTCTP. The histamine level was lower in the group treated with protopic ointment or dTBP2 than in the PBS-treated group (FIG. 36).

Figure 37A:
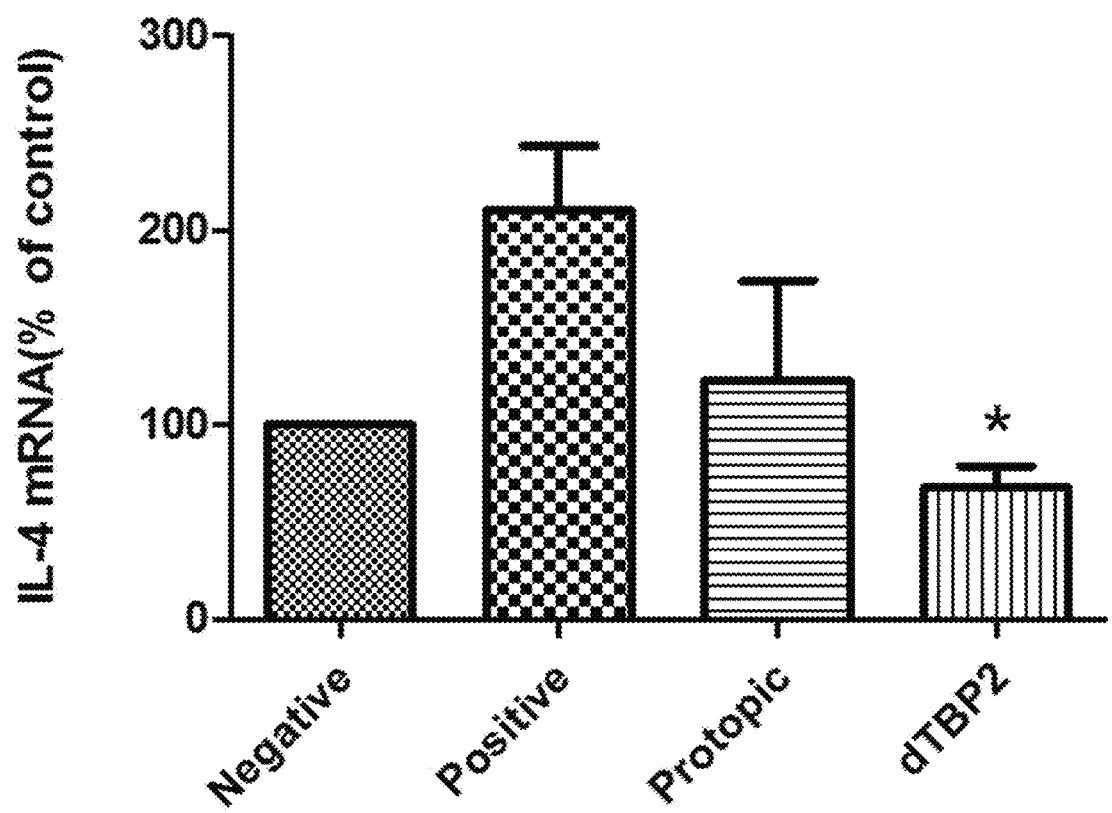
FIG. 37A is a graph illustrating the mRNA level of IL-4, the atopy-related Th2 cell cytokine.
Figure 37B:
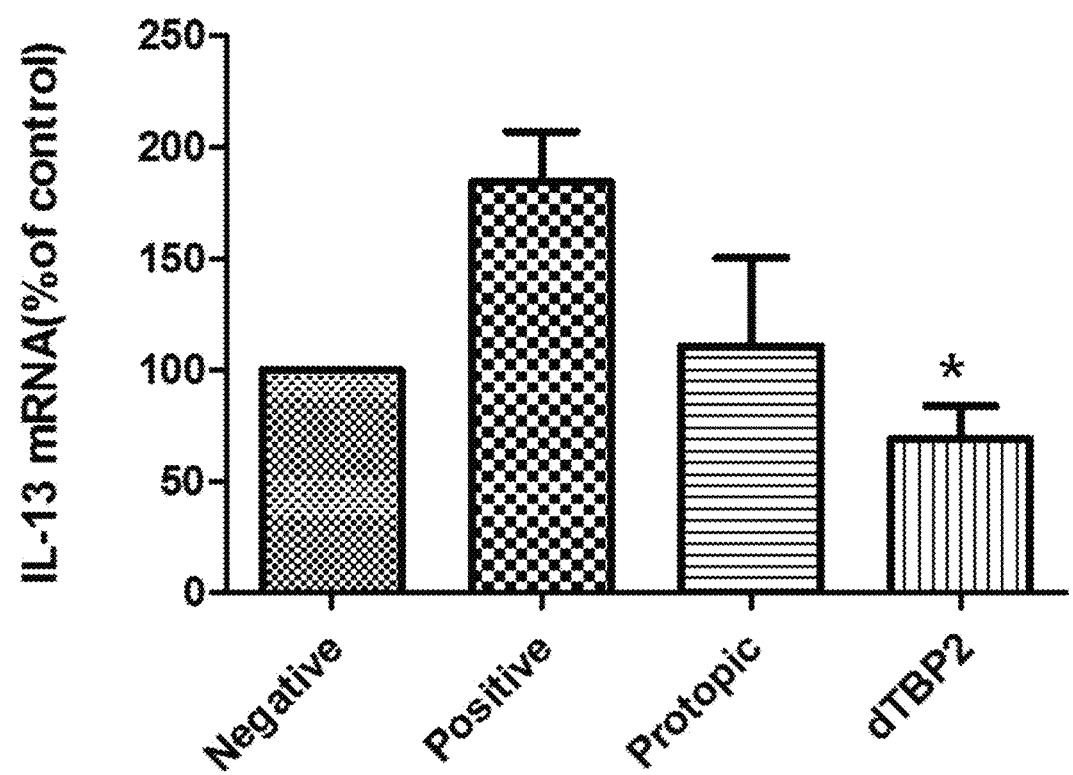
FIG. 37B is a graph illustrating the mRNA level of IL-13, the atopy-related Th2 cell cytokine.

The representative atopy-related Th2 cell cytokines, IL-4 and IL-13, were measured at mRNA levels. As a result, they were significantly decreased in the groups treated with dTBP2 and protopic ointment in that order, compared with the group treated with PBS (FIGS. 37a and 37b).

Figure 38:
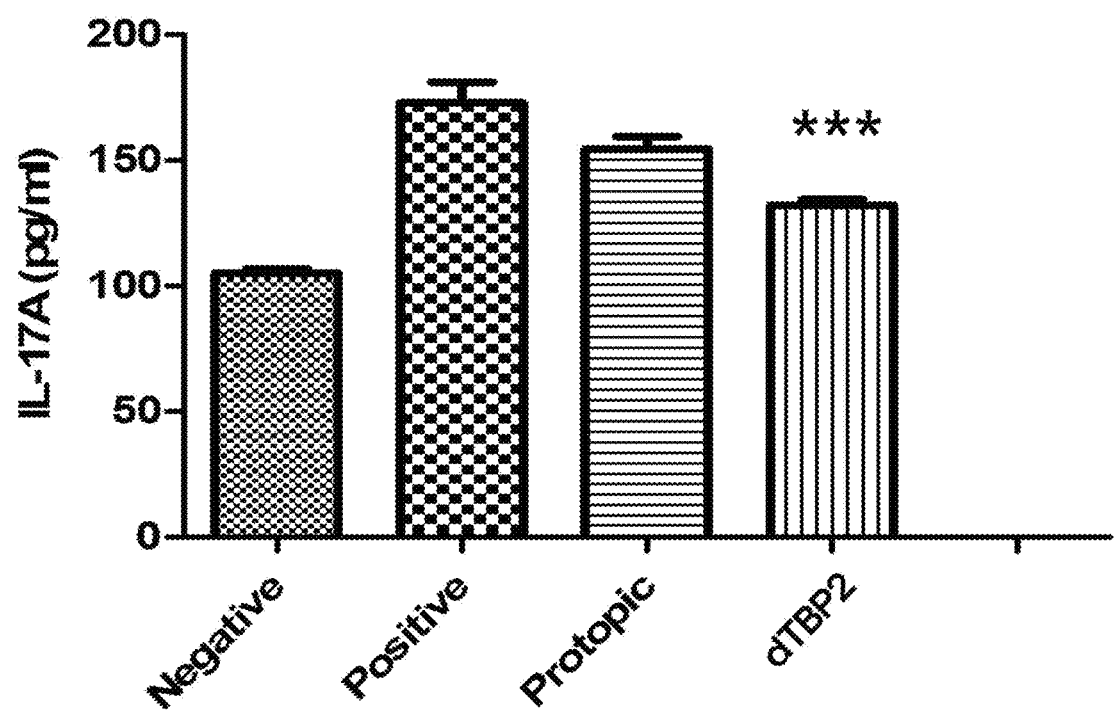
FIG. 38 is a graph illustrating the effect of dTBP2 on the reduction of Th17A.

According to the recent reports demonstrating that Th17 cells are also involved in atopic allergy and that Th17A, among the Th2 cell cytokines, is closely related to atopy, the effect of dTBP2 on Th17A was investigated. As a result, the level of Th17A was lowered in the groups treated with dTBP2 and protopic ointment in that order, compared with the group treated with PBS, suggesting that the dTBP2 of the invention had the inhibitory effect on Th17A as well (FIG. 38).

Experimental Example 12: Confirmation of Effect of dTCTP (HRF) on Rheumatoid Arthritis Whether TCTP is involved in rheumatoid arthritis (RA) is highly interested recently. Since the present inventors are the first who disclosed that TCTP dimer (dTCTP: HRF) is the histamine releasing factor causing allergic reaction, the inventors further performed the following experiment based on the expectation that one of the chronic inflammatory diseases, rheumatoid arthritis, is involved in dTCTP (HRF).

Particularly, synovial fluid was obtained from normal (negative) people, osteoarthritis (OA) patients, early rheumatoid arthritis (ERA) patients, and late rheumatoid arthritis (LRA) patients. TCTP detection ELISA (Antibody-protein-ELISA kit, MYBioSource, CA, USA) was performed with synovial fluid obtained above in order to investigate the level of dTCTP (HRF) involved in inflammatory reaction. It is hard to detect dTCTP (HRF) itself. However, because TCTP monomer is one of the components forming TCTP dimer, dTCTP, the increase of TCTP monomer leads to the increase of dimer form, dTCTP.

Figure 39:
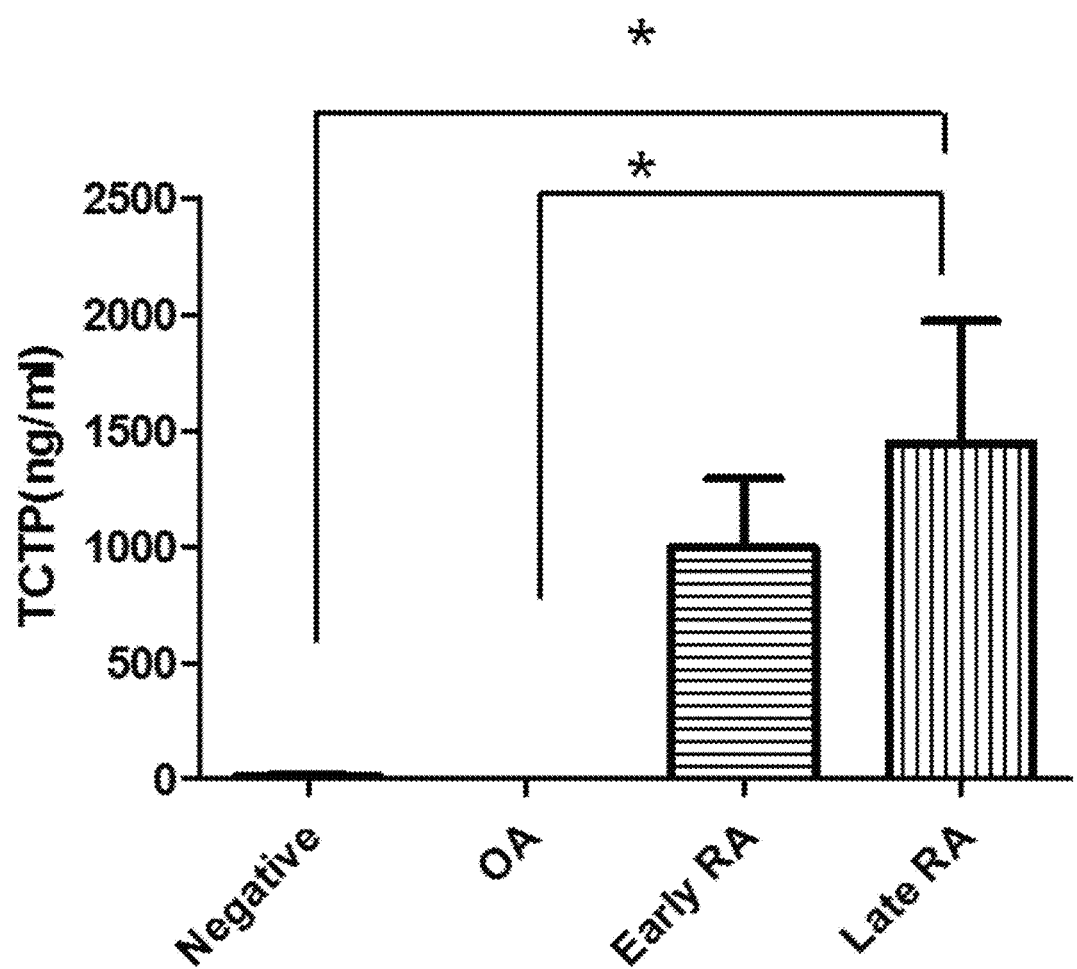
FIG. 39 is a graph illustrating the increase of TCTP according to the progress of rheumatoid arthritis.

Based on the idea above, the experiment was performed. As a result, TCTP was hardly detected in the samples obtained from normal people and osteoarthritis patients. In the meantime, the level of TCTP was increased as disease progressed in early rheumatoid arthritis patients and late rheumatoid arthritis patients (FIG. 39).

Figure 40:
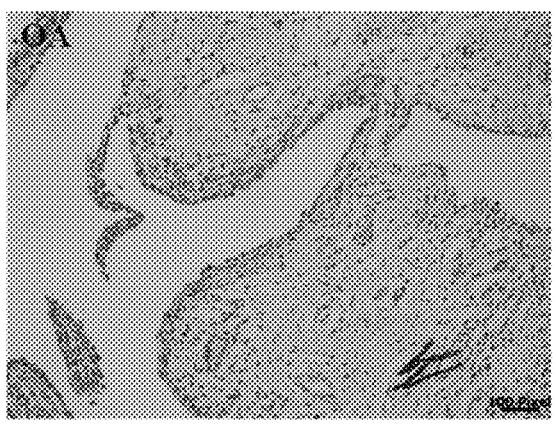
FIG. 40 is a diagram illustrating the distribution of TCTP in the joints of rheumatoid arthritis patients, confirmed by microscopic observation of IHC (immunohistochemistry) results.
Figure 40:
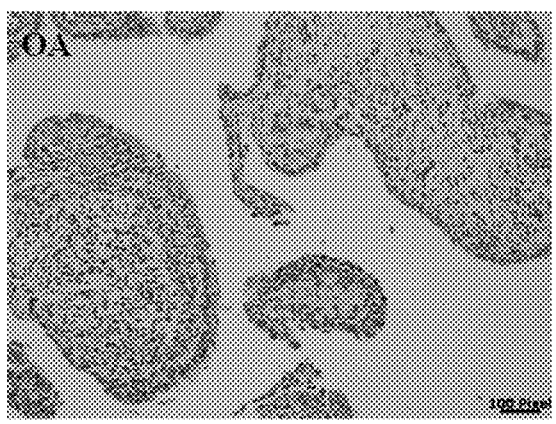
Figure 40:
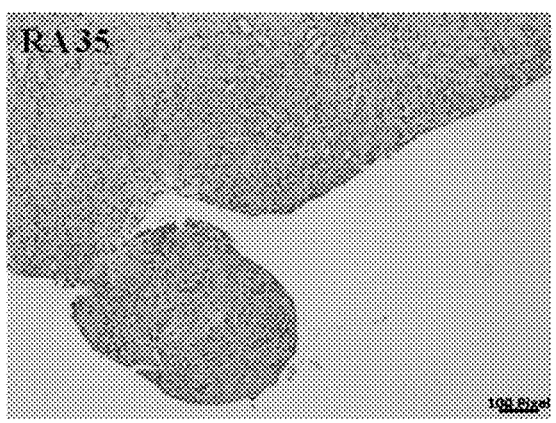
Figure 40:
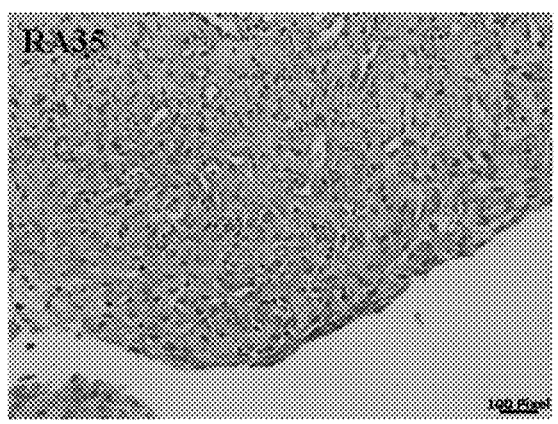

In addition, based on IHC (immunohistochemistry), TCTP localization and expression in the joint of each patient was observed under microscope. As shown in FIG. 40, the brown stained region represents TCTP. TCTP was richer in the joint tissues of late rheumatoid arthritis (RA) patients than in the joint tissues of osteoarthritis (OA) patients (FIG. 40).

Manufacturing Example 1: Preparation of Pharmaceutical Formulations

<1-1> Preparation of Powders

| HRF receptor binding inhibitor | 2 g |
|---|---|
| Lactose | 1 g |

Powders were prepared by mixing all the above components, which were filled in airtight packs according to the conventional method for preparing powders.

<1-2> Preparation of Tablets

| HRF receptor binding inhibitor | 100 mg |
|---|---|
| Corn starch | 100 mg |
| Lactose | 100 mg |
| Magnesium stearate | 2 mg |

Tablets were prepared by mixing all the above components by the conventional method for preparing tablets.

<1-3> Preparation of Capsules

| | |
|---|---|
| HRF receptor binding inhibitor | 100 mg |
| Corn starch | 100 mg |
| Lactose | 100 mg |
| Magnesium stearate | 2 mg |

Capsules were prepared by mixing all the above components, which were filled in gelatin capsules according to the conventional method for preparing capsules.

<1-4> Preparation of pills

| | |
|---|---|
| HRF receptor binding inhibitor | 1 g |
| Lactose | 1.5 g |
| Glycerin | 1 g |
| Xylitol | 0.5 g |

Pills were prepared by mixing all the above components according to the conventional method for preparing pills. Each pill contained 4 g of the mixture.

<1-5> Preparation of Granules

| | |
|---|---|
| HRF receptor binding inhibitor | 150 mg |
| Soybean extract | 50 mg |
| Glucose | 200 mg |
| Starch | 600 mg |

All the above components were mixed, to which 100 mg of 30% ethanol was added. The mixture was dried at 60° C. and the prepared granules were filled in packs.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A C-terminus domain peptide, wherein the amino acid sequence of the C-terminus domain peptide consists of SEQ ID NO: 33 or SEQ ID NO: 34, and wherein the peptide is modified with an N-terminal acetylation, a C-terminal amidation, or both.

2. The peptide of claim 1, wherein the amino acid sequence of the peptide consists of SEQ ID NO: 33.

3. The peptide of claim 2, wherein the peptide comprises an N-terminal acetylation and a C-terminal amidation.

4. The peptide of claim 1, wherein the amino acid sequence of the peptide consists of SEQ ID NO: 34.

5. The peptide of claim 4, wherein the peptide comprises an N-terminal acetylation and a C-terminal amidation.

6. A method for treating one or more diseases selected from the group consisting of allergic diseases and rheumatoid arthritis, comprising the step of administering the peptide of claim 1.

7. The method of claim 6, wherein the allergic disease comprises one or more of rhinitis, asthma, anaphylaxis, or atopy.

8. The method of claim 6, wherein the amino acid sequence of the peptide consists of SEQ ID NO: 33.

9. The method of claim 8, wherein the peptide comprises an N-terminal acetylation and a C-terminal amidation.

10. The method of claim 6, wherein the amino acid sequence of the peptide consists of SEQ ID NO: 34.

11. The method of claim 10, wherein the peptide comprises an N-terminal acetylation and a C-terminal amidation.

* * * * *